US011717563B2

(12) United States Patent
Mansour et al.

(10) Patent No.: US 11,717,563 B2
(45) Date of Patent: Aug. 8, 2023

(54) COMPOSITIONS COMPRISING LIPOSOMES, AN ANTIGEN, A POLYNUCLEOTIDE AND A CARRIER COMPRISING A CONTINUOUS PHASE OF A HYDROPHOBIC SUBSTANCE

(71) Applicant: IMMUNOVACCINE TECHNOLOGIES INC., Dartmouth (CA)

(72) Inventors: Marc Mansour, Halifax (CA); Leeladhar Sammatur, Irvine, CA (US); Lisa Diana MacDonald, Halifax (CA); Mohan Karkada, Rockville, MD (US); Genevieve Mary Weir, Medford, MA (US); Antar Fuentes-Ortega, Lac des Arcs (CA)

(73) Assignee: IMMUNOVACCINE TECHNOLOGIES INC., Dartmouth (CA)

( * ) Notice: Subject to any disclaimer, the term of this patent is extended or adjusted under 35 U.S.C. 154(b) by 0 days.

(21) Appl. No.: 16/283,486

(22) Filed: Feb. 22, 2019

(65) Prior Publication Data

US 2019/0290743 A1 Sep. 26, 2019

Related U.S. Application Data

(63) Continuation of application No. 12/992,512, filed as application No. PCT/CA2009/000692 on May 22, 2009, now abandoned.

(60) Provisional application No. 61/059,043, filed on Jun. 5, 2008.

(51) Int. Cl.

| | |
|---|---|
| ***A61K 39/00*** | (2006.01) |
| ***A61K 9/127*** | (2006.01) |
| ***A61K 9/10*** | (2006.01) |
| ***A61K 31/7088*** | (2006.01) |
| ***A61K 9/107*** | (2006.01) |
| ***A61K 47/06*** | (2006.01) |
| ***A61K 9/19*** | (2006.01) |
| ***A61K 31/785*** | (2006.01) |

(52) U.S. Cl.

CPC ................ *A61K 39/00* (2013.01); *A61K 9/10* (2013.01); *A61K 9/107* (2013.01); *A61K 9/127* (2013.01); *A61K 9/19* (2013.01); *A61K 31/785* (2013.01); *A61K 47/06* (2013.01); *A61K 2039/55555* (2013.01); *A61K 2039/55561* (2013.01); *Y02A 50/30* (2018.01)

(58) Field of Classification Search

None

See application file for complete search history.

(56) References Cited

U.S. PATENT DOCUMENTS

| | | | |
|---|---|---|---|
| 3,906,092 | A | 9/1975 | Hilleman |
| 4,610,868 | A | 9/1986 | Fountain et al. |
| 4,803,070 | A | 2/1989 | Cantrell et al. |
| 4,806,350 | A | 2/1989 | Gerber |
| 4,806,352 | A | 2/1989 | Cantrell |
| 4,920,016 | A | 8/1990 | Allen et al. |
| 5,013,556 | A | 5/1991 | Woodle et al. |
| 5,015,476 | A | 5/1991 | Cochrum et al. |
| 5,084,269 | A | 1/1992 | Kullenberg |
| 5,340,588 | A | 8/1994 | Domb |
| 5,422,109 | A | 6/1995 | Brancq et al. |
| 5,545,412 | A | 8/1996 | Eppstein et al. |
| 5,637,300 | A | 6/1997 | Dunbar et al. |
| 5,662,931 | A | 9/1997 | Munechika et al. |
| 5,688,772 | A | 11/1997 | Estrada et al. |
| 5,705,151 | A | 1/1998 | Dow et al. |
| 5,709,879 | A | 1/1998 | Barchfeld et al. |
| 5,736,141 | A | 4/1998 | Brown et al. |
| 5,820,879 | A | 10/1998 | Fernandez et al. |
| 5,831,016 | A | 11/1998 | Wang et al. |
| 5,844,075 | A | 12/1998 | Kawakami et al. |
| 5,855,894 | A | 1/1999 | Brown et al. |
| 5,863,549 | A | 1/1999 | Tarantino |
| 5,897,873 | A | 4/1999 | Popescu |
| 5,910,306 | A | 6/1999 | Alving et al. |
| 5,919,480 | A | 7/1999 | Kedar et al. |
| 5,980,898 | A | 11/1999 | Glenn et al. |
| 5,990,287 | A | 11/1999 | Hosokawa et al. |
| 6,037,135 | A | 3/2000 | Kubo et al. |
| 6,080,725 | A | 6/2000 | Marciani |
| 6,090,406 | A | 7/2000 | Popescu et al. |
| 6,093,406 | A | 7/2000 | Alving et al. |
| 6,096,313 | A | 8/2000 | Jäger et al. |
| 6,110,492 | A | 8/2000 | Alving et al. |
| 6,124,270 | A | 9/2000 | Haensler |

(Continued)

FOREIGN PATENT DOCUMENTS

| | | |
|---|---|---|
| CA | 2078990 | 10/1991 |
| CA | 2082155 | 11/1991 |

(Continued)

OTHER PUBLICATIONS

Klinman et al., J. Immunol., 1997, 158: 3635-3639.*

(Continued)

*Primary Examiner* — Ileana Popa

(74) *Attorney, Agent, or Firm* — Troutman Pepper Hamilton Sanders LLP

(57) ABSTRACT

The invention provides a composition comprising: an antigen; liposomes; a polyI:C polynucleotide; and a carrier comprising a continuous phase of a hydrophobic substance. Methods for making and using the compositions are also provided.

26 Claims, 7 Drawing Sheets

Specification includes a Sequence Listing.

(56) References Cited

U.S. PATENT DOCUMENTS

| | | | |
|---|---|---|---|
| 6,168,804 | B1 | 1/2001 | Amuet et al. |
| 6,183,746 | B1 | 2/2001 | Urban et al. |
| 6,214,367 | B1 | 4/2001 | Harvey |
| 6,218,371 | B1 | 4/2001 | Krieg et al. |
| 6,228,648 | B1 | 5/2001 | Condon et al. |
| RE37,224 | E | 6/2001 | Brown et al. |
| 6,248,353 | B1 | 6/2001 | Singh |
| 6,267,985 | B1 | 7/2001 | Chen et al. |
| 6,284,267 | B1 | 9/2001 | Aneja |
| 6,291,430 | B1 | 9/2001 | Chaux et al. |
| 6,306,405 | B1 | 10/2001 | O'Hagen et al. |
| 6,309,569 | B1 | 10/2001 | Farrar et al. |
| 6,355,247 | B1 | 3/2002 | Selby et al. |
| 6,355,256 | B1 | 3/2002 | Noguchi et al. |
| 6,372,227 | B1 | 4/2002 | Garcon et al. |
| 6,406,719 | B1 | 6/2002 | Farrar et al. |
| 6,451,325 | B1 | 9/2002 | Van Nest et al. |
| 6,464,980 | B1 | 10/2002 | Fikes et al. |
| 6,468,558 | B2 | 10/2002 | Wong |
| 6,472,159 | B1 | 10/2002 | Darbouret et al. |
| 6,472,375 | B1 | 10/2002 | Hoon et al. |
| 6,497,896 | B2 | 12/2002 | Sands et al. |
| 6,511,676 | B1 | 1/2003 | Boulikas |
| 6,517,816 | B1 | 2/2003 | Gonzalez et al. |
| 6,528,058 | B1 | 3/2003 | Edgar et al. |
| 6,534,064 | B1 | 3/2003 | O'Hagan et al. |
| 6,537,966 | B1 | 3/2003 | Duan et al. |
| 6,544,518 | B1 | 4/2003 | Frtfde et al. |
| 6,572,861 | B1 | 6/2003 | Roberts et al. |
| 6,588,671 | B2 | 7/2003 | King et al. |
| 6,602,510 | B1 | 8/2003 | Fikes et al. |
| 6,630,161 | B1 | 10/2003 | Leesman |
| 6,632,447 | B1 | 10/2003 | Steiner et al. |
| 6,649,172 | B2 | 11/2003 | Johnson |
| 6,565,777 | B2 | 12/2003 | Farrar et al. |
| 6,670,195 | B1 | 12/2003 | Ghiso et al. |
| 6,676,958 | B2 | 1/2004 | Gerber |
| 6,780,421 | B1 | 8/2004 | Haensler et al. |
| 6,790,457 | B1 | 9/2004 | Brown et al. |
| 6,793,923 | B2 | 9/2004 | Brown et al. |
| 6,838,089 | B1 | 1/2005 | Carlsson et al. |
| 6,881,405 | B2 | 4/2005 | Leveugle et al. |
| 6,956,021 | B1 | 10/2005 | Edwards et al. |
| 6,977,074 | B2 | 12/2005 | Kundig et al. |
| 6,982,314 | B2 | 1/2006 | Rosey |
| 7,019,112 | B1 | 3/2006 | Slingluff et al. |
| 7,026,443 | B1 | 4/2006 | Sette et al. |
| 7,037,509 | B2 | 5/2006 | Koelle et al. |
| 7,056,515 | B2 | 6/2006 | Brown et al. |
| 7,067,120 | B2 | 6/2006 | Dianwen et al. |
| 7,087,236 | B1 | 8/2006 | Brayden |
| 7,122,191 | B2 | 10/2006 | Dominowski et al. |
| 7,148,191 | B2 | 12/2006 | Egyed et al. |
| 7,179,645 | B2 | 2/2007 | Humphreys et al. |
| 7,306,787 | B2 | 12/2007 | Tarara et al. |
| 7,604,802 | B2 | 10/2009 | O'Hagan |
| 7,611,721 | B1 | 11/2009 | Hagen |
| 7,687,455 | B2 | 3/2010 | Bonnet et al. |
| 7,824,686 | B2 | 11/2010 | Brown et al. |
| 7,943,147 | B2 | 5/2011 | Carter et al. |
| 9,498,493 | B2 | 11/2016 | Mansour |
| 2002/0110568 | A1 | 8/2002 | Brown et al. |
| 2003/0003105 | A1 | 1/2003 | Gerber |
| 2003/0044454 | A1 | 3/2003 | Fukui et al. |
| 2003/0161834 | A1 | 8/2003 | Friede et al. |
| 2003/0185879 | A1 | 10/2003 | Boulikas |
| 2003/0202979 | A1 | 10/2003 | Gerber |
| 2003/0211115 | A1 | 11/2003 | Gerber |
| 2003/0211140 | A1 | 11/2003 | Mantripragada et al. |
| 2003/0220284 | A1 | 11/2003 | Yotnda et al. |
| 2004/0170640 | A1 | 9/2004 | Gerber |
| 2004/0202669 | A1 | 10/2004 | O'Hagen |
| 2004/0213837 | A1 | 10/2004 | Mantripragada et al. |
| 2004/0223977 | A1 | 11/2004 | Diamond |
| 2004/0253731 | A1 | 12/2004 | Holliger et al. |
| 2004/0258701 | A1 | 12/2004 | Dominowski et al. |
| 2005/0002952 | A1 | 1/2005 | Haensler et al. |
| 2005/0002999 | A1 | 1/2005 | Mehta et al. |
| 2005/0013812 | A1 | 1/2005 | Dow |
| 2005/0019339 | A1 | 1/2005 | Brown et al. |
| 2005/0037061 | A1 | 2/2005 | Hosokawa et al. |
| 2005/0049197 | A1 | 3/2005 | Sette et al. |
| 2005/0079208 | A1 | 4/2005 | Albani |
| 2005/0084524 | A1 | 4/2005 | Martin et al. |
| 2005/0118154 | A1 | 6/2005 | Hung et al. |
| 2005/0158375 | A1 | 7/2005 | Kimura et al. |
| 2005/0175683 | A1 | 8/2005 | Zhang et al. |
| 2005/0202078 | A1 | 9/2005 | Schiffelers et al. |
| 2005/0214322 | A1 | 9/2005 | Garcon et al. |
| 2005/0220781 | A1 | 10/2005 | Yan et al. |
| 2005/0220814 | A1 | 10/2005 | Dominowski et al. |
| 2005/0249795 | A1 | 11/2005 | Zhang et al. |
| 2005/0260643 | A1 | 11/2005 | Hung et al. |
| 2005/0266066 | A1 | 12/2005 | Uchida et al. |
| 2006/0008909 | A1 | 1/2006 | Cullis et al. |
| 2006/0034908 | A1 | 2/2006 | Bhamidipati et al. |
| 2006/0120997 | A1 | 6/2006 | Lipton |
| 2006/0153844 | A1 | 7/2006 | Kundig |
| 2006/0182792 | A1 | 8/2006 | Richardsen et al. |
| 2006/0183670 | A1 | 8/2006 | Orban |
| 2006/0275777 | A1 | 12/2006 | Waelti |
| 2006/0286038 | A1 | 12/2006 | Rairkar et al. |
| 2007/0014805 | A1 | 1/2007 | Dalencon et al. |
| 2007/0059318 | A1 | 3/2007 | Balu-Iyer et al. |
| 2007/0082855 | A1 | 4/2007 | Veldman et al. |
| 2007/0141078 | A1 | 6/2007 | D'Hondt et al. |
| 2007/0212329 | A1 | 9/2007 | Bruck et al. |
| 2007/0274980 | A1 | 11/2007 | Balu-Iyer et al. |
| 2007/0298093 | A1 | 12/2007 | Konur |
| 2008/0014217 | A1 | 1/2008 | Hanon et al. |
| 2008/0050395 | A1 | 2/2008 | Gerber |
| 2009/0017057 | A1 | 1/2009 | Chen et al. |
| 2009/0035266 | A1 | 2/2009 | Schlom et al. |
| 2009/0074853 | A1 | 3/2009 | Brown et al. |
| 2009/0081244 | A1 | 3/2009 | Glenn et al. |
| 2009/0092666 | A1 | 4/2009 | Brown et al. |
| 2009/0124549 | A1 | 5/2009 | Lewinsohn et al. |
| 2009/0169636 | A1 | 7/2009 | O'Hagen et al. |
| 2009/0247456 | A1 | 10/2009 | Srivastava et al. |

FOREIGN PATENT DOCUMENTS

| | | | | |
|---|---|---|---|---|
| CA | 2086094 | | | 12/1991 |
| CA | 2115424 | | | 3/1993 |
| CA | 2183435 | | | 8/1995 |
| CA | 2205083 | | | 5/1996 |
| CA | 2137363 | | | 6/1999 |
| CA | 2436348 | | | 6/2002 |
| CA | 1473621 | A | | 2/2004 |
| CA | 2523032 | | | 4/2007 |
| CA | 2542212 | | | 4/2007 |
| CA | 2533705 | | | 7/2007 |
| EP | 0 640 347 | A1 | | 3/1995 |
| EP | 1333858 | | | 2/2006 |
| GB | 2134869 | | | 8/1984 |
| JP | 09 25238 | | | 1/1997 |
| JP | 2002-532163 | | | 10/2002 |
| JP | 2004-512384 | | | 4/2004 |
| JP | 2004-525115 | | | 8/2004 |
| JP | 2007-532629 | | | 11/2007 |
| WO | WO 92/00081 | | | 1/1992 |
| WO | WO 92/10513 | | | 6/1992 |
| WO | WO 93/25231 | | | 12/1993 |
| WO | WO 1995/31480 | | | 11/1995 |
| WO | 96/014871 | A1 | | 5/1996 |
| WO | 98/53799 | A2 | | 12/1998 |
| WO | WO 1999/27944 | | * | 10/1999 |
| WO | WO 2000/37100 | | | 6/2000 |
| WO | WO 2002/38175 | | | 5/2002 |
| WO | 02/070006 | A2 | | 9/2002 |
| WO | WO 2003/066680 | | | 8/2003 |
| WO | 2004/000873 | A2 | | 12/2003 |
| WO | WO 2004/052917 | | | 6/2004 |
| WO | WO 2004/058179 | | | 7/2004 |

(56) References Cited

FOREIGN PATENT DOCUMENTS

| | | | |
|---|---|---|---|
| WO | WO 2004/094454 | | 11/2004 |
| WO | WO 2005/019435 | | 3/2005 |
| WO | WO 2005/025614 | | 3/2005 |
| WO | 2005/072777 | A2 | 8/2005 |
| WO | WO 2005/089164 | | 9/2005 |
| WO | WO 2006/050155 | | 5/2006 |
| WO | WO 2006/113679 | | 10/2006 |
| WO | WO 2007/041832 | | 4/2007 |
| WO | WO 2007/071707 | | 6/2007 |
| WO | WO 2007/071710 | | 6/2007 |
| WO | WO 2007/071711 | | 6/2007 |
| WO | WO 2008/000261 | | 1/2008 |
| WO | WO2009043165 | A1 | 4/2009 |

OTHER PUBLICATIONS

Dass, Drug Delivery, 2002, 9: 169-180.*
Lingnau et al., Expert Rev. Vaccines, 2007, 6: 741-746.*
Beljanski, Vladimir et al., "Enhanced Influenza Virus-Like Particle Vaccination with a Structurally Optimized RIG-I Agonist as Adjuvant", Journal of Virology, Oct. 2015, vol. 89, No. 28, pp. 10612-10624.
De Gregorio, Ennio et al., "Alum adjuvanticity: Unraveling a century old mystery", European Journal of Immunology, 2008, vol. 38, pp. 2068-2071.
Fransen, Floris et al., "Agonists of Toll-Like Receptors 3,4, 7, and 9 are Candidates for Use as Adjuvants in an Outer Membrane Vaccine against Neisseria Meningitidis Serogroup B", Infection and Immunity, Dec. 2007, vol. 75, No. 12, pp. 5939-5946.
First Examination Report for POC/Application No. 7749/CHENP/2010.
2014-231396 Decision of Rejection and English Translation FP10-0388A.
2014-231396 Decision to Dismiss Amendment and English Translation FP10-0388A.
Dileo et al., Molecular Therapy, vol. 7, No. 5, May 2003 pp. 640-648.
Tai et al., A Universal T Cell Vaccine Against Influenza A, The FASEB Journal, Apr. 2008, vol. 22. Abstract No. 853.11.
Maes et al., Potentiation of FMD vaccines with polycationic-nucleic acid complexes, Arch Virol. 1977 vol. 55, No. 4, p. 275-85.
Compagnon et al., Targeting of Poly(rl)-Poly(rC) bY Fusogenic (F Protein) Immunoliposomes, Experimetal Cell research 200, 333-338 (1992.
Supplementary European Search Report for related EP application No. EP 09 75 6985 dated Mar. 22, 2012.
Adam, J.K. et al., "Immune responses in cancer", Pharmacol. Ther., (2003) p. 113-132, vol. 99.
Agger, E.M. et al, "Protective immunity to tuberculosis with Ag85B-ESAT-6 in a synthetic cationic adjuvant system IC31", Vaccine, (2006) p. 5452-5460, vol. 24.
Alexander, J. et al., "Development of high potency universal DR-restricted helper epitopes by modification of high affinity DR-blocking peptides", Immunity (1994) p. 751-761, vol. 1.
Alexopoulou, L. et al., "Recognition of double-stranded RNA and activation of NF-kappaB by Toll-like receptor 3", Nature, (2001) p. 732-738, vol. 413.
Allegra, C.J. et al., "Cytotoxins and cancer immunotherapy: The dance of the macabre?", J. National Cancer Institute, (2005) p. 1396-1397, vol. 97.
Altschul, S.F. et al., "Basic Local Alignment Search Tool", J. Mol. Biol., (1990) p. 403-410, vol. 215.
Alving, C.R., "Design and selection of vaccine adjuvants: animal models and human trials", Vaccine, (2002) p. S56-S64, vol. 20.
Antonia, S.J. et al., "Combination of p53 cancer vaccine with chemotherapy in patients with extensive stage small cell lung cancer" Clinical Cancer Research, (2006) p. 878-887, vol. 12.
Awasthi, A. et al., "Poly ICLC enhances the antimalarial activity of chloroquine against multidrug-resistant Plasmodium yoelii nigeriensis in mice", J Interferon Cytokine Res., (1997) p. 419-423, vol. 17.
Bagavant et al., "Antifertility effects of porcine zona pellucida-3 immunization using permissible adjuvants in female bonnet monkeys (*Macaca radiata*): reversibility, effect on follicular development and hormonal profiles", J. Reprod. Fertil., (1994) p. 17-25, vol. 102.
Banga, A.K., Therapeutic Peptides and Proteins, Formulations, Processing and Delivery Systems, (1995), Technomic Publishing Co., Lancaster, PA.
Bellone, M. et al., "Relevance of the tumor antigen in the validation of three vaccination strategies for melanoma", Journal of Immunology, (2000) p. 2651-2656, vol. 165, No. 5.
Bever, C.T. et al., "Preliminary trial of poly ICLC in chronic progressive multiple sclerosis", Neurology, (1986) p. 494-498, vol. 36.
Bobst, A.M. et al., "Interferon induction by poly(inosinic acid). poly(cytidylic acid) segmented by spin-labels", Biochemistry, (1981) p. 4798-4803, vol. 20.
Bosch, F.X. et al., "Prevalence of human papillomavirus in cervical cancer: a worldwide perspective", J. Natl. Cancer Inst., (1995) p. 796-802, vol. 87.
Bronte, V. et al., "Genetic Vaccination with "Self" Tyrosinase-related Protein 2 Causes Melanoma Eradication but not Vitiligo", Cancer Research, (Jan. 15, 2000) p. 253-258, vol. 60.
Brown, R.G. et al., "Evidence for a long-lasting single administration contraceptive vaccine in wild grey seals", J. Reprod. Immunol., (1997) p. 43-51, vol. 35.
Brown, R.G. et al., "Temporal trends in antibody production in captive grey, harp and hooded seals to a single administration immunocontraceptive vaccine", J. Reprod. Immunol., (1997) p. 53-64, vol. 35.
Cassarino, D.S. et al., "The effects of gp100 and tyrosinase peptide vaccinations on nevi in melanoma patients", J. Cutaneous Path., (2006) p. 335-342, vol. 33.
Celis E. et al., "Recognition of hepatitis B surface antigen by human T lymphocytes. Proliferative and cytotoxic responses to a major antigenic determinant defined by synthetic peptides", Journal of Immunology, (1988) p. 1808-1815, vol. 140.
Chakraborty, M. et al., "External beam radiation of tumors alters phenotype of tumor cells to render them susceptible to vaccine-mediated T-cell killing", Cancer Research, (2004) p. 4328-4337, vol. 64.
Chen, Y.F. et al., "Cytotoxic-T-lymphocyte human papillomavirus type 16 E5 peptide with CpG-oligodeoxynucleotide can eliminate tumor growth in C57BL/6 mice", J. Virol. (Feb. 2004) p. 1333-1343, ISSN 0022-538X, vol. 78, No. 3.
Chikh, G. et al., "Liposomal delivery of CTL epitopes to dendritic cells", Biosci. Rep. (Apr. 2002) p. 339-353, ISSN 0144-8463, vol. 22, No. 2.
Chirigos, M.A. et al., "Pharmacokinetic and therapeutic activity of polyinosinic-polycytidylic acid stabilized with poly-L-lysine in carboxymethylcellulose [poly(I,C)-LC]", J Biol Response Mod, (1985) p. 621-627, vol. 4.
Chong P. et al., "Identification of T- and B-cell epitopes of the S2 and S3 subunits of pertussis toxin by use of synthetic peptides", Infection and Immunity, (1992) p. 4640-4647, vol. 60.
Copland, M.J. et al., "Lipid based particulate formulations for the delivery of antigen", Immunol. Cell Biol., (2005) p. 97-105, vol. 83.
Correale, P. et al., "Fluorouracil-based chemotherapy enhances the antitumor activity of a thymidylate synthase-directed polyepitopic peptide vaccine", Journal of the National Cancer Institute, (2005) p. 1437-1445, vol. 97.
Cox, J.C. et al., "Adjuvants—a classification and review of their modes of action", Vaccine, (1997) p. 248-256, vol. 15, No. 3.
Cui, Z. et al., "Liposome-polycation-DNA (LPD) particle as a carrier and adjuvant for protein-based vaccines: Therapeutic effect against cervical cancer", Cancer Immunol. Immunother. (2005) p. 1180-1190, vol. 54.

(56) References Cited

OTHER PUBLICATIONS

Cui, Z. & Qui, F., "Synthetic double-stranded RNA poly(I:C) as a potent peptide vaccine adjuvant: therapeutic activity against human cervical cancer in a rodent model", Cancer Immunol Immunother, (2006) p. 1267-1269, vol. 55.
Da Silva, D.M. et al., "Heterologous boosting increases immunogenicity of chimeric papillomavirus virus-like particle vaccines", Vaccine, (2003) p. 3219-3227, vol. 21.
Daftarian, P. et al., "Eradication of established HPV 16-expressing tumors by a single administration of a vaccine composed of a liposome-encapsulated CTL-T helper fusion peptide in a water-in-oil emulsion", Vaccine (2006) p. 5235-5244, vol. 24, No. 24.
Daftarian, P. et al., "Two distinct pathways of immuno-modulation improve potency of p53 immunization in rejecting established tumors", Cancer Res., (2004) p. 5407-5414, vol. 64.
Daftarian, P. et al. "Rejection of large HPV-16 expressing tumours in aged mice by a single immunization of VacciMax® encapsulated CTL/T helper peptides", J. Trans. Med., (Jun. 2007), p. 1-9, vol. 5, No. 26.
Davis, H.L. et al., "CpG DNA is a Potent Enhancer of Specific Immunity in Mice Immunized with Recombinant Hepatitis B Surface Antigen", J. Immunol., (1998) p. 870-876, vol. 160.
De Clercq, E. et al., "Antiviral activity of polynucleotides:copolymers of inosinic acid and N2-dimethylguanylic of 2-methylthioinosinic acid", Nucleic Acids Res, (1975) p. 121-129, vol. 2.
De Clercq, E. et al. "Interferon induction by a 2'-modified double-helical RNA, poly(2'-azido-2'-deoxyinosinic acid) . polycytidylic acid", Eur J Biochem, (1978) p. 341-349, vol. 88.
Demotz S. et al., "Delineation of several DR-restricted tetanus toxin T cell epitopes", Journal of Immunology, (1989) p. 394-402, vol. 142.
Diethelm-Okita, B.M. et al., "Universal epitopes for human $CD4^+$ cells on tetanus and diphtheria toxins", Journal of Infectious Diseases, (2000) p. 1001-1009, vol. 181.
Dong, L.W. et al., "Signal regulatory protein alpha negatively regulates both TLR3 and cytoplasmic pathways in type 1 interferon induction", Mol Immunol, (2008) p. 3025-3035, vol. 45.
Dudley, M.E. et al., "Adoptive transfer of cloned melanoma-reactive T lymphocytes for the treatment of patients with metastatic melanoma", Journal of Immunotherapy, (2001) p. 363-373, vol. 24, No. 4.
Durie, B.G. et al., "Poly(I,C)-LC as an interferon inducer in refractory multiple myeloma", J Biol Response Mod., (1985) p. 518-524, vol. 4.
Edelman et al., "Adjuvants", Intern. Rev. Immunol., (1990) p. 51-66, vol. 7, No. 1.
Fagerstone, K. A. et al., "Wildlife Fertility Control", The Wildlife Society Technical Review 02-2, (2002) p. 1-29, University of Nebraska—Lincoln.
Fausch, S.C. et al., "Human Papillomavirus Can Escape Immune Recognition through Langerhans Cell Phosphoinositide 3-Kinase Activation", J. Immunol., (2005) p. 7172-7178, vol. 174.
Feltkamp, M.C. et al., "Vaccination with cytotoxic T lymphocyte epitope-containing peptide protects against a tumor induced by human papillomavirus type 16-transformed cells", Eur. J. Immunol., (1993) p. 2242-2249, vol. 23.
Fernando, G.J. et al., "Vaccine-induced Th1-type responses are dominant over Th2-type responses in the short term whereas pre-existing Th2 responses are dominant in the longer term", Scandinavian Journal of Immunology, (1998) p. 459-465, vol. 47 No. 5.
Fraker, M.A. et al., "Long-Lasting, Single-Dose Immunocontraception of Feral Fallow Deer in British Columbia", J. Wildl. Manage., (2002) p. 1141-1147 vol. 66.
Frazer, I.H., "Prevention of cervical cancer through papillomavirus vaccination", Nat. Rev. Immunol., (2004) p. 46-54, vol. 4.
Frey, A. et al., "A statistically defined endpoint titer determination method for immunoassays", J Immunol Methods, (1998) p. 35-41, vol. 221.
Fréard, F., "Liposomes: from biophysics to the design of peptide vaccines", Brazilian Journal of Medical Biology and Research, (1999) p. 181-189, vol. 32.
Fujimura, T. et al., "Inhibitory effect of the polyinosinic-polycytidylic acid/cationic liposome on the progression of murine B16F10 melanoma", Eur J Immunol, (2006) p. 3371-3380, vol. 36.
Fukui, T. et al., "XLV Synthesis and properties of poly(2'-azido-2'-deoxyinosinic acid)", Nucleic Acids Res., (1977) p. 2629-2639, vol. 4.
Gerard, C.M. et al., "Therapeutic potential of protein and adjuvant vaccinations on tumour growth", Vaccine, (2001) p. 2583-2589, vol. 19.
Gillison, M.L., "Human papillomavirus-associated head and neck cancer is a distinct epidemiologic, clinical, and molecular entity", Semin. Oncol., (2004) p. 744-754, vol. 31.
Goedert, M. et al., "A Century of Alzheimer's Disease", Science, (2006) p. 777-81, vol. 314.
Gorman, S.P. et al., "Evaluation of a porcine zona pellucida vaccine for the immunocontraception of domestic kittens (*Felis catus*)", Theriogenology, (2002) p. 135-149, vol. 58.
Gowen, B.B. et al., "TLR3 is essential for the induction of protective immunity against Punta Toro Virus infection by the double-stranded RNA (dsRNA), poly(I:C12U), but not Poly(I:C): differential recognition of synthetic dsRNA molecules", J Immunol, (2007) p. 5200-5208, vol. 178.
Greene, J.J. et al. "Interferon induction and its dependence on the primary and secondary structure of poly(inosinic acid). poly(cytidylic acid)", Biochemistry, (1978) p. 4214-4220, vol. 17.
Gregoriadis, G., "Immunological adjuvants: A role for liposomes", Immunology Today, (1990) p. 89-97, vol. 11, No. 3.
Gulley, J.L. et al., "Combining a recombinant cancer vaccine with standard definitive radiotherapy in patients with localized prostate cancer", Clinical Cancer Research, (2005) p. 3353-3362 vol. 11.
Gupta et al., "Adjuvants—a balance between toxicity and adjuvanticity", Vaccine, (1993) p. 293-306, vol. 11, No. 13.
Gupta, R. et al., "Adjuvants for human vaccines—current status, problems and future prospects", Vaccine, (1995) p. 1263-1276, vol. 13, No. 14.
Guschlbauer, W. et al., "Poly-2'-deoxy-2'-fluoro-cytidylic acid: enzymatic synthesis, spectroscopic characterization and interaction with poly-inosinic acid", Nucleic Acids Res, (1977) p. 1933-43, vol. 4.
Guy, B. "The perfect mix: recent progress in adjuvant research", Nat Rev Microbiol., (2007) p. 505-517, vol. 5.
Harada, M. et al., "Vaccination of cytotoxic T lymphocyte-directed peptides elicited and spread humoral and Th1-type immune responses to prostate-specific antigen protein in a prostate cancer patient", J. Immunother. (Jul.-Aug. 2005) p. 368-375, ISSN 1524-9557, vol. 28, No. 4.
Harrenstein, L.A. et al., "Effects of Porcine Zona Pellucida Immunocontraceptives in Zoo Felids", J. Zoo Wildlife Medicine, (2004) p. 271-279, vol. 35.
Hendrix, C.W. et al. "Biologic effects after a single dose of poly(1):poly(C12U) in healthy volunteers", Antimicrob. Agents Chemother., (1993) p. 429-435, vol. 37.
Hilbert, A. et al., "Biodegradable microspheres containing influenza A vaccine: immune response in mice", Vaccine, (1999) p. 1065-1073, vol. 17, No. 9-10.
Houston, W.E. et al., "Modified polyriboinosinic-polyribocytidylic acid, an immunological adjuvant", Infect Immun, (1976) p. 318-319, vol. 14.
Husband, A.J., "Novel vaccination strategies for the control of mucosal infection", Vaccine, (1993) p. 107-112, vol. 11, No. 2 (abstract only).
Ichinohe, T. et al., "Cross-protection against H5N1 influenza virus infection is afforded by intranasal inoculation with seasonal trivalent inactivated influenza vaccine", J Infect Dis., (2007) p. 1313-1320, vol. 196.
Itoh, T. et al., "Transcutaneous immunization with cytotoxic T-cell peptide epitopes provides effective antitumor immunity in mice", J. Immunother., (2005) p. 430-437, vol. 28.
Itzhaki, R.F. et al., "Simplex Virus Type 1 in Alzheimer's Disease: The Enemy Within", J Alzheimers Dis., (2008) p. 393-405, vol. 13.

(56) References Cited

OTHER PUBLICATIONS

Ivanova et al., "Contraceptive potential of porcine zona pellucida in cats", Theriogenology, (1995) p. 969-981, vol. 43.
Jentoft, N. et al., "Labeling of proteins by reductive methylation using sodium cyanoborohydride", J. Biol. Chem., (1979) p. 4359-4365, vol. 254, No. 11.
Jerome, V. et al, "Cytotoxic T lymphocytes responding to low dose TRP2 antigen are induced against B16 melanoma by liposome-encapsulated TRP2 peptide and CpG DNA adjuvant", J. Immunother., (2006) p. 294-305, vol. 29, No. 3.
Jin, B. et al., "Induction of potent cellular immune response in mice by hepatitis C virus NS3 protein with double-stranded RNA", Immunology, (2007) p. 15-27, vol. 122.
Johnston, M.I. et al., "Structural features of double-stranded polyribonucleotides required for immunological specificity and interferon induction", Proc Natl Acad Sci USA, (1975) p. 4564-4568, vol. 72.
Kadowaki, N. et al., "Subsets of human dendritic cell precursors express different toll-like receptors and respond to different microbial antigens", J. Exp. Med., (2001) p. 863-869, vol. 194.
Kamath, A.T. et al., "Protective anti-mycobacterial T cell responses through exquisite in vivo activation of vaccine-targeted dendritic cells", Eur J Immunol., (2008) p. 1247-1256, vol. 38.
Kawaoka, Y. et al., "Molecular Characterization of a New Hemagglutinin, Subtype H14, of Influenza A Virus", Virology, (1990) p. 759-767, vol. 179.
Kende, M. et al., "Ranking of prophylactic efficacy of poly(ICLC) against Rift Valley fever virus infection in mice by incremental relative risk of death", Antimicrob Agents Chemother., (1987) p. 1194-1198, vol. 31.
Knutson, K.L., et al., "Immunization of cancer patients with a HER-2/neu, HLA-A2 peptide, p369-377, results in short-lived peptide-specific immunity", Clinical Cancer Research, (2002) p. 1014-1018, vol. 8, No. 5.
Koutsky, L.A. et al., "A controlled trial of a human papillomavirus type 16 vaccine", N. Engl. J. Med., (2002) p. 1645-1651, vol. 347.
Krown, S.E. et al. "Phase I trials of poly(I,C) complexes in advanced cancer", J Biol Response Mod, (1985) p. 640-649. vol. 4.
Lambros, M.P. et al. "Liposomes, a potential immunoadjuvant and carrier for a cryptococcal vaccine", J. Pharmaceutical Sciences, (Sep. 1998), p. 1144-1148, vol. 87, No. 9.
Levy, H.B. "Historical overview of the use of polynucleotides in cancer", J Biol Response Mod., (1985) p. 475-480, vol. 4.
Levy, H.B et al., "Topical treatment of vaccinia virus infection with an interferon inducer in rabbits", J Infect Dis., (1978) p. 78-81, vol. 137.
Levy, J.K. et al., "Survey of zona pellucida antigens for immunocontraception of cats", Theriogenology, (2005) p. 1334-1341, vol. 63.
Liang, M.T. et al., "Particulate systems as adjuvants and carriers for peptide and protein antigens", Current Drug Delivery, (2006), p. 379-388, vol. 3.
Llopiz, D. et al., "Combined immunization with adjuvant molecules poly(I:C) and anti-CD40 plus a tumor antigen has potent prophylactic and therapeutic antitumor effects", Cancer Immunol Immunother, (2008) p. 19-29, vol. 57.
Mansour, M. et al. "Therapy of Established B16-F10 Melanoma Tumours by a Single Vaccination of CTL/T Helper Peptides in VacciMax®", J. Transl. Med., (Apr. 2007), p. 1-8, vol. 5, No. 20.
Mansour, M. et al. "Improved efficacy of a licensed acellular pertussis vaccine, reformulated in an adjuvant emulsion of liposomes in oil, in a murine model", Clin, and Vaccine Immunol., (Oct. 2007), p. 1381-1383, vol. 14, No. 10.
Matthews, L.J. et al., "Immunogenically fit subunit vaccine components via epitope discovery from natural peptide libraries", J. Immunol, (2002) p. 837-846, vol. 169.
Mayordomo, J.I. et al., "Bone marrow-derived dendritic cells pulsed with synthetic tumour peptides elicit protective and therapeutic antitumour immunity", Nat. Med., (1995) p. 1297-1302, vol. 1.
Millan, C.L.B. et al., "CpG DNA can induce strong Th1 humoral and cell-mediated immune responses against hepatitis B surface antigen in young mice", PNAS, (1998) p. 15553-15558, vol. 95.
Mosmann, T.R., "Role of a New Cytokine, Interleukin-10, in the Cross-Regulation of T Helper Cells", Acad. Sci. (1991) p. 337-344, vol. 628.
Muderhwa, J.M. et al., "Oil-in-water liposomal emulsions: characterization and potential use in vaccine delivery", J. Pharm. Sci. (Dec. 1999) p. 1332-1339, ISSN 0022-3549, vol. 88, No. 12.
Muttilainen, S. et al., "The Neisseria meningitidis outer membrane protein P1 produced in Bacillus subtilis and reconstituted into phospholipid vesicles elicits antibodies to native P1 epitopes", Microbial Pathogenesis, (1995) p. 423-436, vol. 18.
Nakamura, O. et al., "Phase I-II trials of poly(ICLC) in malignant brain tumor patients", J Interferon Res, (1982) p. 1-4, vol. 2.
Nash et al., "Formulation of a potential antipregnancy vaccine based on the b-subunit of human chorionic gonadotropin (b-hCG). II. Use of compounds of the muramyl dipeptide (MDP) family as adjuvants", J. Reprod. Immunol., (1985) p. 151-162, vol. 7, No. 2.
Needleman, S.B. and Wunsch, C.D. "A General Method Applicable to the Search for Similarities in the Amino Acid Seguence of Two Proteins", J. Mol. Biol., (1970) p. 443-453, vol. 48.
Öhlschläger, P. et al., "Human Papillomavirus Type 16 LI Capsomeres Induce L1-Specific Cytotoxic T Lymphocytes and Tumor Regression in C57BL/6 Mice", Journal of Virology (2003) p. 4635-4645, vol. 77.
Padalko, E. et al., "The interferon inducer ampligen [poly(1)-poly(C12U)] markedly protects mice against coxsackie B3 virus-induced myocarditis", Antimicrob Agents Chemother, (2004) p. 264-274, vol. 48.
Padilla-Paz, L.A., "Human papillomavirus vaccine: history, immunology, current status, and future prospects", Clin. Obstet. Gynecol., (2005) p. 226-240, vol. 48.
Parkin, D.M. et al., "Estimating the world cancer burden: Globocan 2000", Int. J. Cancer, (2001) p. 153-156, vol. 94.
Parrado et al., "The domain organization of streptokinase: Nuclear magnetic resonance, circular dichroism, and functional characterization of proteolytic fragments", Protein Sci., (1996) p. 693-704, vol. 5.
Pilon-Thomas, S. et al., "Immunostimulatory Effects of CpG-ODN Upon Dendritic Cell-Based Immunotherapy in a Murine Melanoma Model", Journal Immunotherapy, (2006) p. 381-387, vol. 29, No. 4.
Poast, J. et al., "Poly I:CLC induction of the interferon system in mice: an initial study of four detection methods", J Interferon Cytokine Res, (2002) p. 1035-1040, vol. 22.
Puri, S.K. et al., "Poly ICLC inhibits Plasmodium cynomolgi B malaria infection in rhesus monkeys", J Interferon Cytokine Res., (1996) p. 49-52, vol. 16.
Pye, D. et al., "Selection of an adjuvant for vaccination with the malaria antigen, MSA-2", Vaccine, (1997) p. 1017-1023, vol. 15, No. 9.
Rao, M. et al., "Delivery of lipids and liposomal proteins to the cytoplasm and Golgi of antigen-presenting cells", Adv. Drug Deliv. Rev., (2000) p. 171-188, vol. 41.
Rao, M. et al., "Intracellular processing of liposome-encapsulated antigens by macrophages depends upon the antigen", Infect. Immun., (1995) p. 2396-2402, vol. 63.
Reis E Sousa, C., "Toll-like receptors and dendritic cells: for whom the bug tolls", Semin. Immunol., (2004) p. 27-34, vol. 16.
Riedl, K. et al., "The novel adjuvant IC31® strongly improves influenza vaccine-specific cellular and humoral immune responses in young adult and aged mice", Vaccine, (2008) p. 3461-3468, vol. 26.
Roberge, J.Y. et al., "A Strategy for a Convergent Synthesis of N-Linked Glycopeptides on a Solid Support", Science, (1995) p. 202-204, vol. 269.
Salazar, A.M. et al., "Long-term treatment of malignant gliomas with intramuscularly administered poluyinosinic-polycytidylic acid stabilized with polylysine and carboxymethylcellulose: an open pilot study", Neurosurgery, (1996) p. 1096-103 and discussion 1103-1104, vol. 38.
Salem, M.L. et al., "The adjuvant effects of the toll-like receptor 3 ligand polyinosinic-cytidylic acid poly (I:C) on antigen-specific

(56) References Cited

OTHER PUBLICATIONS

CD8+ T cell responses are partially dependent on NK cells with the induction of a beneficial cytokine milieu", Vaccine, (2006) p. 5119-5132, vol. 24.
Salem, M.L. et al., "Defining the antigen-specific T-cell response to vaccination and poly(I:C)/TLR3 signaling: evidence of enhanced primary and memory CD8 T-cell responses and antitumor immunity", J Immunother, (2005) p. 220-228, vol. 28.
Sarma, P.S. et al., "Virus-induced sarcoma of mice: inhibition by a synthetic polyribonucleotide complex", Proc Natl Acad Sci USA, (1969) p. 1046-1051, vol. 62.
Schellack, C. et al., "IC31, a novel adjuvant signaling via TLR9, induces potent cellular and humoral immune responses", Vaccine, (2006) p. 5461-5472, vol. 24.
Schijns, V.E., "Immunological concepts of vaccine adjuvant activity", Current Opinion in Immunology, (2000) p. 456-463, vol. 12.
Schreckenberger, C. et al., "Vaccination strategies for the treatment and prevention of cervical cancer", Curr. Opin. Oncol., (2004) p. 485-491, vol. 16.
Schueler-Furman, O et al., "Knowledge-based structure prediction of MHC class I bound peptides: a study of 23 complexes", Folding & Design, (1998) p. 549-564, vol. 3.
Shedlock, D.J. et al., "Requirement for CD4 T cell help in generating functional CD8 T cell memory", Science, (2003) p. 337-339, vol. 300.
Sloat, B.R. et al., "Nasal immunization with the mixture of PA63, LF, and a PGA conjugate induced strong antibody responses against all three antigens", FEMS Immunol Med Microbiol, (2008) p. 169-179, vol. 5.
Smith, K.M., et al., "In Vivo Generated Th1 Cells Can Migrate to B Cell Follicles to Support B Cell Responses", J. Immunol., (2004) p. 1640-1646, vol. 173.
Smith, T.F. and Waterman, M.S. "Comparison of Biosequences", Adv. Appl. Math, (1981) p. 482-489, vol. 2.
Sparwasser, T. et al., "Bacterial DNA and immunostimulatory CpG oligonucleotides trigger maturation and activation of murine dendritic cells", Eur. J. Immunol., (1998) p. 2045-2054, vol. 28.
Slephen, E.L. et al., "Effect a nuclease-resistant derivative of polyriboinosinic-polyribocytidylic acid complex on yellow fever in rhesus monkeys (*Macaca mulatta*)", J Infect Dis, (1977) p. 122-126, vol. 136.
Stephen, E.L. et al., "Swine influenza virus vaccine: potentiation of antibody responses in rhesus monkeys", Science, (1977) p. 1289-1290, vol. 197.
Stern, P.L., "Immune control of human papillomavirus (HPV) associated anogenital disease and potential for vaccination", J. Clin. Virol., (2005) 32 Suppl. 1:S72-81.
Takeuchi, O. et al., "Cutting edge: role of toll-like receptor 1 in mediating immune response to microbial lipoproteins", The Journal of Immunology (2002) p. 10-14, ISSN 0022-1767, vol. 169.
Talmadge, J.E. et al., "Immunotherapeutic potential in murine tumor models of polyinosinic-polycytidylic acid and poly-L-lysine solubilized by carboxymethylcellulose", Cancer Res., (1985) p. 1066-1072, vol. 45.
Teuten, A.J. et al., "Characterization of structural and folding properties of streptokinase by n.m.r. spectroscopy", Biochem. J., (1993) p. 313-319, vol. 290.
The National Wildlife Research Center, "Porcine Zona Pellucida Immunocontraception in Mammals," (Oct. 9, 2007), accessed online: <www.a-phis.usda.gov/ws/nwrc/pzp.htm>.
Tillman, B.W. et al., "Adenoviral vectors targeted to CD40 enhance the efficacy of dendritic cell-based vaccination against human papillomavirus 16-induced tumor cells in a murine model", Cancer Res., (2000) p. 5456-5463, vol. 60.
Tiwari, S. et al., "Gel core liposomes: an advanced carrier for improved vaccine delivery", J. Microencapsul., (Feb. 2009), p. 75-82, vol. 26, No. 1 (Abstract only).
Torrèns, I. et al., "A mutant streptokinase lacking the C-terminal 42 amino acids is less immunogenic", Immunology Letters, (1999) p. 213-218, vol. 70.
Torrèns, I. et al., "Immunotherapy with CTL peptide and VSSP eradicated established human papillomavirus (HPV) type 16 E7-expressing tumors", Vaccine, (2005) p. 5768-5774, vol. 23.
Trumpfheller, C. et al., "The microbial mimic poly IC induces durable and protective CD4+ T cell immunity together with a dendritic cell targeted vaccine", Proc Natl Acad Sci USA, (2008) p. 2574-2579, vol. 105.
Tsukui, T. et al., "Interleukin 2 production in vitro by peripheral lymphocytes in response to human papillomavirus-derived peptides: correlation with cervical pathology", Cancer Res., (1996) p. 3967-3974, vol. 56.
Van Oosterhout, A.J.M. et al., "Th1/Th2 paradigm: not seeing the forest for the trees?", Eur. Respir. J., (2005) p. 591-593, vol. 25.
Velders, M.P. et al., "Eradication of established tumors by vaccination with Venezuelan equine encephalitis virus replicon particles delivering human papillomavirus 16 E7 RNA", Cancer Res., (2001) p. 7861-7867, vol. 61.
Walboomers, J.M. et al., "Human papillomavirus is a necessary cause of invasive cervical cancer worldwide", J. Pathol., (1999) p. 12-19, vol. 189.
Wang, J.-C. et al., "Cutting edge: CD4+ T cell help can be essential for primary CD8$^+$T cell responses in vivo", J. Immunol., (2003) p. 6339-6343, vol. 171.
Weeratna, R.D. et al., "CpG DNA induces stronger immune responses with less toxicity than other adjuvants", Vaccine (2000) p. 1755-1762, vol. 18.
Wiesmuller, K.H. et al.., "Peptide vaccines and peptide libraries", Biol. Chem., (Apr. 2001), p. 571-579, vol. 382.
Wilcox, R.A. et al., "Provision of antigen and CD137 signaling breaks immunological ignorance, promoting regression of poorly immunogenic tumors", J. Clin. Invest., (2002) p. 651-659, vol. 109.
Willard et al., Pregnancy detection and the effects of age, body weight, and previous reproductive performance on pregnancy status and weaning rates of farmed fallow deer (*Dama dama*), J. Animal Science, (1999) p. 32-38, vol. 77.
Yoneyama, M. et al., "The RNA helicase RIG-I has an essential function in double-stranded RNA-induced innate antiviral responses", Nat Immunol, (2004) p. 730-737, vol. 5.
Zaks, K. et al., "Efficient immunization and cross-priming by vaccine adjuvants containing TLR3 or TLR9 agonists complexed to cationic liposomes", J. Immunol., (2006) p. 7335-7345, vol. 176.
Zauner, W. et al., "Defined synthetic vaccines", Biol. Chem., (2001) p. 581-595, vol. 382.
Zhu, X. et al. "Toll like receptor-3 ligand poly-ICLC promotes the efficacy of peripheral vaccinations with tumor antigen-derived peptide epitopes in murine CNS tumor models", J Transl. Med., (2007) vol. 5:10.
Zinkernagel, R.M., "On cross-priming of MHC class I-specific CTL: rule or exception?", Eur. J. Immunol., (2002) p. 2385-2392, vol. 32.
Zur Hausen, H., "Papillomaviruses and cancer: from basic studies to clinical application", Nat. Rev. Cancer, (2002) p. 342-350, vol. 2.
International Search Report dated Dec. 19, 2008, International Application No. PCT/CA2008/001747.
Seniors et al., "Stability of small unilamellar liposomes in serum and clearance from the circulation: The effect of the phospholipid and cholesterol components" Life Sciences, 1982, vol. 30, issue 24, pp. 2123-2136.
Marciani, "Vaccine Adjuvants: role and mechanism of action in vaccine immunogenicity" DDT, Oct. 2003, vol. 8 No. 2, pp. 934-943.
Joseph et al., "Liposomal immunostimulatory DNA sequence (ISS-ODN): an efficient parenteral and mucosal adjuvant for influenza and hepatitis B vaccines" Vaccine, 2002, 20, pp. 3342-3354.
Aichinger et al., "Unique membrane-interacting properties of the immunostimulatory cationic peptide KLKL5KLK (KLK)" Cell Biology International, 2008, 32, pp. 1449-1458.
Tafaghodi et al., "Nasal immunization studies using liposomes loaded with tetanus toxoid and CpG—ODN" Eur. J. Pham. Biopharm., 2006, 64, pp. 138-145.
Le Bon et al., "Type I Interferons Potently Enhance Humoral Immunity and can Promote Isotype Switching by Stimulating Dendritic Cells in Vivo" Immunity, Apr. 2001, 14, pp. 461-470.

(56) References Cited

OTHER PUBLICATIONS

Storni et al., "Immunity in response to particulate antigen-delivery systems" Advanced Drug Delivery Reviev, 2005, 57, pp. 333-355.
Stanicova et al., "Amantadine: an antiviral and antiparkinsonian agent" Vet. Med.—Czech, 2001, 9-10, pp. 244-256.
Davis et al., "Liposomes as adjuvants with immunopurified tetanus toxoid: influence of liposomal characteristics" Immunology, 1987, 61, pp. 229-234.
International Search Report and Written Opinion dated Sep. 2, 2009, International Application No. PCT/CA2009/000692.
PCT/CA2009/000692 International Preliminary Report on Patentability dated Dec. 6, 2010.
Sabena Uddowla et al., "Effect of adjuvants and route of immunizations on the immune response to recombinant plague antigens", Vaccine, vol. 25, No. 47, 2007, pp. 7984-7993.
Hearing Notice regarding related Indian application No. 411/MUMNP/2010, dated Sep. 30, 2016 (3pgs).
Examination Search Report from Canadian Patent Database 2,700,808 dated Apr. 22, 2016 Use of Liposomes in a Carrier Composing a Continuous Hydrophobic Phase for Delivery of Polynucleotides in Vivo.
Sigma-Aldridch Product Information Freund's Adjuvant Complete and Incomplete Catalog Nos. F5881 and F5506.
Examination Report regarding Canadian counterpart application No. 2,700,808 , dated Feb. 9, 2015 (10 pgs).
Wu et al., "Topical transfection using plasmid DNA in a water-in-oil nanoemuision", Int. J. Pharm., vol. 221, pp. 23-34, Jun. 19, 2001 (12 pgs).
Chung et al., "Oil Components Modulate Physical Characteristics and Function of the Natural Oil Emulsions a Drug or Gene Delivery System" Journal Cont Rel, 71, 339-350, 2001.
Choi et al., "Low Toxicity of Cationic Lipid-Based Emulsion for Gene Transfer", Biomaterials, 25:5893-5903, 2004.
Zhang et al., "A Novel DNA Vaccine Based on Ubiquitin-Proteasome Pathway Targeting 'Self'-Antigens Expressed in Melanoma/Melanocyte", Gene Therapy, 2005, vol. 12, pp. 1049-1057.
Supplementary European Search Report for related application No. EP 08 80 0369 dated Apr. 20, 2012.
Karkada et al., "A liposome-based platform, VacciMax, and its modified water-free platform DepoVax enhance efficacy of in vivo nucleic acid delivery", Vaccine, vol. 28, No. 38, 2010, pp. 6176-6182.
Meyer, Martin et al. "Recent developments in the application of plasmid DNA-based vectors and small interfering RNA therapeutics for cancer", Human Gene Therapy, vol. 17, No. 11, Nov. 2006, pp. 1062-1076.
International Search Report and Written Opinion issued in International Application No. PCT/CA2008/001678 dated Dec. 30, 2008.
"Assessment and Harmonization of Laboratory Diagnostic Procedures Related to Human Papillomavirus Vaccine Research and Development," Technical Meeting: Department of Vaccines and Biologicais, Heidelberg (2001).
Conejero-Lara et al., "Thermal Stability of the Three Domains of Streptokinase Studied by Circular Dichroism and Nuclear Magnetic Resonance," Protein Science, vol. 5, pp. 2583-2591 (1996).
DeLeo, "p53-Based Immunotherapy of Cancer," Critical Reviews in Immunology, 1998, vol. 18, pp. 29-35.
Dockrell and Kinghorn, "Imiquimod and resiquimod as novel immunomodulators," Journal of Antimicrobial Chemotherapy 48: 751-755 (2001).
European Search Report for European Patent Application No. EP 06790800.4 (dated Nov. 13, 2008).
Rechtsteiner et al., "Cutting Edge: Priming of CTL by transcutaneous peptide immunization with imiqulmod," Journal of Immunology 174: 2476-2480 (2005).
Richards et al., "Liposome-stabilized Oil-In-Water Emulsions as Adjuvants: Increased Emulsion Stability Promotes Induction of Cytotoxic T Lymphocytes Against an HIV Envelope Antigen," Immunology and Cell Biology, 2004, vol. 82, pp. 531-538.
Sacco et al., "Effect of Varying Dosages and Adjuvants on Antibody Response in Squirrel Monkeys (*Saimiri sciureus*) Immunized with the Porcine Zona Pelludica Mr=55,000 Glycoprotein (ZP3)," Am. J. Reprod. Immunol. 21 :1-8 (1989).
Siskind et al., "Cell Selection by Antigen in the Immune Response," Adv. Immunol. 10:1-50 (1969).
Vierboom et al., "p53: A Target for T-Cell Mediated Immunotherapy," Peptide-Based Cancer Vaccines, W.M. Kast, Ed. Landes Bioscience, Georgetown, p. 40-55 (2000).
Witt et al., "Phase I trial of an oral immunomodulator and interferon inducer in cancer patients," Cancer Research 53: 5176-5180 (1993).
International Search Report for PCT/CA2006/001640 (dated Jan. 29, 2007).
Office Action for European Patent Application No. 06 790 800.4, dated Oct. 19, 2009.
Ninomiya et al., "Intranasal administration of a synthetic peptide vaccine encapsulated in liposome together with an anti-CD40 antibody induces protective immunity against influenza A virus in mice," Vaccine. 20(25-26): 3123-9 (2002).
Evans et al., "Antigen Processing Defects in Cervical Carcinomas Limit the Presentation of a CTL Epitope from Human Papillomavirus 16 E6", The Journal of Immunology, 2001, vol. 167, pp. 5420-5428.
Ringleb (Dissertation 2004).
Supplementary EP Search Report for related Application No. EP 08 80 0418 dated Jun. 21, 2012.
Stone, "Newcastle Disease Oil Emulsion Vaccines Prepared with Animal, Vegetable, and Synthetic Oils", Avian Diseases 41:591-597, 1997.
First Office Action regarding Canadian companion case 2,700,828, dated Oct. 2, 2014 (4 pages).
Aucouturier et al., "Montanide ISA 720 and 51: a new generation of water in oil emulsions as adjuvants for human vaccines", Expert Rev. Vaccines, 2002, vol. 1, No. 1, pp. 111-118.
Office Action issued in U.S. Appl. No. 15/290,567 dated Oct. 2, 2017. (7 pages).
Office Action issued in U.S. Appl. No. 15/290,567 dated May 18, 2018. (15 pages).
Office Action regarding U.S. Appl. No. 14/674,063, dated Nov. 9, 2016 (29 Pages).
U.S. Office Action for Related U.S. Appl. No. 12/992,512 dated Oct. 18, 2012.
Office Action for U.S. Appl. No. 12/679,875, dated Nov. 20, 2012 (11 pages).
Final Office Action for U.S. Appl. No. 12/083,209, dated Oct. 27, 2015 (8 pages).
Office Action issued in U.S. Appl. No. 15/897,025 dated Apr. 10, 2018.
Biotechnological Drug Formulations—Basics and Applications.
Krieg, "Development of TLR9 agonists for cancer therapy", The Journal of Clinical Investigation, 2007, vol. 117, No. 5, pp. 1184-1194.

* cited by examiner

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 1

Ile Tyr Ser Thr Val Ala Ser Ser Leu
1               5


<210> SEQ ID NO 2
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 2

Phe Asn Asn Phe Thr Val Ser Phe Trp Leu Arg Val Pro Lys Val Ser
1               5                   10                  15

Ala Ser His Leu Glu
            20


<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Arg Ala His Tyr Asn Ile Val Thr Phe
1               5
```

COMPOSITIONS COMPRISING LIPOSOMES, AN ANTIGEN, A POLYNUCLEOTIDE AND A CARRIER COMPRISING A CONTINUOUS PHASE OF A HYDROPHOBIC SUBSTANCE

CROSS-REFERENCE TO RELATED APPLICATIONS

The present application is a continuation of U.S. patent application Ser. No. 12/992,512, filed Nov. 12, 2010, which is a National Stage Entry of International Application No. PCT/CA2009/000692, filed May 22, 2009, which claims the benefit of and priority from U.S. Provisional Patent Application No. 61/059,043, filed Jun. 5, 2008, all of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 12, 2013, is named 249979_000051_SL.txt, and is 1.15 bytes in size.

FIELD OF THE INVENTION

The present application relates compositions comprising liposomes, an antigen, a polyI:C polynucleotide and a carrier comprising a continuous phase of a hydrophobic substance, and their use.

BACKGROUND OF THE INVENTION

Conventional vaccines may comprise an antigen, an adjuvant and a pharmaceutically acceptable carrier. It is known that a polyI:C polynucleotide may be useful as an adjuvant. It is also known that liposomes may be useful in vaccine compositions (see Applicants' issued U.S. Pat. No. 6,793,923). However, to Applicants' knowledge, the art does not teach or suggest combining an antigen, a polyI:C polynucleotide, liposomes and a hydrophobic carrier in a vaccine composition.

SUMMARY OF THE INVENTION

Applicants have now discovered that a composition comprising an antigen, a polyI:C polynucleotide, liposomes and a carrier comprising a continuous phase of a hydrophobic substance may provide surprisingly higher antibody titers and a higher percentage of activated or memory CD8+ T cells than either conventional vaccine compositions containing polyI:C polynucleotides in an aqueous carrier, or compositions comprising liposomes, a hydrophobic carrier and an alum adjuvant.

Accordingly, in one aspect, the invention provides a composition comprising: (a) an antigen; (b) liposomes; (c) a polyI:C polynucleotide; and (d) a carrier comprising a continuous phase of a hydrophobic substance.

In another aspect, the invention provides a method for making a composition, said method comprising combining, in any order: (a) an antigen; (b) liposomes; (c) a polyI:C polynucleotide; and (d) a carrier comprising a continuous phase of a hydrophobic substance. In an embodiment, the antigen is encapsulated in the liposomes. In an embodiment, the polyI:C polynucleotide is encapsulated in the liposomes.

In another aspect, the invention provides a composition prepared according to the methods described above.

In another aspect, the invention provides a method comprising administering a composition as described above to a subject. In an embodiment, the method is a method for inducing an antibody response or cell-mediated immune response to the antigen in the subject.

Other aspects and features of the present invention will become apparent to those of ordinary skill in the art upon review of the following description of specific embodiments of the invention in conjunction with the accompanying figures.

BRIEF DESCRIPTION OF THE FIGURES

In the figures, which illustrate embodiments of the invention by way of example only:

FIG. 11 shows the average tumor volume calculated for each group+/−SEM. P values were calculated for Group 1 and Group 2 using Students' T test, *p=<0.1, **p=<0.05.

FIG. 12 shows the average tumor volume calculated for each group+/−SEM. P values were calculated for Group 2 and Group 3 using Students' T test, *p=<0.05.

DETAILED DESCRIPTION

Figure 1:
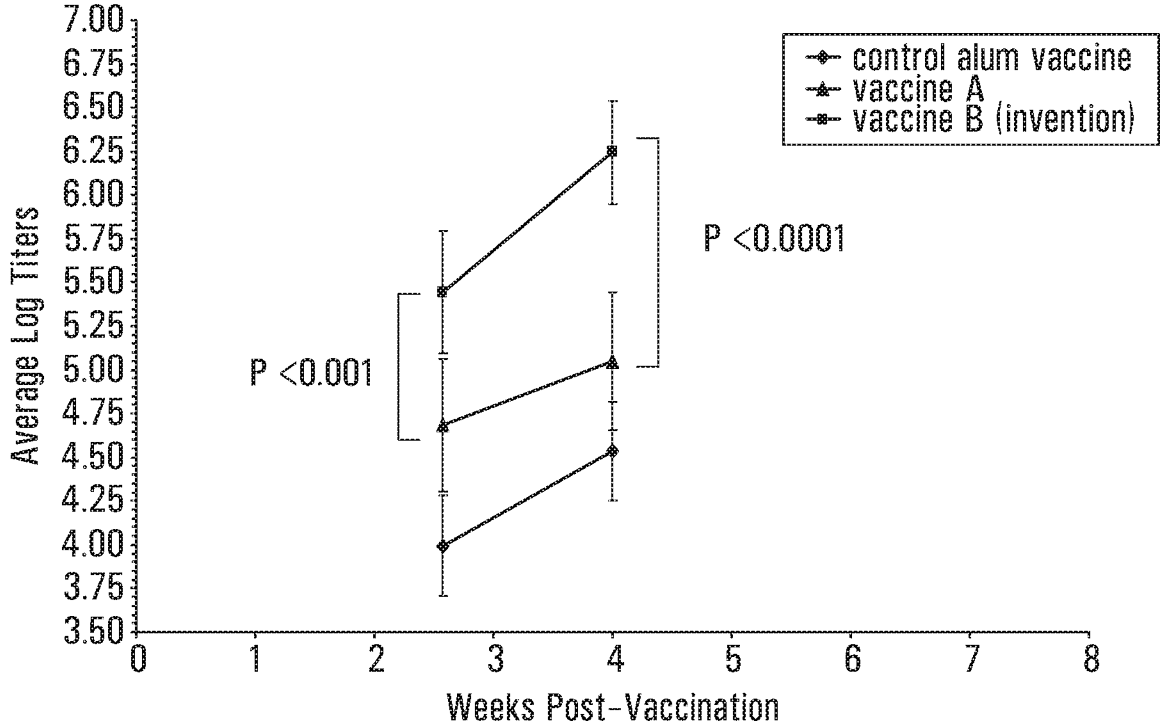
FIG. 1 is a graph showing the results of vaccination of three groups of mice (n=9 or 10) as follows: Group 1 mice were vaccinated with 1 microgram rHA and 4 micrograms polyI:C in a 30 microliter dose formulated as a liposome/polyI:C/hydrophobic carrier vaccine (Vaccine B, the invention). Group 2 mice were treated with Vaccine A comprising 1 microgram rHA and 60 micrograms alum in a 30 microliter dose of liposome/alum/hydrophobic carrier formulation. Group 3 mice were vaccinated with 1 microgram rHA and 60 micrograms alum per 30 microliter dose of control alum vaccine. Humoral immune responses were measured by ELISA as described herein. For each treatment group, the log 10 values of the endpoint antibody titers were averaged and standard deviations calculated for each time point. P values were calculated using the student T test.
Figure 2:
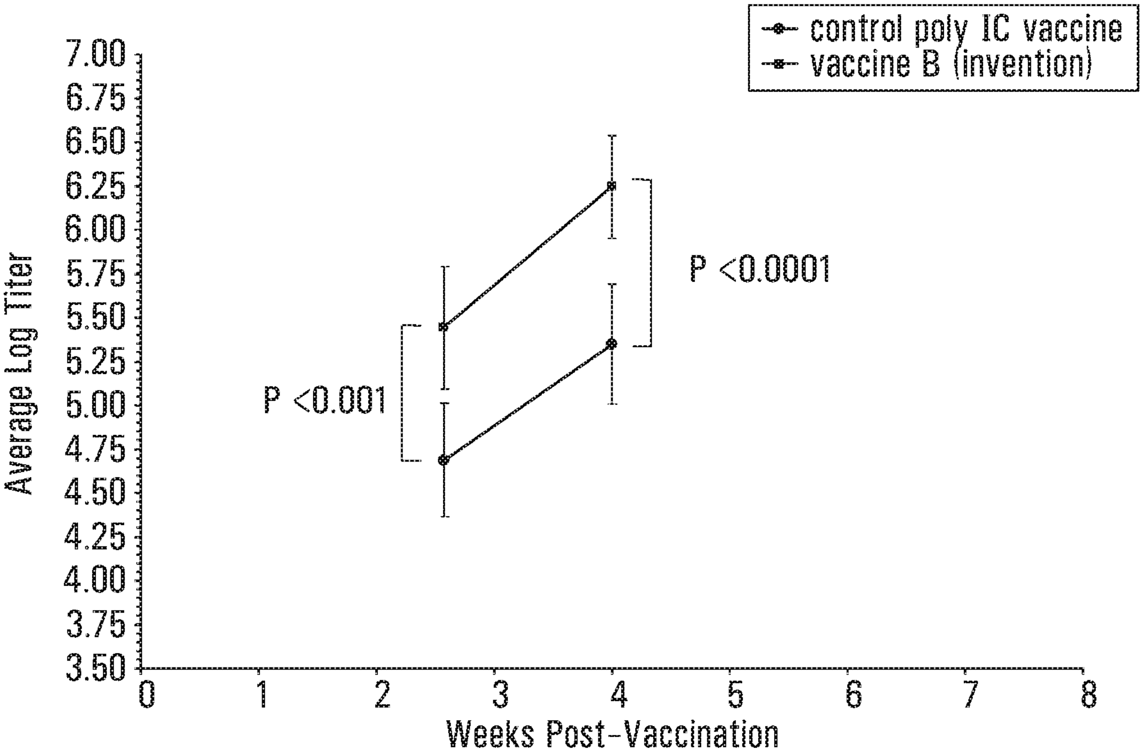
FIG. 2 is a graph showing the results of vaccination of two groups of mice (n=9 or 10) as follows: Group 1 mice were vaccinated with 1 microgram rHA and 4 micrograms polyI:C in a 30 microliter dose formulated as a liposome/polyI:C/hydrophobic carrier vaccine (Vaccine B, the invention). Group 2 mice were treated with 1 microgram rHA and 4 micrograms polyI:C per 30 microliter dose of control polyI:C vaccine. Humoral immune responses were measured by ELISA as described herein. For each treatment group, the log 10 values of the endpoint antibody titers were averaged and standard deviations calculated for each time point. P values were calculated using the student T test.
Figure 3:
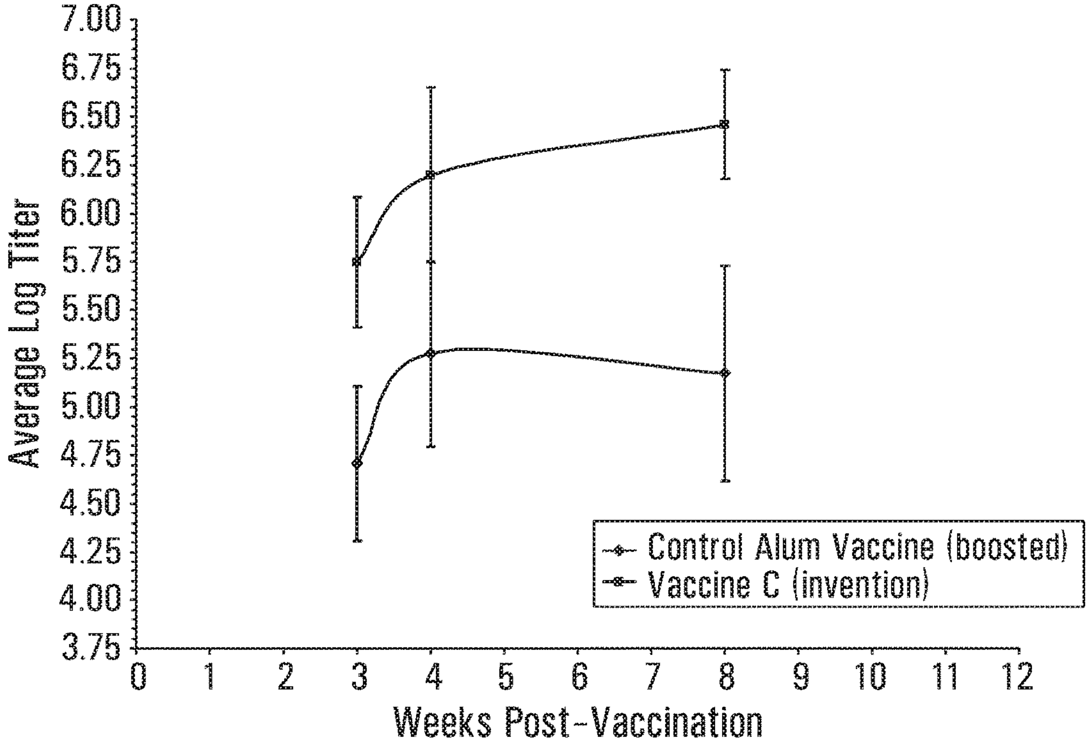
FIG. 3 is a graph showing the results of vaccination of two groups of mice (n=8 or 9) as follows: Group 1 mice were vaccinated with a single dose of 1 microgram rHA and 10 micrograms polyI:C in a 50 microliter dose formulated as a lyophilized liposome/polyI:C/hydrophobic carrier vaccine (Vaccine C, the invention). Group 2 mice were treated with 1 microgram rHA and 100 micrograms alum per 50 microliter dose of control alum vaccine; mice were boosted 21 days post-vaccination. Humoral immune responses were measured by ELISA as described herein. For each treatment group, the log 10 values of the endpoint antibody titers were averaged and standard deviations calculated for each time point.
Figure 4:
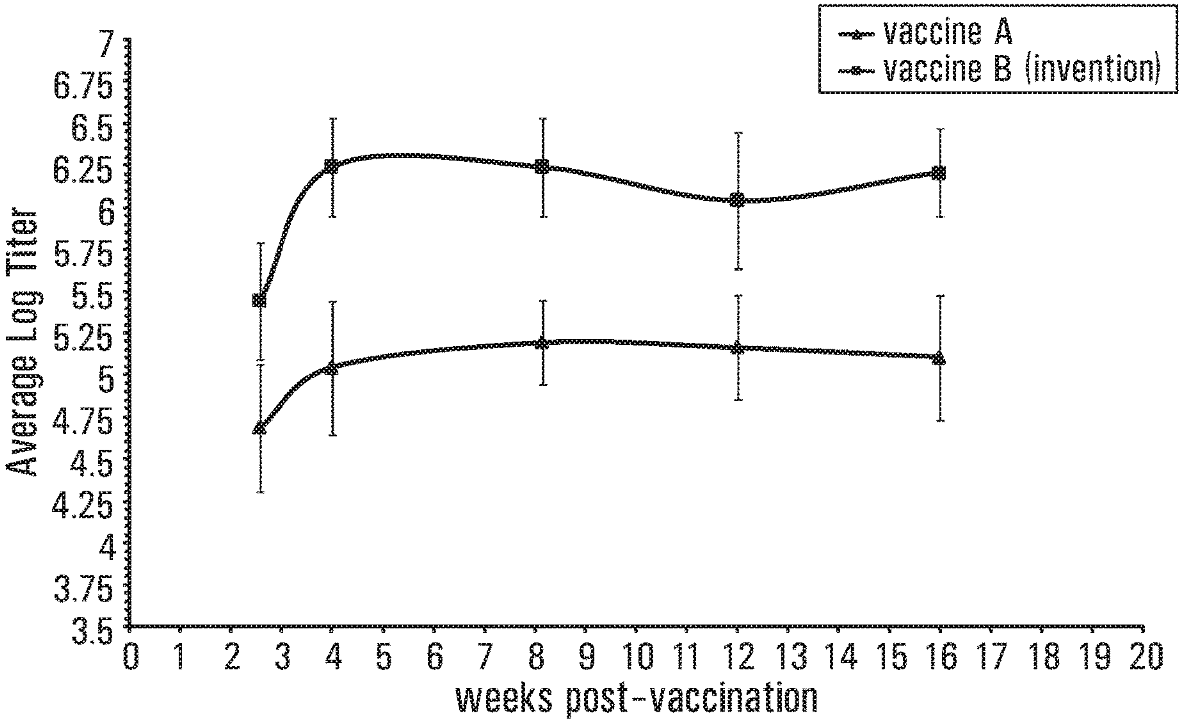
FIG. 4. Enhanced anti-rHA antibody responses following vaccination with rHA antigen formulated in a liposome/polyI:C/oil carrier vaccine. Two groups of mice (n=9 or 10) were vaccinated as follows: Group 1 mice were vaccinated with 1 microgram rHA and 4 micrograms polyI:C in a 30 microliter dose formulated as a liposome/polyI:C/hydrophobic carrier vaccine (Vaccine B, the invention). Group 2 mice were treated with Vaccine A, 1 microgram rHA and 60 micrograms alum in a 30 microliter dose of liposome/alum/hydrophobic carrier formulation. Humoral immune responses were measured by ELISA as described herein. For each treatment group, the log 10 values of the endpoint antibody titers were averaged and standard deviations calculated for each time point. P values were calculated using the student T test.
Figure 5:
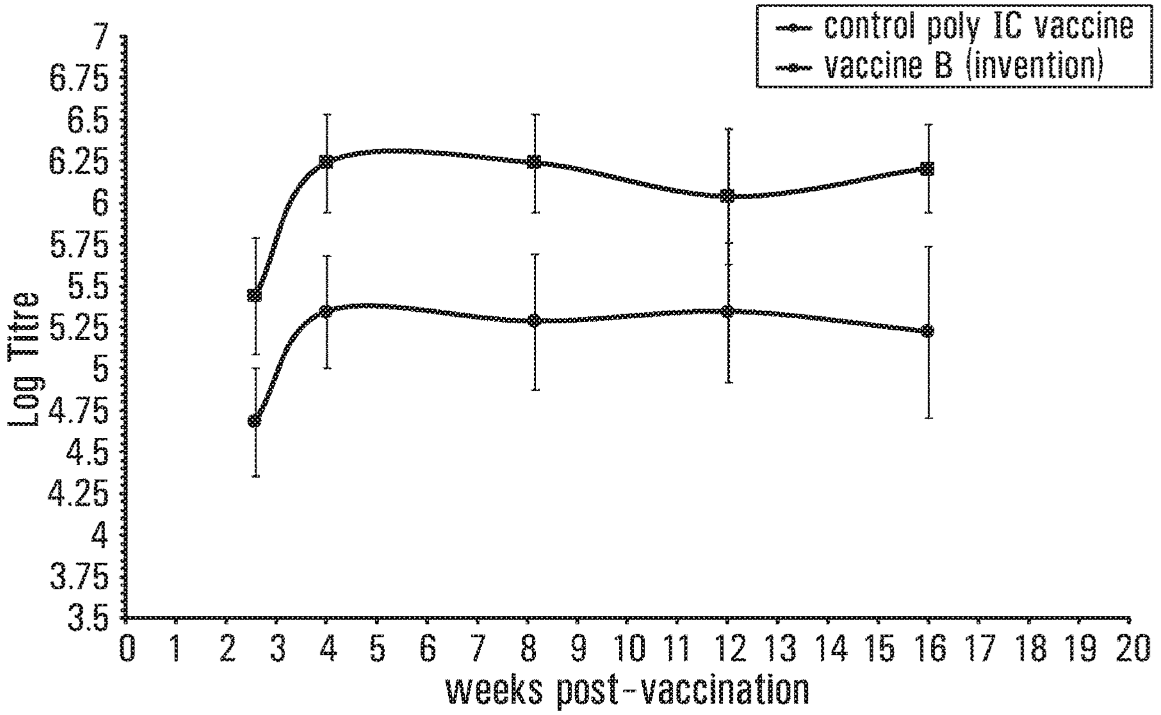
FIG. 5. Enhanced anti-rHA antibody responses following vaccination with rHA antigen formulated in a liposome/polyI:C/oil carrier vaccine. Two groups of mice (n=9 or 10) were vaccinated as follows: Group 1 mice were vaccinated with 1 microgram rHA and 4 micrograms polyI:C in a 30 microliter dose formulated as a liposome/polyI:C/hydrophobic carrier vaccine (Vaccine B, the invention). Group 2 mice were treated with 1 microgram rHA and 4 micrograms polyI:C per 30 microliter dose of control polyI:C vaccine. Humoral immune responses were measured by ELISA as described herein. For each treatment group, the log 10 values of the endpoint antibody titers were averaged and standard deviations calculated for each time point. P values were calculated using the student T test.
Figure 6:
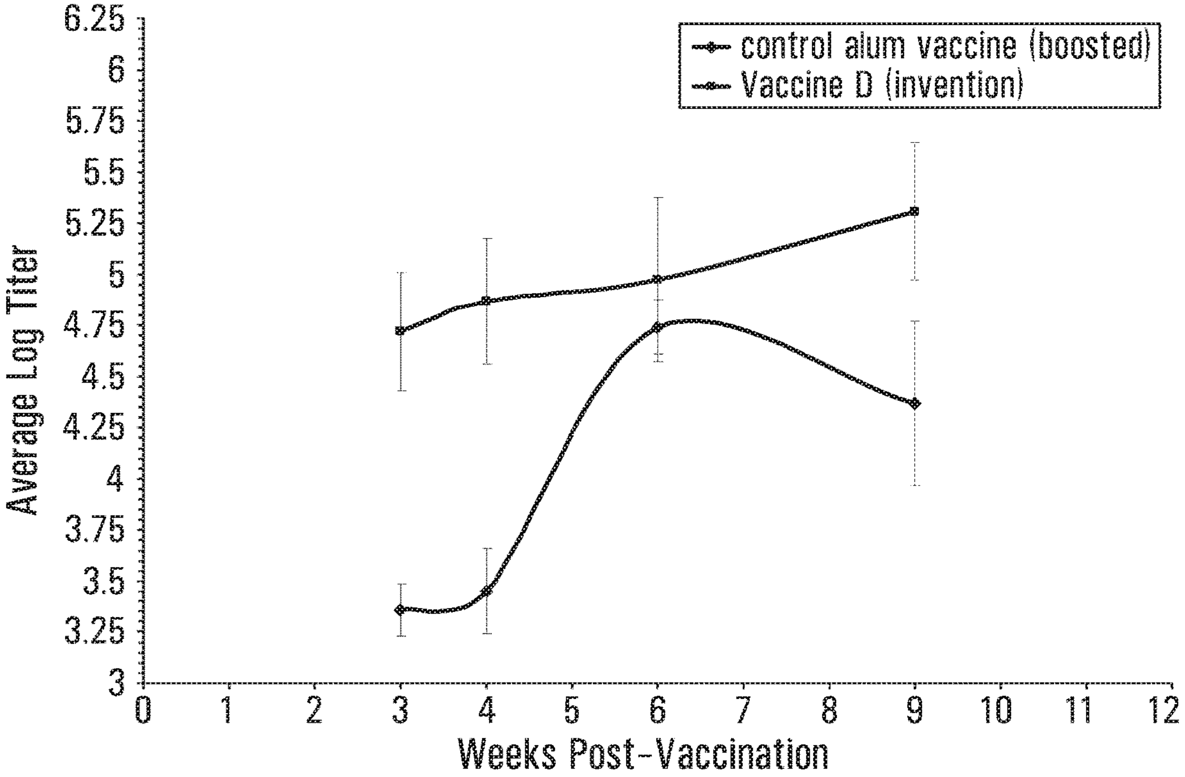
FIG. 6. Enhanced anti-rHA antibody responses following vaccination with rHA antigen formulated in a lyophilized liposome/polyI:C/oil carrier vaccine. Two groups of mice (n=9 or 10) were immunized as follows: Group 1 mice were vaccinated with a single dose of 1.5 micrograms rHA and 12.5 micrograms polyI:C in a 50 microliter dose formulated as a lyophilized liposome/polyI:C/hydrophobic carrier vaccine (Vaccine D, the invention). Group 2 mice were treated with 1.5 micrograms rHA and 100 micrograms alum per 50 microliter dose of control alum vaccine; mice were boosted 28 days (week 4) post-vaccination. Humoral immune responses were measured by ELISA as described herein. For each treatment group, the log 10 values of the endpoint antibody titers were averaged and standard deviations calculated for each time point. P values were calculated using the Student T test.
Figure 7:
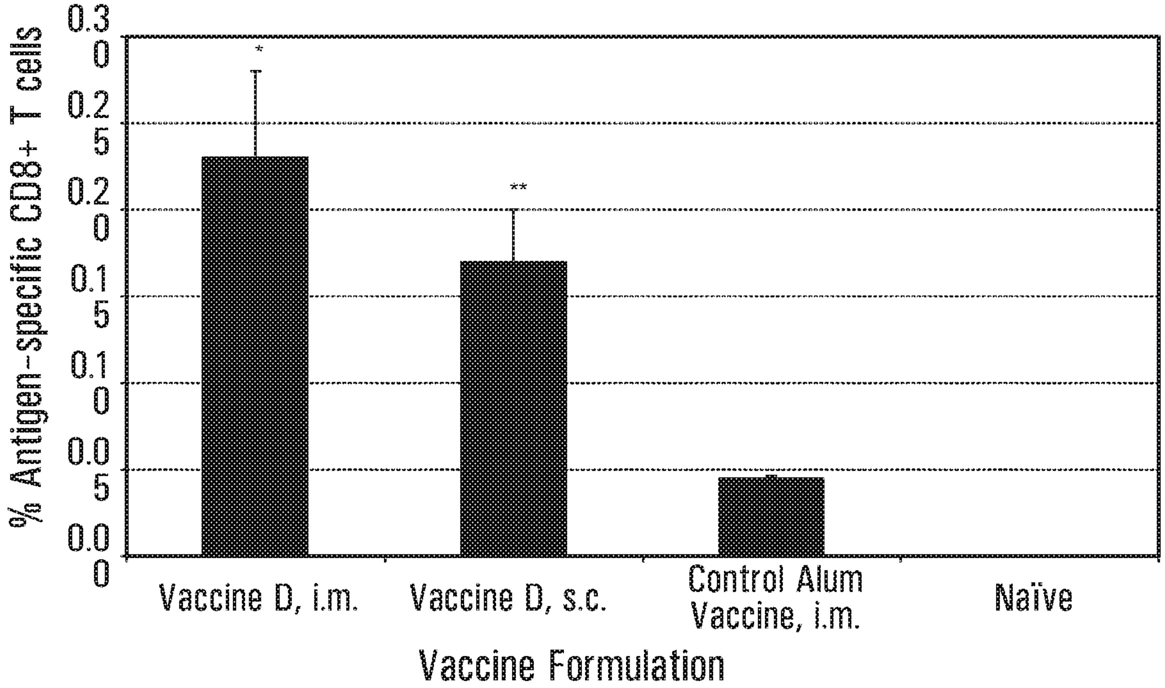
FIG. 7. Number of antigen-specific CD8 cells within a CD8-positive T cell population following vaccination. Three groups of BALB/c mice (n=4) were vaccinated as follows: Group 1 mice were vaccinated with 1.5 micrograms of rHA and 12.5 micrograms of RNA-based polyI:C adjuvant in a 50 microliter dose formulated as lyophilized liposome/polyI:C/hydrophobic carrier vaccine (Vaccine D, invention) intramuscularly. Group 2 mice were vaccinated with 50 microliters of Vaccine D subcutaneously. Group 3 mice were vaccinated with 1.5 micrograms of rHA and 100 micrograms of Imject Alum adjuvant in 50 microliters of 50 millimolar phosphate buffer (pH 7.0) intramuscularly. All vaccines were given once without boosting. Antigen-specific CD8+ T cells were detected twenty-two days after vaccination in the splenocytes of animals using tri-colour flow cytometric analysis. Cells were stained with anti-CD8β-APC, anti-CD19-FITC and a PE-pentamer specific for H2-Dd bearing the immunodominant epitope of rHA, 19L. Results are expressed as average percentage of pentamer positive cells in a population of CD8β-positive/CD19-negative cell population, +/−standard deviation. The background staining detected in the splenocytes isolated from naïve cells was subtracted. *p=<0.025, **p=<0.005, as compared to Group 3.
Figure 8:
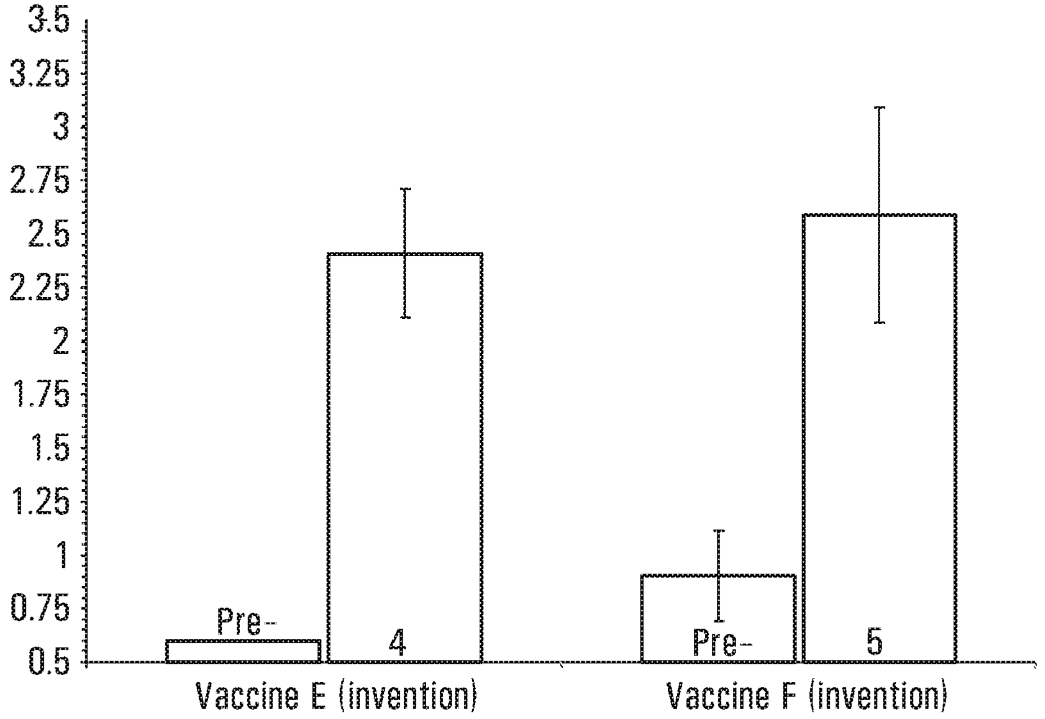
FIG. 8. Hemagglutination inhibition (HAI) titers following a single vaccination against rHA formulated in the invention. One group of mice and one group of rabbits (n=5) were vaccinated as follows: The group of mice were vaccinated with 0.5 micrograms rHA and 12 micrograms polyI:C in a 50 microliter dose formulated as a lyophilized liposome/polyI:C/hydrophobic carrier vaccine (Vaccine E, the invention). The group of rabbits were treated with Vaccine F (the invention), 2 microgram rHA and 50 micrograms polyI:C in a 200 microliter dose of lyophilized liposome/polyI:C/hydrophobic carrier formulation. Humoral immune responses were measured by hemagglutination inhibition assay, as described herein; before vaccination (pre-vaccination) and at 4 (rabbits) or 5 (mice) weeks afterwards. For each animal group, the log 10 values of the HAI titers were averaged and standard deviation calculated.
Figure 9:
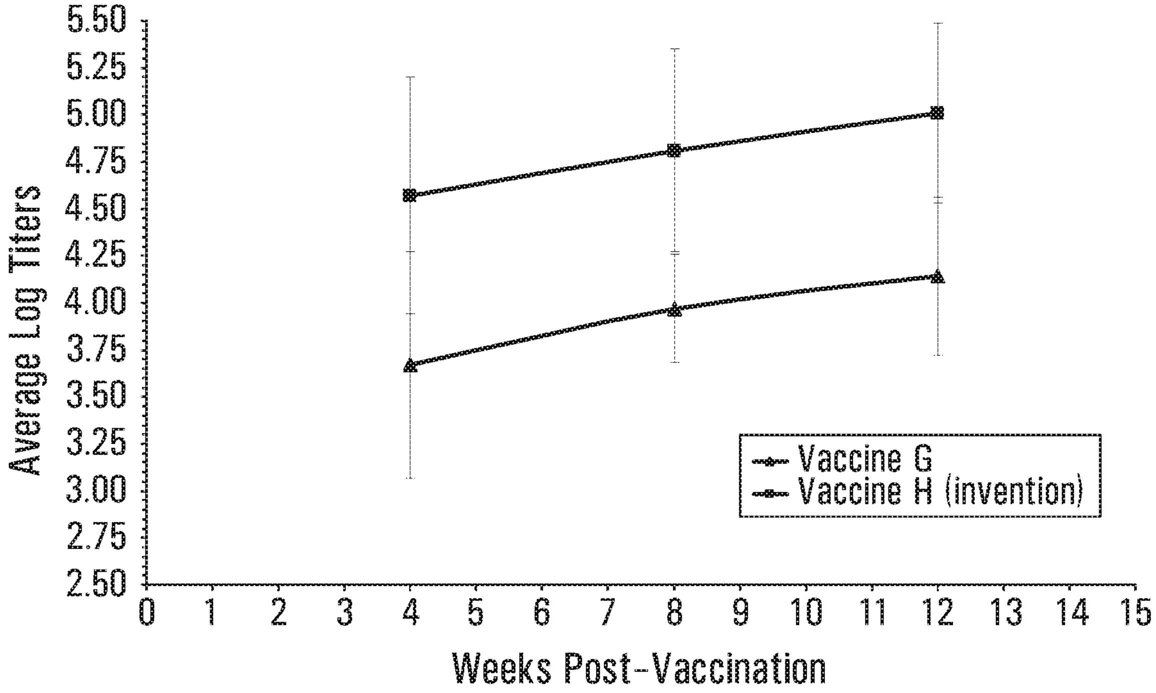
FIG. 9. Enhanced anti-β-amyloid antibody responses following vaccination with a mixture of β-amyloid and F21E peptides formulated in a liposome/polyI:C/oil carrier vaccine. Two groups of mice (n=9) were vaccinated as follows: Group 1 mice were vaccinated with 10 micrograms β-amyloid, 20 micrograms F21E and 200 micrograms alum in a 100 microliter dose formulated as a liposome/alum/hydrophobic carrier vaccine (Vaccine G). Group 2 mice were treated with 10 micrograms β-amyloid, 20 micrograms F21E and 10 micrograms polyI:C per 100 microliter dose formulated as liposome/poly:IC/hydrophobic carrier (Vaccine H, the invention). Humoral immune responses were measured by ELISA as described herein. For each treatment group, the log 10 values of the endpoint antibody titers were averaged and standard deviation calculated for each time point. P values were calculated using the student T test.
Figure 10:
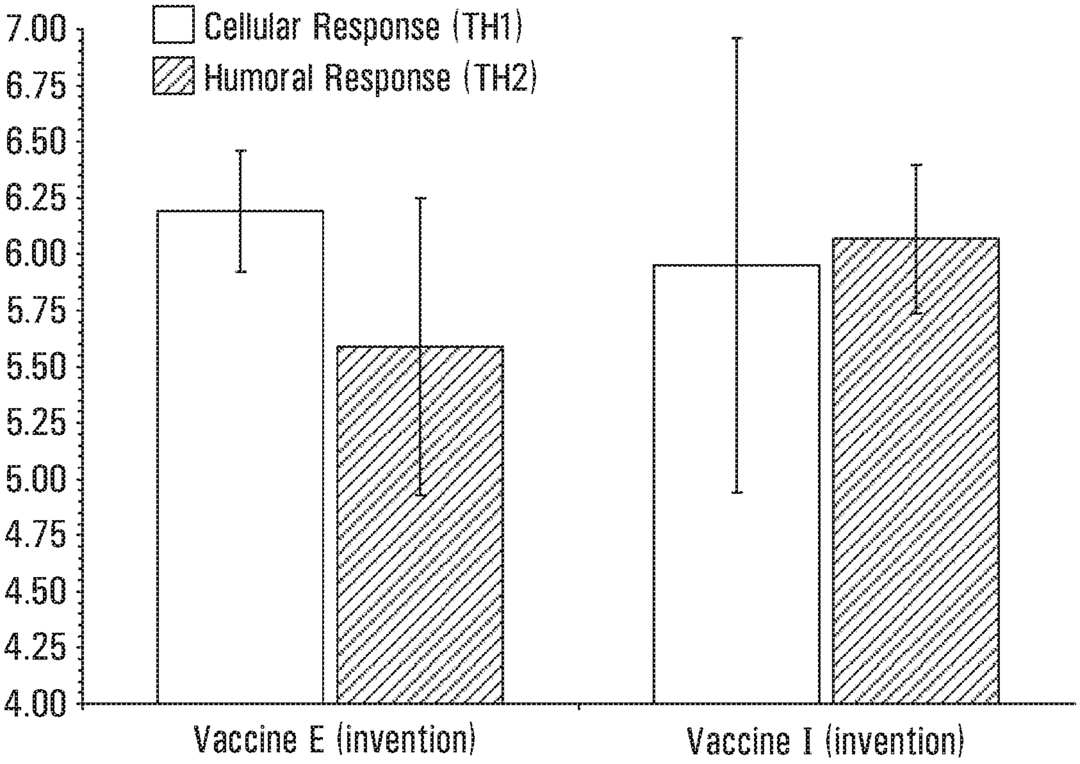
FIG. 10. Vaccines formulated in a liposome/polyI:C/hydrophobic carrier formulation are capable of raising cellular and humoral immune responses. Two groups of mice (n=5) were vaccinated as follows: Group 1 mice were vaccinated with 0.5 micrograms rHA and 12 micrograms polyI:C in a 50 microliter dose formulated as a lyophilized liposome/polyI:C (high)/hydrophobic carrier vaccine (Vaccine E, the invention). Group 2 mice were treated with 0.5 micrograms rHA and 2.5 micrograms polyI:C per 50 microliter dose formulated as lyophilized liposome/polyI:C (low)/hydrophobic carrier (Vaccine I, the invention). Indicators of humoral (IgG1) and cellular (IgG2A) immune responses were measured by ELISA as described herein. For each treatment group, the log 10 values of the endpoint antibody titers were averaged and standard deviations calculated for each time point.

The present application relates to compositions comprising liposomes, an antigen, a polyI:C polynucleotide and a carrier comprising a continuous phase of a hydrophobic substance and their use.

Compositions of the invention, combining an antigen, a polyI:C polynucleotide, liposomes and a carrier comprising a continuous phase of a hydrophobic substance provided surprisingly higher antibody titers than either conventional vaccine compositions containing polyI:C polynucleotides in an aqueous carrier, or compositions comprising liposomes, a hydrophobic carrier and an alum adjuvant.

The data described in Examples 1 and 2 herein are summarized in Table 1:

TABLE 1

| | Composition | antibody titer (log10) | antibody titer (non-logged) |
|---|---|---|---|
| (1) | rHA antigen<br>alum adjuvant<br>liposomes<br>hydrophobic carrier | 5.41 | 256,000 |
| (2) | rHA antigen<br>polyI:C<br>PBS carrier | 6.01 | 1,024,000 |
| (3) | rHA antigen<br>polyI:C<br>liposomes<br>hydrophobic carrier | 6.91 | 8,192,000 |

rHA = recombinant H5N1 influenza hemagglutinin glycoprotein
PBS = phosphate buffered saline carrier It will be seen from the above table (Table 1) that the compositions of the invention (3) provided antibody titers that were more than the additive effect of either the combination of liposomes plus hydrophobic carrier (1), or the use of polyI:C (2). The additive effect of (1) and (2) would be a non-logged antibody titer of 256,000+1,024,000=1,280,000. Instead, replacing the alum adjuvant in (3) with polyI:C gave an unexpectedly high non-logged antibody titer of 8,192,000, 6.4 times the expected additive effect. Furthermore, the antibody response generated with composition (3) was long lasting and the effect observed at the earlier time point (week 4 post-vaccination) described above was maintained at week 16 post-vaccination (Examples 4 and 5). The data described in Examples 4 and 5 herein are summarized in Table 2:

TABLE 2

| | Composition | Average antibody titer (log10) | Average antibody titer (non-logged) |
|---|---|---|---|
| (1) | rHA antigen<br>alum adjuvant<br>liposomes<br>hydrophobic carrier | 5.11 | 128,824 |
| (2) | rHA antigen<br>polyI:C<br>PBS carrier | 5.23 | 169,824 |
| (3) | rHA antigen<br>polyI:C<br>liposomes<br>hydrophobic carrier | 6.21 | 1,621,810 |

The additive effect of (1) and (2) would be a non-logged average antibody titer of 128,824+169,824=298,648. Instead, replacing the alum adjuvant in (3) with polyI:C gave an unexpectedly high non-logged average antibody titer of 1,612,810, 5.4 times the expected additive effect.

The results observed with composition (3) described above were duplicated in a separate study that used a composition consisting of antigen (rHA), polyI:C, lyophilized liposomes, and a hydrophobic carrier and described in Example 3. The average antibody titer observed with this composition at week 8 post vaccination was 2,884,031 (non logged) compared to 147,910 (non-logged) average titer observed with a standard alum-adjuvanted vaccine delivered twice to enhance its activity. This 19.4 fold average increase in titer was observed with one immunization of the composition described.

Vaccine compositions containing polyI:C, liposomes, and a hydrophobic carrier have the potential to generate antibody responses and/or cellular responses against a broad range of antigens. Examples 1 through 6 and Examples 8 and 9 demonstrate the ability to raise a significantly higher antibody response when combining all components of the composition against a recombinant protein (rHA) or a short peptide (β-amyloid). These surprisingly high antibody titers were not observed without the use of a polyI:C polynucleotide specifically in the vaccine composition (Examples 1, 4, and 9), nor were they observed in the absence of liposomes and a hydrophobic carrier despite the use of polyI:C alone with an antigen (Examples 2 and 5). Similarly, the combination of all components of the composition generated a significantly more efficacious and longer-lasting cellular immune response as illustrated in Example 7 and Examples 11 through 13 against a recombinant protein or a short peptide containing a known CTL epitope. Significant antigen-specific immune responses were detected when immunizing with the composition by at least two immunization routes (Example 7). The unusual efficacy in controlling tumor growth with the described invention were not observed without the use of a polyI:C polynucleotide specifically in the composition (Example 12) and were not observed without the use of liposomes and despite the use of a polyI:C polynucleotide and a hydrophobic carrier with the antigen (Example 11). The ability to raise robust and long lasting humoral and cellular responses simultaneously with at least one immunization using all components of the described composition (Examples 6, 7, 10, and 13) illustrates the particular usefulness of the composition in a wide range of medical applications including infectious diseases and cancers.

It is clear from the collection of examples described herein that vaccine compositions consisting of an antigen, liposomes, a hydrophobic carrier and ribo- or deoxyribo-polynucleotides containing inosine and cytosine residues in more than one chemical configuration are capable of inducing unusually strong immune responses. The examples also describe more than one method to make the desired composition.

Antigens

The compositions of the invention comprise one or more antigens. As used herein, the term "antigen" refers to a substance that can bind specifically to an antibody or to a T-cell receptor.

Antigens useful in the compositions of the invention include, without limitation, polypeptides, a microorganism or a part thereof, such as a live, attenuated, inactivated or killed bacterium, virus or protozoan, or part thereof.

As used herein and in the claims, the term "antigen" also includes a polynucleotide that encodes the polypeptide that functions as an antigen. Nucleic acid-based vaccination strategies are known, wherein a vaccine composition that contains a polynucleotide is administered to a subject. The antigenic polypeptide encoded by the polynucleotide is expressed in the subject, such that the antigenic polypeptide is ultimately present in the subject, just as if the vaccine composition itself had contained the polypeptide. For the purposes of the present invention, the term "antigen", where the context dictates, encompasses such polynucleotides that encode the polypeptide which functions as the antigen.

Polypeptides or fragments thereof that may be useful as antigens in the invention include, without limitation, those derived from Cholera toxoid, tetanus toxoid, diphtheria toxoid, hepatitis B surface antigen, hemagglutinin, neuraminidase, influenza M protein, PfHRP2, pLDH, aldolase, MSP1, MSP2, AMA1, Der-p-1, Der-f-1, Adipophilin, AFP, AIM-2, ART-4, BAGE, α-fetoprotein, BCL-2, Bcr-Abl, BING-4, CEA, CPSF, CT, cyclin D1Ep-CAM, EphA2, EphA3, ELF-2, FGF-5, G250, Gonadotropin Releasing Hormone, HER-2, intestinal carboxyl esterase (iCE), IL13Rα2, MAGE-1, MAGE-2, MAGE-3, MART-1, MART-2, M-CSF, MDM-2, MMP-2, MUC-1, NY-EOS-1, MUM-1, MUM-2, MUM-3, p53, PBF, PRAME, PSA, PSMA, RAGE-1, RNF43, RU1, RU2AS, SART-1, SART-2, SART-3, SAGE-1, SCRN 1, SOX2, SOX10, STEAP1, survivin, Telomerase, TGFβRII, TRAG-3, TRP-1, TRP-2, TERT and WT1.

Viruses, or parts thereof, useful as antigens in the invention include, without limitation, Cowpoxvirus, Vaccinia virus, Pseudocowpox virus, Human herpesvirus 1, Human herpesvirus 2, Cytomegalovirus, Human adenovirus A-F, Polyomavirus, Human papillomavirus, Parvovirus, Hepatitis A virus, Hepatitis B virus, Hepatitis C virus, Human immunodeficiency virus, Orthoreovirus, Rotavirus, Ebolavirus, parainfluenza virus, influenza A virus, influenza B virus, influenza C virus, Measles virus, Mumps virus, Rubella virus, Pneumovirus, Human respiratory syncytial virus, Rabies virus, California encephalitis virus, Japanese encephalitis virus, Hantaan virus, Lymphocytic choriomeningitis virus, Coronavirus, Enterovirus, Rhinovirus, Poliovirus, Norovirus, Flavivirus, Dengue virus, West Nile virus, Yellow fever virus and varicella.

Bacteria or parts of thereof useful as antigens in the invention include, without limitation, Anthrax, *Brucella, Candida, Chlamydia pneumoniae, Chlamydia psittaci, Cholera, Clostridium botulinum, Coccidioides immitis, Cryptococcus, Diphtheria, Escherichia coli* O157: H7, Enterohemorrhagic *Escherichia coli*, Enterotoxigenic *Escherichia coli, Haemophilus influenzae, Helicobacter pylori, Legionella, Leptospira, Listeria*, Meningococcus, *Mycoplasma pneumoniae, Mycobacterium*, Pertussis, Pneumonia, *Salmonella, Shigella, Staphylococcus, Streptococcus pneumoniae* and *Yersinia enterocolitica.*

The antigen may alternatively be of protozoan origin, e.g. *Plasmodium falciparum*, which causes malaria.

The term "polypeptide" encompasses any chain of amino acids, regardless of length (e.g., at least 6, 8, 10, 12, 14, 16, 18, or 20 amino acids) or post-translational modification (e.g., glycosylation or phosphorylation), and includes, for example, natural proteins, synthetic or recombinant polypeptides and peptides, denatured polypeptides and peptides, epitopes, hybrid molecules, variants, homologs, analogs, peptoids, peptidomimetics, etc. A variant or derivative therefore includes deletions, including truncations and fragments; insertions and additions, for example conservative substitutions, site-directed mutants and allelic variants; and modifications, including peptoids having one or more non-amino acyl groups (for example, sugar, lipid, etc.) covalently linked to the peptide and post-translational modifications. As used herein, the term "conserved amino acid substitutions" or "conservative substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Polypeptides or peptides that have substantial identity to a preferred antigen sequence may be used. Two sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e., to have substantial identity) if they share at least 60%, 70%, 75%, 80%, 85%, 90%, 95%, 96%, 97%, 98%, 99% identity over a specified region. The term "identity" refers to sequence similarity between two polypeptides molecules. Identity can be determined by comparing each position in the aligned sequences. A degree of identity between amino acid sequences is a function of the number of identical or matching amino acids at positions shared by the sequences, for example, over a specified region. Optimal alignment of sequences for comparisons of identity may be conducted using a variety of algorithms, as are known in the art, including the ClustalW program, available at http://clustalw.genome.ad.ip, the local homology algorithm of Smith and Waterman, 1981*, Adv. Appl. Math* 2: 482, the homology alignment algorithm of Needleman and Wunsch, 1970*, J. Mol. Biol.* 48:443, the search for similarity method of Pearson and Lipman, 1988*, Proc. Natl. Acad. Sci. USA* 85:2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990*, J. Mol. Biol.* 215:403-10 (using the published default settings). For example, the "BLAST 2 Sequences" tool, available through the National Center for Biotechnology Information (through the internet at http://www.ncbi.nlm.nih.qov/BLAST/b12seq/wblast2.cgi) may be used, selecting the "blastp" program at the following default settings: expect threshold 10; word size 3; matrix BLOSUM 62; gap costs existence 11, extension 1. In another embodiment, the person skilled in the art can readily and properly align any given sequence and deduce sequence identity and/or homology by mere visual inspection.

Polypeptides and peptides used to practice the invention can be isolated from natural sources, be synthetic, or be recombinantly generated polypeptides. Peptides and proteins can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K, Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

In some embodiments, the antigen may be a purified antigen, e.g., from about 25% to 50% pure, from about 50% to about 75% pure, from about 75% to about 85% pure, from about 85% to about 90% pure, from about 90% to about 95% pure, from about 95% to about 98% pure, from about 98% to about 99% pure, or greater than 99% pure.

As noted above, the term "antigen" also includes a polynucleotide that encodes the polypeptide that functions as an antigen. Nucleic acid-based vaccination strategies are known, wherein a vaccine composition that contains a polynucleotide is administered to a subject. The antigenic polypeptide encoded by the polynucleotide is expressed in the subject, such that the antigenic polypeptide is ultimately present in the subject, just as if the vaccine composition itself had contained the polypeptide. For the purposes of the present invention, the term "antigen", where the context dictates, encompasses such polynucleotides that encode the polypeptide which functions as the antigen.

As used herein and in the claims, the term "polynucleotide" encompasses a chain of nucleotides of any length (e.g. 9, 12, 18, 24, 30, 60, 150, 300, 600, 1500 or more nucleotides) or number of strands (e.g. single-stranded or double-stranded). Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

The polynucleotide may be delivered in various forms. In some embodiments, a naked polynucleotide may be used, either in linear form, or inserted into a plasmid, such as an expression plasmid. In other embodiments, a live vector such as a viral or bacterial vector may be used.

One or more regulatory sequences that aid in transcription of DNA into RNA and/or translation of RNA into a polypeptide may be present. In some instances, such as in the case of a polynucleotide that is a messenger RNA (mRNA) molecule, regulatory sequences relating to the transcription process (e.g. a promoter) are not required, and protein expression may be effected in the absence of a promoter. The skilled artisan can include suitable regulatory sequences as the circumstances require.

In some embodiments, the polynucleotide is present in an expression cassette, in which it is operably linked to regulatory sequences that will permit the polynucleotide to be expressed in the subject to which the composition of the invention is administered. The choice of expression cassette depends on the subject to which the composition is administered as well as the features desired for the expressed polypeptide.

Typically, an expression cassette includes a promoter that is functional in the subject and can be constitutive or inducible; a ribosome binding site; a start codon (ATG) if necessary; the polynucleotide encoding the polypeptide of interest; a stop codon; and optionally a 3' terminal region (translation and/or transcription terminator). Additional sequences such as a region encoding a signal peptide may be included. The polynucleotide encoding the polypeptide of interest may be homologous or heterologous to any of the other regulatory sequences in the expression cassette. Sequences to be expressed together with the polypeptide of interest, such as a signal peptide encoding region, are typically located adjacent to the polynucleotide encoding the protein to be expressed and placed in proper reading frame. The open reading frame constituted by the polynucleotide encoding the protein to be expressed solely or together with any other sequence to be expressed (e.g. the signal peptide), is placed under the control of the promoter so that transcription and translation occur in the subject to which the composition is administered.

In a related embodiment, the antigen may be an allergen and may be derived from, without limitation, cells, cell extracts, proteins, polypeptides, peptides, polysaccharides, polysaccharide conjugates, peptide and non-peptide mimics of polysaccharides and other molecules, small molecules, lipids, glycolipids, and carbohydrates of plants, animals, fungi, insects, food, drugs, dust, and mites. Allergens include but are not limited to environmental aeroallergens; plant pollens (e.g. ragweed/hayfever); weed pollen allergens; grass pollen allergens; Johnson grass; tree pollen allergens; ryegrass; arachnid allergens (e.g. house dust mite allergens); storage mite allergens; Japanese cedar pollen/hay fever; mold/fungal spore allergens; animal allergens (e.g., dog, guinea pig, hamster, gerbil, rat, mouse, etc., allergens); food allergens (e.g. crustaceans; nuts; citrus fruits; flour; coffee); insect allergens (e.g. fleas, cockroach); venoms:

(Hymenoptera, yellow jacket, honey bee, wasp, hornet, fire ant); bacterial allergens (e.g. streptococcal antigens; parasite allergens such as *Ascaris* antigen); viral antigens; drug allergens (e.g. penicillin); hormones (e.g. insulin); enzymes (e.g. streptokinase); and drugs or chemicals capable of acting as incomplete antigens or haptens (e.g. the acid anhydrides and the isocyanates).

PolyI:C Polynucleotides

PolyI:C polynucleotides are double stranded polynucleotide molecules (either RNA or DNA or a combination of DNA and RNA) containing inosinic acid residues (I) and cytidylic acid residues (C), and which induce the production of inflammatory cytokines, such as interferon. They are typically composed of one strand consisting entirely of cytosine-containing nucleotides and one strand consisting entirely of inosine-containing nucleotides although other configurations are possible. For instance, each strand may contain both cytosine-containing and inosine-containing nucleotides. In some instances, either or both strand may additionally contain one or more non-cytosine or non-inosine nucleotides.

It has been reported that polyI:C can be segmented every 16 residues without an effect on its interferon activating potential (Bobst, 1981). Furthermore, the interferon inducing potential of a polyI:C molecule mismatched by introducing a uridine residue every 12 repeating cytidylic acid residues (Hendrix, 1993), suggests that a minimal double stranded polyI:C molecule of 12 residues is sufficient to promote interferon production. Others have also suggested that regions as small as 6-12 residues, which correspond to 0.5-1 helical turn of the double stranded polynucleotide, are capable of triggering the induction process (Greene, 1978). If synthetically made, polyI:C polynucleotides are typically about 20 or more residues in length (commonly 22, 24, 26, 28 or 30 residues in length). If semisynthetically made (e.g. using an enzyme), the length of the strand may be 500, 1000 or more residues.

PolyI:C act as mimics of viral genomes and are particularly useful for modulating the immune system in vivo. Synthetic poly I:poly C homopolymers for example has been reported to enhance innate immunity by inducing interferon gamma non-specifically when delivered systemically in vivo by intravenous or intramuscular injection (Krown 1985, Zhu 2007). Several variants of poly inosinic and cytidylic acid polymers have been described over the years (de Clercq 1978, Bobst 1981, De Clercq 1975, Guschlbauer 1977, Fukui 1977, Johnston 1975, U.S. Pat. No. 3,906,092 1971, Kamath 2008, Ichinohe 2007), some of which included the use of covalently modified residues, the use of ribo and deoxy-ribo inosinic and cytidylic residues, the use of homopolymers and alternating co-polymers that contain inosinic and cytidylic acid residues, and the introduction of specific residues to create mismatched polymers.

The use of double stranded polynucleotides containing inosinic and cytidylic acids has been reported for the treatment of a number of viral diseases (Kende 1987, Poast 2002, 6,468,558 2002, Sarma 1969, Stephen 1977, Levy 1978), cancer (Durie 1985, Salazar 1996, Theriault 1986, Nakamura 1982, Talmadge 1985, Droller 1987), autoimmune disease like multiple sclerosis (Bever 1986), and other infectious diseases such as malaria (Awasthi 1997, Puri 1996). The efficacy of polyI:C molecules has been further enhanced in some cases by complexing the molecule with positively charged poly-lysine and carboxymethyl-cellulose, effectively protecting the polynucleotide from nuclease degradation in vivo (Stephen 1977, Levy 1985), or by complexing polyI:C with positively charged synthetic peptides (Schellack 2006).

In addition to its uses as a non-specific enhancer of innate immunity, polyI:C is also useful as adjuvant in vaccine compositions. The enhancement of innate immunity can lead to an enhanced antigen specific adaptive immunity, possibly through a mechanism that involves, at least in part, NK cells, macrophages and/or dendritic cells (Chirigos 1985, Salem 2006, Alexopoulou 2001, Trumpfheller 2008). Evidence for the use of polyI:C molecules in this context originates from various vaccine studies for controlling infectious diseases (Houston 1976, Stephen 1977, Ichinohe 2007, Sloat 2008, Agger 2006, Padalko 2004) and the prevention or treatment of cancer by a variety of vaccine modalities (Zhu 2007, Cui 2006, Salem 2005, Fujimura 2006, Llopiz 2008). These studies demonstrate that polyI:C enhances humoral responses as evident from enhanced antibody responses against specific infectious disease antigens. PolyI:C is also a potentiator of antigen-specific cellular responses (Zhu 2007, Zaks 2006, Cui 2006, Riedl 2008). The adjuvanting effects of PolyI:C molecules are believed to occur, at least partially, by inducing interferon-gamma through their interaction with toll like receptors (TLR) such as TLR3, TLR4, TLR7, TLR8 and TLR9 (Alexopoulou 2001, Trumpfheller 2008, Schellack 2006, Riedl 2008), with TLR3 being particularly relevant for most polyI:C molecules. Evidence also suggests that polyI:C molecules may exert their effect, at least in part, by interacting with receptors other than TLRs, such as the RNA helicase retinoic acid induced protein I (RIG-I)/melanoma differentiation associated gene 5 (MDA5) (Alexopoulou 2001, Yoneyama 2004, Gowen 2007, Dong 2008). The mechanism of action of polyI:C molecules remains to be fully understood.

Accordingly, as used herein, a "polyI:C" or "polyI:C polynucleotide" is a double-stranded polynucleotide molecule (RNA or DNA or a combination of DNA and RNA), each strand of which contains at least 6 contiguous inosinic or cytidylic acid residues, or 6 contiguous residues selected from inosinic acid and cytidylic acid in any order (e.g. IICIIC or ICICIC), and which is capable of inducing or enhancing the production of at least one inflammatory cytokine, such as interferon, in a mammalian subject. PolyI:C polynucleotides will typically have a length of about 8, 10, 12, 14, 16, 18, 20, 22, 24, 25, 28, 30, 35, 40, 45, 50, 55, 60, 65, 70, 75, 80, 85, 90, 95, 100, 150, 200, 250, 300, 500, 1000 or more residues. The upper limit is not believed to be essential. Preferred polyI:C polynucleotides may have a minimum length of about 6, 8, 10, 12, 14, 16, 18, 20, 22, 24, 26, 28, or 30 nucleotides and a maximum length of about 1000, 500, 300, 200, 100, 90, 80, 70, 60, 50, 45 or 40 nucleotides.

Each strand of a polyI:C polynucleotide may be a homopolymer of inosinic or cytidylic acid residues, or each strand may be a heteropolymer containing both inosinic and cytidylic acid residues. In either case, the polymer may be interrupted by one or more non-inosinic or non-cytidylic acid residues (e.g. uridine), provided there is at least one contiguous region of 6 I, 6 C or 6 I/C residues as described above. Typically, each strand of a polyI:C polynucleotide will contain no more than 1 non-I/C residue per 6 I/C residues, more preferably, no more than 1 non-I/C residue per every 8, 10, 12, 14, 16, 18, 20, 22, 24, 26, 28 or 30 I/C residues.

The inosinic acid or cytidylic acid (or other) residues in the polyI:C polynucleotide may be derivatized or modified as is known in the art, provided the ability of the polyI:C polynucleotide to promote the production of an inflammatory cytokine, such as interferon, is retained. Non-limiting examples of derivatives or modifications include e.g. azido modifications, fluoro modifications, or the use of thioester (or similar) linkages instead of natural phosphodiester linkages to enhance stability in vivo. The polyI:C polynucleotide may also be modified to e.g. enhance its resistance to degradation in vivo by e.g. complexing the molecule with positively charged poly-lysine and carboxymethylcellulose, or with a positively charged synthetic peptide.

The polyI:C polynucleotide will typically be included in the compositions of the invention in an amount from about 0.001 mg to 1 mg per unit dose of the composition.

Liposomes

Liposomes are completely closed lipid bilayer membranes containing an entrapped aqueous volume. Liposomes may be unilamellar vesicles (possessing a single bilayer membrane) or multilamellar vesicles characterized by multimembrane bilayers, each bilayer may or may not be separated from the next by an aqueous layer. A general discussion of liposomes can be found in Gregoriadis G. *Immunol. Today,* 11:89-97, 1990; and Frezard, F., Braz. *J. Med. Bio. Res.,* 32:181-189, 1999. As used herein and in the claims, the term "liposomes" is intended to encompass all such vesicular structures as described above, including, without limitation, those described in the art as "niosomes", "transfersomes" and "virosomes".

Although any liposomes may be used in this invention, including liposomes made from archaebacterial lipids, particularly useful liposomes use phospholipids and unesterified cholesterol in the liposome formulation. The cholesterol is used to stabilize the liposomes and any other compound that stabilizes liposomes may replace the cholesterol. Other liposome stabilizing compounds are known to those skilled in the art. For example, saturated phospholipids produce liposomes with higher transition temperatures indicating increased stability.

Phospholipids that are preferably used in the preparation of liposomes are those with at least one head group selected from the group consisting of phosphoglycerol, phosphoethanolamine, phosphoserine, phosphocholine and phosphoinositol. More preferred are liposomes that comprise lipids which are 94-100% phosphatidylcholine. Such lipids are available commercially in the lecithin Phospholipon® 90 G. When unesterified cholesterol is also used in liposome formulation, the cholesterol is used in an amount equivalent to about 10% of the amount of phospholipid. If a compound other than cholesterol is used to stabilize the liposomes, one skilled in the art can readily determine the amount needed in the composition.

Liposome compositions may be obtained, for example, by using natural lipids, synthetic lipids, sphingolipids, ether lipids, sterols, cardiolipin, cationic lipids and lipids modified with poly (ethylene glycol) and other polymers. Synthetic lipids may include the following fatty acid constituents; lauroyl, myristoyl, palmitoyl, stearoyl, arachidoyl, oleoyl, linoleoyl, erucoyl, or combinations of these fatty acids.

Carriers

The carrier of the composition comprises a continuous phase of a hydrophobic substance, preferably a liquid hydrophobic substance. The continuous phase may be an essentially pure hydrophobic substance or a mixture of hydrophobic substances. In addition, the carrier may be an emulsion of water in a hydrophobic substance or an emulsion of water in a mixture of hydrophobic substances, provided the hydrophobic substance constitutes the continuous phase. Further, in another embodiment, the carrier may function as an adjuvant.

Hydrophobic substances that are useful in the compositions as described herein are those that are pharmaceutically and/or immunologically acceptable. The carrier is preferably a liquid but certain hydrophobic substances that are not liquids at atmospheric temperature may be liquefied, for example by warming, and are also useful in this invention. In one embodiment, the hydrophobic carrier may be a Phosphate Buffered Saline/Freund's Incomplete Adjuvant (PBS/FIA) emulsion.

Oil or water-in-oil emulsions are particularly suitable carriers for use in the present invention. Oils should be pharmaceutically and/or immunologically acceptable. Suitable oils include, for example, mineral oils (especially light or low viscosity mineral oil such as Drakeol® 6VR), vegetable oils (e.g., soybean oil), nut oils (e.g., peanut oil), or mixtures thereof. In an embodiment, the oil is a mannide oleate in mineral oil solution, commercially available as Montanide® ISA 51. Animal fats and artificial hydrophobic polymeric materials, particularly those that are liquid at atmospheric temperature or that can be liquefied relatively easily, may also be used.

Other Components

The composition may further comprise one or more pharmaceutically acceptable adjuvants, excipients, etc., as are known in the art: See, for example, Remington's Pharmaceutical Sciences (Remington's Pharmaceutical Sciences, Mack Publishing Company, Easton, Pa., USA 1985) and The United States Pharmacopoeia: The National Formulary (USP 24 NF19) published in 1999.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al, Immunology, 2d ed., Benjamin/Cummings: Menlo Park, Calif., 1984; see Wood and Williams, In: Nicholson, Webster and May (eds.), Textbook of Influenza, Chapter 23, pp. 317-323). Often, a primary challenge with an antigen alone, in the absence of an adjuvant, will fail to elicit a humoral immune response.

Suitable adjuvants include, but are not limited to, alum, other compounds of aluminum, *Bacillus* of Calmette and Guerin (BCG), TiterMax®, Ribi®, incomplete Freund's adjuvant (IFA), saponin, surface active substances such as lysolecithin, pluronic polyols, polyanions, peptides, Corynebacteriumparvum, QS-21, Freund's Complete Adjuvant (FCA), adjuvants of the TLR agonist family such as CpG, falgellin, lipopeptides, peptidoglycans, imidazoquinolines, single stranded RNA, lipopolysaccharides (LPS), heat shock proteins (HSP), and ceramides and derivatives such as αGal-cer. Suitable adjuvants also include cytokines or chemokines in their polypeptide or DNA coding forms such as, but not limited to, GM-CSF, TNF-α, IFN-γ, IL-2, IL-12, IL-15, IL-21. A suitable alum adjuvant is sold under the trade name Imject Alum® (Pierce, Rockford, Ill.), that consists of an aqueous solution of aluminum hydroxide (45 mg/ml) and magnesium hydroxide (40 mg/ml) plus inactive stabilizers.

The amount of adjuvant used depends on the amount of antigen and on the type of adjuvant. One skilled in the art can readily determine the amount of adjuvant needed in a particular application.

An immune response elicited in subjects administered a composition of the invention may be formulated to bias the immune response towards an antibody or a cell mediated immune response. This may be achieved by using agents, such as adjuvants, that predominantly induce a Th1 or Th2 response. For example, a CpG-containing oligonucleotides (in which the CpG dinucleotide is unmethylated) may be used to induce a predominantly Th1 response, thus favouring a cell mediated response.

Compositions

Methods for making liposomes are well known in the art. See e.g. Gregoriadis (1990) and Frezard (1999) both cited previously. Any suitable method for making liposomes may be used in the practice of the invention, or liposomes may be obtained from a commercial source. Liposomes are typically prepared by hydrating the liposome components that will form the lipid bilayer (e.g. phospholipids and cholesterol) with an aqueous solution, which may be pure water or a solution of one or more components dissolved in water, e.g. phosphate-buffered saline (PBS), phosphate-free saline, or any other physiologically compatible aqueous solution.

In an embodiment, a liposome component or mixture of liposome components, such as a phospholipid (e.g. Phospholipon® 90G) and cholesterol, may be solubilized in an organic solvent, such as a mixture of chloroform and methanol, followed by filtering (e.g. a PTFE 0.2 μm filter) and drying, e.g. by rotary evaporation, to remove the solvents.

Hydration of the resulting lipid mixture may be effected by e.g. injecting the lipid mixture into an aqueous solution or sonicating the lipid mixture and an aqueous solution. During formation of liposomes, the liposome components form single bilayers (unilamellar) or multiple bilayers (multilamellar) surrounding a volume of the aqueous solution with which the liposome components are hydrated.

In some embodiments, the liposomes are then dehydrated, such as by freeze-drying or lyophilization.

The liposomes are combined with the carrier comprising a continuous hydrophobic phase. This can be done in a variety of ways.

If the carrier is composed solely of a hydrophobic substance or a mixture of hydrophobic substances (e.g. use of a 100% mineral oil carrier), the liposomes may simply be mixed with the hydrophobic substance, or if there are multiple hydrophobic substances, mixed with any one or a combination of them.

If instead the carrier comprising a continuous phase of a hydrophobic substance contains a discontinuous aqueous phase, the carrier will typically take the form of an emulsion of the aqueous phase in the hydrophobic phase, such as a water-in-oil emulsion. Such compositions may contain an emulsifier to stabilize the emulsion and to promote an even distribution of the liposomes. In this regard, emulsifiers may be useful even if a water-free carrier is used, for the purpose of promoting an even distribution of the liposomes in the carrier. Typical emulsifiers include mannide oleate (Arlacel™ A), lecithin, Tween™ 80, and Spans™ 20, 80, 83 and 85. Typically, the volume ratio (v/v) of hydrophobic substance to emulsifier is in the range of about 5:1 to about 15:1 with a ratio of about 10:1 being preferred.

The liposomes may be added to the finished emulsion, or they may be present in either the aqueous phase or the hydrophobic phase prior to emulsification.

The antigen may be introduced at various different stages of the formulation process. More than one type of antigen may be incorporated into the composition (e.g. an inactivated virus, attenuated live virus, protein or polypeptide).

In some embodiments, the antigen is present in the aqueous solution used to hydrate the components that are used to form the lipid bilayers of the liposomes (e.g. phospholipid(s) and cholesterol). In this case, the antigen will be encapsulated in the liposome, present in its aqueous interior. If the resulting liposomes are not washed or dried, such that there is residual aqueous solution present that is ultimately mixed with the carrier comprising a continuous phase of a hydrophobic substance, it is possible that additional antigen may be present outside the liposomes in the final product. In a related technique, the antigen may be mixed with the components used to form the lipid bilayers of the liposomes, prior to hydration with the aqueous solution.

In an alternative approach, the antigen may instead be mixed with the carrier comprising a continuous phase of a hydrophobic substance, before, during, or after the carrier is combined with the liposomes. If the carrier is an emulsion, the antigen may be mixed with either or both of the aqueous phase or hydrophobic phase prior to emulsification. Alternatively, the antigen may be mixed with the carrier after emulsification.

The technique of combining the antigen with the carrier may be used together with encapsulation of the antigen in the liposomes as described above, such that antigen is present both within the liposomes and in the carrier comprising a continuous phase of a hydrophobic substance.

The above-described procedures for introducing the antigen into the composition apply also to the polyI:C. That is, the polyI:C may be introduced into e.g. any one or more of: (1) the aqueous solution used to hydrate the components that are used to form the lipid bilayers of the liposomes; (2) the components used to form the lipid bilayers of the liposomes; or (3) the carrier comprising a continuous phase of a hydrophobic substance, before, during, or after the carrier is combined with the liposomes. If the carrier is an emulsion, the polyI:C may be mixed with either or both of the aqueous phase or hydrophobic phase prior to emulsification. Alternatively, the polyI:C may be mixed with the carrier after emulsification.

The technique of combining the polyI:C with the carrier may be used together with encapsulation of the polyI:C in the liposomes, such that polyI:C is present both within the liposomes and in the carrier comprising a continuous phase of a hydrophobic substance.

The polyI:C can be incorporated in the composition together with the antigen at the same processing step, or separately, at a different processing step. For instance, the antigen and the polyI:C may both be present in the aqueous solution used to hydrate the lipid bilayer-forming liposome components, such that both the antigen and polyI:C become encapsulated in the liposomes. Alternatively, the antigen may be encapsulated in the liposomes, and the polyI:C mixed with the carrier comprising a continuous phase of a hydrophobic substance. It will be appreciated that many such combinations are possible.

If the composition contains one or more adjuvants, the adjuvant can be incorporated in the composition together with the antigen at the same processing step, or separately, at a different processing step. For instance, the antigen and adjuvant may both be present in the aqueous solution used to hydrate the lipid bilayer-forming liposome components, such that both the antigen and adjuvant become encapsulated in the liposomes. Alternatively, the antigen may be encapsulated in the liposomes, and the adjuvant mixed with the carrier comprising a continuous phase of a hydrophobic substance.

Stabilizers such as sugars, anti-oxidants, or preservatives that maintain the biological activity or improve chemical stability to prolong the shelf life of antigen, adjuvant, the liposomes or the continuous hydrophobic carrier, may be added to such compositions.

In some embodiments, an antigen/polyI:C mixture may be used, in which case the antigen and the polyI:C polynucleotide are incorporated into the composition at the same time. An "antigen/polyI:C mixture" refers to an embodiment in which the antigen and polyI:C polynucleotide are in the same diluent at least prior to incorporation into the composition. The antigen and polyI:C polynucleotide in an antigen/polyI:C mixture may, but need not necessarily be chemically linked, such as by covalent bonding.

Similarly, in some embodiments, an antigen/adjuvant mixture may be used, in which case the antigen and adjuvant are incorporated into the composition at the same time. An "antigen/adjuvant mixture" refers to an embodiment in which the antigen and adjuvant are in the same diluent at least prior to incorporation into the composition. The antigen and adjuvant in an antigen/adjuvant mixture may, but need not necessarily be chemically linked, such as by covalent bonding.

In some embodiments, the carrier comprising a continuous phase of a hydrophobic substance may itself have adjuvanting-activity. Incomplete Freund's adjuvant, is an example of a hydrophobic carrier with adjuvanting effect. As used herein and in the claims, when the term "adjuvant" is used, this is intended to indicate the presence of an adjuvant in addition to any adjuvanting activity provided by the carrier comprising a continuous phase of a hydrophobic substance.

The compositions as described herein may be formulated in a form that is suitable for oral, nasal, rectal or parenteral administration. Parenteral administration includes intravenous, intraperitoneal, intradermal, subcutaneous, intramuscular, transepithelial, intrapulmonary, intrathecal, and topical modes of administration. Preferred routes include intramuscular, subcutaneous and intradermal administration to achieve a depot effect. In embodiments where the composition of the invention is for the treatment of cancer tumors, the composition may be formulated for delivery by injection directly into the tumor, or adjacent to the tumor. In some embodiments, the composition may be delivered evenly over or throughout the tumor to enhance the biodistribution and hence enhance the therapeutic benefit.

In further embodiments, a composition of the invention may be formulated with DNA based polyI:C, RNA based polyI:C or a mixture of RNA and DNA based polyI:C. In this context, a RNA and DNA mixture may relate to nucleotides, such that each strand may comprises DNA and RNA nucleotides; to the strands, such that each double stranded polynucleotide has one DNA strand and one RNA strand; to the polynucleotide, such that a composition contains polyI:C polynucleotides, each of which are wholly composed of RNA or wholly composed of DNA; or combinations thereof.

In other embodiments, the compositions of the invention may be formulated for use in combination with a T cell epitope or a B cell epitope. The T cell epitope may be a universal T cell epitope and the B cell epitope may be a universal B cell epitope. As used herein, a "universal epitope" may be any epitope that is broadly recognized, for example, by T cells or B cells of multiple strains of an animal. In one embodiment, the T cell epitope may be a tetanus toxoid peptide such as F21E. In another embodiment, the T cell epitope may be PADRE, a universal helper T cell epitope. Other universal epitopes that may be suitable for use in the context of the invention are known to the skilled person or may be readily identified using routine techniques.

In related embodiments, a composition of the invention comprises a polyI:C polynucleotide and an antigen, where the presence of the polyI:C polynucleotide and the antigen in terms of weight or number of molecules is in a ratio of less than 1 to 1,000, of less than 1 to 900, of less than 1 to 800, of less than 1 to 700, of less than 1 to 500, of less than 1 to 400, of less than 1 to 300, of less than 1 to 200, of less than 1 to 100, of less than 1 to 50, of less than 1 to 10, of less than 1 to 5, of less than 1 to 2, of about 1 to 1, of greater than 2 to 1, of greater than 5 to 1, of greater than 10 to 1, of greater than 50 to 1, of greater than 100 to 1, of greater than 200 to 1, of greater than 300 to 1, of greater than 400 to 1, of greater than 500 to 1, of greater than 600 to 1, of greater than 700 to 1, of greater than 800 to 1, of greater than 900 to 1, of greater than 1,000 to 1.

The optimal amount of polyI:C polynucleotide to antigen to elicit an optimal immune response may depend on a number of factors including, without limitation, the composition, the disease, the subject, and may be readily ascertained by the skilled person using standard studies including, for example, observations of antibody titers and other immunogenic responses in the host.

Kits and Reagents

The present invention is optionally provided to a user as a kit. For example, a kit of the invention contains one or more of the compositions of the invention. The kit can further comprise one or more additional reagents, packaging material, containers for holding the components of the kit, and an instruction set or user manual detailing preferred methods of using the kit components.

Methods of Use

The invention finds application in any instance in which it is desired to administer an antigen to a subject. The subject may be a vertebrate, such as a fish, bird or mammal, preferably a human.

In some embodiments, the compositions of the invention may be administered to a subject in order to elicit and/or enhance an antibody response to the antigen.

As used herein, to "elicit" an immune response is to induce and/or potentiate an immune response. As used herein, to "enhance" an immune response is to elevate, improve or strengthen the immune response to the benefit of the host relative to the prior immune response status, for example, before the administration of a composition of the invention.

An "antibody" is a protein comprising one or more polypeptides substantially or partially encoded by immunoglobulin genes or fragments of immunoglobulin genes. The recognized immunoglobulin genes include the κ, Δ, α, γ, δ, ε and μ constant region genes, as well as myriad immunoglobulin variable region genes. Light chains are classified as either κ or λ. Heavy chains are classified as γ, μ, α, δ, or ε, which in turn define the immunoglobulin classes, IgG, IgM, IgA, IgD and IgE, respectively. A typical immunoglobulin (antibody) structural unit comprises a protein containing four polypeptides. Each antibody structural unit is composed of two identical pairs of polypeptide chains, each having one "light" and one "heavy" chain. The N-terminus of each chain defines a variable region primarily responsible for antigen recognition. Antibody structural units (e.g. of the IgA and IgM classes) may also assemble into oligomeric forms with each other and additional polypeptide chains, for example as IgM pentamers in association with the J-chain polypeptide.

Antibodies are the antigen-specific glycoprotein products of a subset of white blood cells called B lymphocytes (B cells). Engagement of antigen with antibody expressed on the surface of B cells can induce an antibody response comprising stimulation of B cells to become activated, to undergo mitosis and to terminally differentiate into plasma cells, which are specialized for synthesis and secretion of antigen-specific antibody.

As used herein, the term "antibody response" refers to an increase in the amount of antigen-specific antibodies in the body of a subject in response to introduction of the antigen into the body of the subject.

One method of evaluating an antibody response is to measure the titers of antibodies reactive with a particular antigen. This may be performed using a variety of methods known in the art such as enzyme-linked immunosorbent assay (ELISA) of antibody-containing substances obtained from animals. For example, the titers of serum antibodies which bind to a particular antigen may be determined in a subject both before and after exposure to the antigen. A statistically significant increase in the titer of antigen-specific antibodies following exposure to the antigen would indicate the subject had mounted an antibody response to the antigen.

Other assays that may be used to detect the presence of an antigen-specific antibody include, without limitation, immunological assays (e.g. radioimmunoassay (RIA)), immunoprecipitation assays, and protein blot (e.g. Western blot) assays; and neutralization assays (e.g., neutralization of viral infectivity in an in vitro or in vivo assay).

In some embodiments, the compositions of the invention may be administered to a subject in order to elicit and/or enhance a cell-mediated immune response to the antigen. As used herein, the term "cell-mediated immune response" refers to an increase in the amount of antigen-specific cytotoxic T-lymphocytes, macrophages, natural killer cells, or cytokines in the body of a subject in response to introduction of the antigen into the body of the subject.

Historically, the immune system was separated into two branches: humoral immunity, for which the protective function of immunization could be found in the humor (cell-free bodily fluid or serum that contain antibodies) and cellular immunity, for which the protective function of immunization was associated with cells. Cell-mediated immunity is an immune response that involves the activation of macrophages, natural killer cells (NK), antigen-specific cytotoxic T-lymphocytes, and the release of various cytokines in response to a 'non-self' antigen. Cellular immunity is an important component of adaptive immune response and following recognition of antigen by cells through their interaction with antigen-presenting cells such as dendritic cells, B lymphocytes and to a lesser extent, macrophages, protects the body by various mechanisms such as:

1. activating antigen-specific cytotoxic T-lymphocytes that are able to induce apoptosis in body cells displaying epitopes of foreign antigen on their surface, such as virus-infected cells, cells with intracellular bacteria, and cancer cells displaying tumor antigens;
2. activating macrophages and natural killer cells, enabling them to destroy intracellular pathogens; and
3. stimulating cells to secrete a variety of cytokines that influence the function of other cells involved in adaptive immune responses and innate immune responses.

Cell-mediated immunity is most effective in removing virus-infected cells, but also participates in defending against fungi, protozoans, cancers, and intracellular bacteria. It also plays a major role in transplant rejection.

Detection of Cell Mediated Immune Response Following Vaccination

Since cell mediated immunity involves the participation of various cell types and is mediated by different mechanisms, several methods could be used to demonstrate the induction of immunity following vaccination. These could be broadly classified into detection of: i) specific antigen presenting cells; ii) specific effector cells and their functions and iii) release of soluble mediators such as cytokines.

i) Antigen Presenting Cells:

Dendritic cells and B-cells (and to a lesser extent macrophages) are equipped with special immuno-stimulatory receptors that allow for enhanced activation of T cells, and are termed professional antigen presenting cells (APC). These immuno-stimulatory molecules (also called as co-stimulatory molecules) are up-regulated on these cells following infection or vaccination, during the process of antigen presentation to effector cells such as CD4 and CD8 cytotoxic T cells. Such co-stimulatory molecules (such as CD80, CD86, MHC class I or MHC class II) can be detected by using flow cytometry with fluorochrome-conjugated antibodies directed against these molecules along with antibodies that specifically identify APC (such as CD11c for dendritic cells).

ii) Cytotoxic T Cells:

(also known as Tc, killer T cell, or cytotoxic T-lymphocyte (CTL)) are a sub-group of T cells which induce the death of cells that are infected with viruses (and other pathogens), or expressing tumor antigens. These CTLs directly attack other cells carrying certain foreign or abnormal molecules on their surface. The ability of such cellular cytotoxicity can be detected using in vitro cytolytic assays (chromium release assay). Thus, induction of adaptive cellular immunity can be demonstrated by the presence of such cytotoxic T cells, wherein, when antigen loaded target cells are lysed by specific CTLs that are generated in vivo following vaccination or infection.

Naive cytotoxic T cells are activated when their T-cell receptor (TCR) strongly interacts with a peptide-bound MHC class I molecule. This affinity depends on the type and orientation of the antigen/MHC complex, and is what keeps the CTL and infected cell bound together. Once activated the CTL undergoes a process called clonal expansion in which it gains functionality, and divides rapidly, to produce an army of "armed"-effector cells. Activated CTL will then travel throughout the body in search of cells bearing that unique MHC Class I+peptide. This could be used to identify such CTLs in vitro by using peptide-MHC Class I tetramers in flow cytometric assays.

When exposed to these infected or dysfunctional somatic cells, effector CTL release perforin and granulysin: cytotoxins which form pores in the target cell's plasma membrane, allowing ions and water to flow into the infected cell, and causing it to burst or lyse. CTL release granzyme, a serine protease that enters cells via pores to induce apoptosis (cell death). Release of these molecules from CTL can be used as a measure of successful induction of cellular immune response following vaccination. This can be done by enzyme linked immunosorbant assay (ELISA) or enzyme linked immunospot assay (ELISPOT) where CTLs can be quantitatively measured. Since CTLs are also capable of producing important cytokines such as IFN-γ, quantitative measurement of IFN-γ-producing CD8 cells can be achieved by ELISPOT and by flowcytometric measurement of intracellular IFN-γ in these cells.

Cd4+ "Helper" T-Cells:

CD4+ lymphocytes, or helper T cells, are immune response mediators, and play an important role in establishing and maximizing the capabilities of the adaptive immune response. These cells have no cytotoxic or phagocytic activity; and cannot kill infected cells or clear pathogens, but, in essence "manage" the immune response, by directing other cells to perform these tasks. Two types of effector CD4+ T helper cell responses can be induced by a professional APC, designated Th1 and Th2, each designed to eliminate different types of pathogens.

Helper T cells express T-cell receptors (TCR) that recognize antigen bound to Class II MHC molecules. The activation of a naive helper T-cell causes it to release cytokines, which influences the activity of many cell types, including the APC that activated it. Helper T-cells require a much milder activation stimulus than cytotoxic T-cells. Helper T-cells can provide extra signals that "help" activate cytotoxic cells. Two types of effector CD4+ T helper cell responses can be induced by a professional APC, designated Th1 and Th2, each designed to eliminate different types of pathogens. The two Th cell populations differ in the pattern of the effector proteins (cytokines) produced. In general, Th1 cells assist the cellular immune response by activation of macrophages and cytotoxic T-cells; whereas Th2 cells promote the humoral immune response by stimulation of B-cells for conversion into plasma cells and by formation of antibodies. For example, a response regulated by Th1 cells may induce IgG2a and IgG2b in mouse (IgG1 and IgG3 in humans) and favor a cell mediated immune response to an antigen. If the IgG response to an antigen is regulated by Th2 type cells, it may predominantly enhance the production of IgG1 in mouse (IgG2 in humans). The measure of cytokines associated with Th1 or Th2 responses will give a measure of successful vaccination. This can be achieved by specific ELISA designed for Th1-cytokines such as IFN-γ, IL-2, IL-12, TNF-α and others, or Th2-cytokines such as IL-4, IL-5,11_10 among others.

iii) Measurement of Cytokines:

released from regional lymph nodes gives a good indication of successful immunization. As a result of antigen presentation and maturation of APC and immune effector cells such as CD4 and CD8 T cells, several cytokines are released by lymph node cells. By culturing these LNC in vitro in the presence of antigen, antigen-specific immune response can be detected by measuring release if certain important cytokines such as IFN-γ, IL-2, IL-12, TNF-α and GM-CSF. This could be done by ELISA using culture supernatants and recombinant cytokines as standards.

Successful immunization may be determined in a number of ways known to the skilled person including, but not limited to, hemagglutination inhibition (I-IAI) and serum neutralization inhibition assays to detect functional antibodies; challenge studies, in which vaccinated subjects are challenged with the associated pathogen to determine the efficacy of the vaccination; and the use of fluorescence activated cell sorting (FACS) to determine the population of cells that express a specific cell surface marker, e.g. in the identification of activated or memory lymphocytes. A skilled person may also determine if immunization with a composition of the invention elicited an antibody and/or cell mediated immune response using other known methods. See, for example, Current Protocols in Immunology Coligan et al., ed. (Wiley Interscience, 2007).

In further embodiments, the compositions of the invention may be administered to a subject to elicit and/or enhance an antibody and a cell mediated immune response to the antigen.

The invention finds broad application in the prevention and treatment of any disease susceptible to prevention and/or treatment by way of administration of an antigen. Representative applications of the invention include cancer treatment and prevention, gene therapy, adjuvant therapy, infectious disease treatment and prevention, allergy treatment and prevention, autoimmune disease treatment and prevention, neuron-degenerative disease treatment, and atherosclerosis treatment, drug dependence treatment and prevention, hormone control for disease treatment and prevention, control of a biological process for the purpose of contraception.

Prevention or treatment of disease includes obtaining beneficial or desired results, including clinical results. Beneficial or desired clinical results can include, but are not limited to, alleviation or amelioration of one or more symptoms or conditions, diminishment of extent of disease, stabilisation of the state of disease, prevention of development of disease, prevention of spread of disease, delay or slowing of disease progression, delay or slowing of disease onset, conferring protective immunity against a disease-causing agent and amelioration or palliation of the disease state. Prevention or treatment can also mean prolonging survival of a patient beyond that expected in the absence of treatment and can also mean inhibiting the progression of disease temporarily, although more preferably, it involves preventing the occurrence of disease such as by preventing infection in a subject.

The skilled artisan can determine suitable treatment regimes, routes of administration, dosages, etc., for any particular application in order to achieve the desired result. Factors that may be taken into account include, e.g.: the nature of the antigen; the disease state to be prevented or treated; the age, physical condition, body weight, sex and diet of the subject; and other clinical factors. See, for example, "Vaccine Handbook", edited by the Researcher's Associates (Gaku-yuu-kai) of The National Institute of Health (1994); "Manual of Prophylactic Inoculation, 8th edition", edited by Mikio Kimura, Munehiro Hirayama, and Harumi Sakai, Kindai Shuppan (2000); "Minimum Requirements for Biological Products", edited by the Association of Biologicals Manufacturers of Japan (1993).

Immune Responses

A composition of the invention may be used to induce an antibody response and/or cell-mediated immune response to the antigen that is formulated in the composition in a subject in need thereof. An immune response may be elicited and/or enhanced in a subject in need thereof to any antigen and/or to the cell that expresses it. Thus, in embodiments of the invention, a composition may comprise an antigen derived from a bacteria, a virus, a fungus, a parasite, an allergen or a tumor cell, and may be formulated for use in the treatment and/or prevention of a disease caused by a bacteria, a virus, a fungus, a parasite, an allergen or a tumor cell, respectively.

A composition of the invention may be suitable for use in the treatment and/or prevention of cancer in a subject in need thereof. The subject may have cancer or may be at risk of developing cancer. Cancers that may be treated and/or prevented by the use or administration of a composition of the invention include, without limitation, carcinoma, adenocarcinoma, lymphoma, leukemia, sarcoma, blastoma, myeloma, and germ cell tumors. In one embodiment, the cancer may be caused by a pathogen, such as a virus. Viruses linked to the development of cancer are known to the skilled person and include, but are not limited to, human papillomaviruses (HPV), John Cunningham virus (JCV), Human herpes virus 8, Epstein Barr Virus (EBV), Merkel cell polyomavirus, Hepatitis C Virus and Human T cell leukaemia virus-1. A composition of the invention may be used for either the treatment or prophylaxis of cancer, for example, in the reduction of the severity of cancer or the prevention of cancer recurrences. Cancers that may benefit from the compositions of the invention include any malignant cell that expresses one or more tumor specific antigen.

A composition of the invention may be suitable for use in the treatment and/or prevention of a viral infection in a subject in need thereof. The subject may be infected with a virus or may be at risk of developing a viral infection. Viral infections that may be treated and/or prevented by the use or administration of a composition of the invention include, without limitation, Cowpoxvirus, Vaccinia virus, Pseudocowpox virus, Human herpesvirus 1, Human herpesvirus 2, Cytomegalovirus, Human adenovirus A-F, Polyomavirus, Human papillomavirus, Parvovirus, Hepatitis A virus, Hepatitis B virus, Hepatitis C virus, Human immunodeficiency virus, Orthoreovirus, Rotavirus, Ebolavirus, parainfluenza virus, influenza A virus, influenza B virus, influenza C virus, Measles virus, Mumps virus, Rubella virus, Pneumovirus, Human respiratory syncytial virus, Rabies virus, California encephalitis virus, Japanese encephalitis virus, Hantaan virus, Lymphocytic choriomeningitis virus, Coronavirus, Enterovirus, Rhinovirus, Poliovirus, Norovirus, Flavivirus, Dengue virus, West Nile virus, Yellow fever virus and varicella.

In one embodiment, a composition of the invention may be used to treat and/or prevent an influenza virus infection in a subject in need thereof. Influenza is a single-stranded RNA virus of the family Orthomyxoviridae and is often characterized based on two large glycoproteins on the outside of the viral particle, hemagglutinin (HA) and neuraminidase (NA). Numerous HA subtypes of influenza A have been identified (Kawaoka et al., Virology (1990) 179: 759-767; Webster et al., "Antigenic variation among type A influenza viruses," p. 127-168. In: P. Palese and D. W. Kingsbury (ed.), Genetics of influenza viruses. Springer-Verlag, New York).

A composition of the invention may be suitable for use in the treatment and/or prevention of a neurodegenerative disease in a subject in need thereof, wherein the neurodegenerative disease is associated with the expression of an antigen. The subject may have a neurodegenerative disease or may be at risk of developing a neurodegenerative disease. Neurodegenerative diseases that may be treated and/or prevented by the use or administration of a composition of the invention include, without limitation, Alzheimer's disease, Parkinson's disease, Huntington's disease, and amyotrophic lateral sclerosis (ALS).

In one embodiment, a composition of the invention may be used to treat and/or prevent Alzheimer's disease in a subject in need thereof. Alzheimer's disease is characterized by the association of β-amyloid plaques and/or tau proteins in the brains of patients with Alzheimer's disease (see, for example, Goedert and Spillantini, Science, 314: 777-781, 2006). Herpes simplex virus type 1 has also been proposed to play a causative role in people carrying the susceptible versions of the apoE gene (Itzhaki and Wozniak, J Alzheimers Dis 13: 393-405, 2008).

A subject administered or treated with a composition of the invention may result in the increase of an antibody and/or cell mediated immune response to the antigen relative to a subject treated with a control composition. As used herein, a "control composition" may refer to any composition that does not contain at least one component of the claimed composition. Thus a control composition does not contain at least one of 1) an antigen, 2) liposome, 3) polyI:C or 4) a hydrophobic carrier. In one embodiment, a control composition does not contain polyI:C. In other embodiments, a control composition may contain alum instead of polyI:C.

A subject administered or treated with a composition of the invention may elicit an antibody immune response that is at least 1.50×, at least 1.75×, at least 2×, at least 2.5×, at least 3×, at least 3.5×, at least 4×, at least 4.5×, or at least 5× higher relative to a subject treated with a control composition. In one embodiment, the antibody titre (expressed in terms of log 10 value) from the serum of a subject treated with a composition of the invention is at least 0.05, at least 0.10, at least 0.15, at least 0.20, at least 0.25 or at least 0.30 higher than that of a subject treated with a control composition.

A subject administered or treated with a composition of the invention may elicit a cell mediated immune response that is at least 1.50×, at least 1.75×, at least 2×, at least 2.5×, at least 3×, at least 3.5×, at least 4×, at least 4.5×, or at least 5× higher relative to a subject treated with a control composition.

A subject administered or treated with a composition of the invention may elicit a memory T cell population that is at least 1.50×, at least 1.75×, at least 2×, at least 2.5×, at least 3×, at least 3.5×, at least 4×, at least 4.5×, or at least 5× higher relative to a subject treated with a control composition.

A subject administered or treated with a composition of the invention may prevent the development and/or delay the onset of a tumor in a subject, relative to a subject treated with a control composition.

The invention is further illustrated by the following non-limiting examples.

Example 1

Pathogen free, female CD1 mice, 6-8 weeks of age, were obtained from Charles River Laboratories (St Constant, QC, Canada) and were housed according to institutional guidelines with water and food ad libitum, under filter controlled air circulation.

The H5N1 recombinant hemagglutinin protein, was purchased from Protein Sciences (Meridien, Conn., USA). This recombinant protein has an approximate molecular weight of 72,000 daltons and corresponds to the hemagglutinin glycoprotein, an antigenic protein present on the surface of the H5N1 influenza virus. This recombinant protein, hereafter designated rHA, was used as a model antigen to test the efficacy of vaccine formulations. rHA was used at 1 microgram per 30 microliter dose.

Vaccine efficacy was assessed by enzyme-linked immunosorbent assay (ELISA), a method that allows the detection of antigen-specific antibody levels in the serum of immunized animals. Performing the ELISA on sera collected from immunized mice on a regular interval (every four weeks for example), is useful for monitoring the antibody responses to a given vaccine formulation. Briefly, a 96-well microtiter plate is coated with antigen (rHA, 1 microgram/milliliter) overnight at 4 degrees Celsius, blocked with 3% gelatin for 30 minutes, then incubated overnight at 4 degrees Celsius with serial dilutions of sera, typically starting at a dilution of 1/2000. A secondary reagent (protein G conjugated to alkaline phosphatase, EMD chemicals, Gibbstown, N.J., USA) is then added to each well at a 1/500 dilution for one hour at 37 degrees Celsius. Following a 60 minute incubation with a solution containing 1 milligram/milliliter 4-nitrophenyl phosphate disodium salt hexahydrate (Sigma-Aldrich Chemie GmbH, Switzerland), the 405 nanometer absorbance of each well is measured using a microtiter plate reader (ASYS Hitech GmbH, Austria). Endpoint titers are calculated as described in Frey A. et al (Journal of Immunological Methods, 1998, 221:35-41). Calculated titers represent the highest dilution at which a statistically significant increase in absorbance is observed in serum samples from immunized mice versus serum samples from naïve, non-immunized control mice. Titers are presented as log 10 values of the endpoint dilution.

To formulate vaccine described herein, a 10:1 w:w homogenous mixture of S100 lecithin and cholesterol (Lipoid GmbH, Germany) was hydrated in the presence of a rHA solution in phosphate buffered saline (pH 7.4) to form liposomes with encapsulated rHA. In brief, 33 micrograms of rHA were first suspended in 300 microliters of phosphate buffered saline (pH 7.4) then added to 132 milligrams of the S100 lecithin/cholesterol mixture to form approximately 450 microliters of a liposome suspension encapsulating the rHA antigen. The liposome preparation was extruded by passing the material through a manual mini-extruder (Avanti, Alabaster, Ala., USA) fitted with a 200 nanometer polycarbonate membrane. For every 450 microliters of liposome suspension containing rHA, two milligrams of Imject Alum adjuvant (Pierce, Rockford, Ill., USA) was added. For every 500 microliters of a liposome/antigen/adjuvant suspension, an equal volume of a mineral oil carrier equivalent to Freund's incomplete adjuvant (known as Montanide™ ISA 51, supplied by Seppic, France) was added to form a water-in-oil emulsion with the liposome suspension contained within the water phase of the emulsion and the oil forming a continuous hydrophobic phase. Each vaccine dose consisted of 30 microliters of the above-described emulsion containing liposomes, rHA antigen, alum adjuvant, and the mineral oil carrier. This vaccine formulation will be referred to as liposome/alum/hydrophobic carrier.

To formulate the vaccine corresponding to the invention, the same procedures described above were used with the following exception: following the formation of liposomes encapsulating rHA, and after extruding the liposome suspension through a 200 nanometer polycarbonate membrane, 133 micrograms of polyI:C adjuvant (Pierce, Rockford, Ill., USA) were added to every 450 microliters of liposomes. For every 500 microliters of a liposome/antigen/adjuvant suspension, an equal volume of a mineral oil carrier (Montanide™ ISA 51, Seppic, France) was added to form a water-in-oil emulsion with the liposome suspension contained in the water phase of the emulsion and the oil forming the continuous phase. Each vaccine dose consisted of 30 microliters of the above described emulsion containing liposomes, rHA antigen, polyI:C adjuvant, and the mineral oil carrier. This particular formulation will be referred to as liposome/polyI:C/hydrophobic carrier.

The efficacy of the two emulsion formulations described above was compared to the efficacy of a control vaccine consisting of 1 microgram of rHA and 60 micrograms of alum adjuvant in 30 microliters of phosphate buffered saline (pH 7.4). Two groups of mice (9 or 10 mice per group) were injected once (no boosting) with liposome vaccine formulations, intramuscularly, as follows: Group 1 mice were vaccinated with Vaccine B comprising 1 microgram of rHA antigen formulated in 30 microliters of liposome/polyI:C/hydrophobic carrier as described above. Each vaccine dose effectively contained 4 micrograms of polyI:C. Group 2 mice were vaccinated with Vaccine A comprising 1 microgram of rHA formulated in 30 microliters of liposome/alum/hydrophobic carrier as described above. Each vaccine dose effectively contained 60 micrograms of alum. The control group of mice (Group 3, n=10) was injected intramuscularly with the control alum vaccine consisting of 1 microgram of rHA and 60 micrograms of alum suspended in phosphate buffered saline. Serum samples were collected from all mice at 18 days and 28 days post-immunization. Antibody titers in these sera were examined by ELISA as described above.

Group 3 mice generated a detectable antigen-specific antibody response as was expected following the administration of an alum-adjuvanted control vaccine. Not surprisingly, Group 2 mice vaccinated with a liposome/alum/hydrophobic carrier formulation generated a considerably higher antibody response. While these results were expected, the use of polyI:C adjuvant instead of alum adjuvant in a liposome/polyI:C/hydrophobic carrier formulation (Group 1 mice), yielded some unexpected result; antibody titers were significantly higher than those generated by the liposome/alum/hydrophobic carrier formulation (Group 2).

Group 3 mice, vaccinated with the aqueous control formulation described above, generated endpoint titers up to 1/32,000 and 1/64,000 at 18 and 28 days post-vaccination (log 10 values of 4.51 and 4.81 respectively). The endpoint titers at 18 and 28 days post-vaccination in Group 2 were up to 1/256,000 (log 10 value of 5.41). The presence of such antibody responses at 18 and 28 days (4 weeks) post-vaccination confirms that a genuine immune response was generated as a result of vaccination. Group 1 mice that were injected with the formulation corresponding to the invention were able to generate an enhanced immune response with endpoint titers reaching up to 1/1,024,000 (log 10 value of 6.01) at 18 days post-vaccination and 1/8,192,000 (a log 10 value of 6.91) at four weeks post-immunization. These results indicate that liposome/hydrophobic carrier formulations containing a polyI:C adjuvant are capable of generating a significantly enhanced in vivo immune response compared to liposome/alum/hydrophobic carrier and aqueous/alum control vaccinations.

Example 2

Pathogen free, female CD1 mice, 6-8 weeks of age, were obtained from Charles River Laboratories (St Constant, QC, Canada) and were housed according to institutional guidelines with water and food ad libitum, under filter controlled air circulation.

As in example 1, H5N1 recombinant hemagglutinin protein, corresponding to the hemagglutinin glycoprotein on the surface fo the H5N1 influenza virus, was purchased from Protein Sciences (Meridien, Conn., USA). This recombinant protein, hereafter designated rHA, was used as a model antigen to test the efficacy of vaccine formulations. rHA was used at 1 microgram per 30 microliter dose.

To formulate the vaccine corresponding to the invention, the same procedures as described in example one were used. In summary, 33 micrograms of rHA were suspended in 300 microliters of phosphate buffered saline (pH 7.4) then added to 132 milligrams of a S100 lecithin/cholesterol mixture (Lipoid GmbH, Germany) to form approximately 450 microliters of a liposome suspension encapsulating the rHA antigen. The liposome preparation was extruded by passing the material through a manual mini-extruder (Avanti, Alabaster, Ala., USA) fitted with a 200 nanometer polycarbonate membrane. For every 450 microliters of liposome suspension containing rHA, 133 micrograms of polyI:C adjuvant (Pierce, Rockford, Ill., USA) was added. For every 500 microliters of a liposome/antigen/adjuvant suspension, an equal volume of a mineral oil carrier (Montanide™ ISA 51, Seppic, France) was added to form a water-in-oil emulsion with the liposome suspension contained within the water phase of the emulsion and the oil forming a continuous hydrophobic phase. Each vaccine dose consisted of 30 microliters of the above described emulsion containing liposomes, rHA antigen, polyI:C adjuvant, and the mineral oil carrier. This particular formulation will be referred to as liposome/polyI:C/hydrophobic carrier.

The efficacy of the liposome/polyI:C/hydrophobic carrier vaccine described above was compared to the efficacy of an aqueous control vaccine containing polyI:C adjuvant. Two groups of mice (9 or 10 mice per group) were injected once, intramuscularly, with 30 microliters per dose. Group 1 mice were vaccinated with Vaccine B comprising 1 microgram of rHA and 4 micrograms of polyI:C formulated in 30 microliters of liposome/polyI:C/hydrophobic carrier as described above. Group 2 mice were injected with 30 microliters of the control polyI:C vaccine comprising 1 microgram rHA and 4 micrograms polyI:C formulated in phosphate buffered saline (pH 7.4). Serum samples were collected from all mice at 18 and 28 days post-immunization. rHA antibody titers of the sera samples were examined by ELISA as described in example 1.

Group 2 mice generated a detectable antigen-specific antibody response following the administration of a polyI:C-adjuvanted control vaccine. Group 1 mice, vaccinated with the liposome/polyI:C/hydrophobic carrier formulation, yielded significantly enhanced endpoint titers compared to those of Group 2. Group 2 mice generated titers up to 1/128,000 (log 10 value of 5.11) at 18 days post-vaccination and up to 1/1,024,000 (log 10 equal to 6.01) at 28 days (4 weeks) post-vaccination. As noted in example 1, the presence of such antibody responses confirms a genuine immune response generated as a result of the vaccination. Group 1 mice, vaccinated with the vaccine corresponding to the invention, were able to generate endpoint titers reaching up to 1/1,024,000 (log 10 value of 6.01) at 18 days post-vaccination and 1/8,192,000 (a log 10 value of 6.91) at four weeks post-immunization. These results indicate that liposome/hydrophobic carrier formulations containing a polyI:C adjuvant are capable of generating a significantly enhanced in vivo immune response compared to an aqueous/polyI:C control vaccination.

Example 3

Pathogen free, female CD1 mice, 6-8 weeks of age, were obtained from Charles River Laboratories (St Constant, QC, Canada) and were housed according to institutional guidelines with water and food ad libitum, under filter controlled air circulation.

As in examples 1 and 2, H5N1 recombinant hemagglutinin protein, corresponding to the hemagglutinin glycoprotein on the surface of the H5N1 influenza virus, was purchased from Protein Sciences (Meridien, Conn., USA). This recombinant protein, hereafter designated rHA, was used as a model antigen to test the efficacy of vaccine formulations. rHA was used at 1 microgram per 50 microliter dose.

To formulate vaccine corresponding to the invention, a 10:1 w:w homogenous mixture of S100 lecithin and cholesterol (Lipoid GmbH, Germany) was hydrated in the presence of a rHA and polyI:C adjuvant (Pierce, Rockford, Ill., USA) solution in phosphate buffer to form liposomes with encapsulated rHA and adjuvant. In brief, 20 micrograms of rHA and 200 micrograms polyI:C were first suspended in 250 microliters of 50 millimolar phosphate buffer (pH 7.4) then added to 132 milligrams of the S100 lecithin/cholesterol mixture to form approximately 400 microliters of a liposome suspension encapsulating the rHA antigen and polyI:C adjuvant. The liposome preparation was diluted in half using 50 millimolar phosphate buffer (pH 7.4) and then extruded by passing the material through a manual mini-extruder (Avanti, Alabaster, Ala., USA) fitted with a 200 nanometer polycarbonate membrane. Sized liposomes were then lyophilized using the Virtis Advantage freeze dryer (SP Industries, Warminister, Pa., USA). For every 800 microliters of original liposome suspension containing rHA and polyI:C, one milliliter of a mineral oil carrier equivalent to Freund's incomplete adjuvant (known as Montanide™ ISA 51, supplied by Seppic, France) was used to reconstitute the lyophilized liposomes. Each vaccine dose consisted of 50 microliters of the above described formulation combining liposomes, rHA antigen, polyI:C adjuvant, and the mineral oil carrier. This vaccine formulation will be referred to as lyophilized liposome/polyI:C/hydrophobic carrier.

The efficacy of the lyophilized liposome formulation described above was compared to the efficacy of a control vaccine consisting of 1 microgram of rHA and 100 micrograms of Imject Alum adjuvant (Pierce, Rockford, Ill., USA) in 50 microliters of 50 millimolar phosphate buffer (pH 7.4). Group 1 mice (N=8) were injected once (no boosting) with Vaccine C comprising 1 microgram of rHA antigen and 10 micrograms of polyI:C adjuvant formulated in 50 microliters of lyophilized liposome/polyI:C/hydrophobic carrier as described above. Group 2 mice (N=9) were vaccinated twice (day 0 and day 21) with the control alum vaccine comprising 1 microgram of rHA and 100 micrograms of alum adjuvant suspended in 50 millimolar phosphate buffer. Serum samples were collected from all mice at 3, 4, and 8 weeks post-immunization. rHA antibody titers in these sera were examined by ELISA as described in example 1.

Group 2 mice generated a detectable antigen-specific antibody response following the administration of an alum-adjuvanted control vaccine. Group 1 mice, vaccinated with a single dose of the lyophilized liposome/polyI:C/hydrophobic carrier formulation, yielded significantly enhanced endpoint titers compared to those of Group 2, despite that Group 2 animals were vaccinated twice (primary immunization plus boost). Group 2 mice generated titers up to 1/128,000 (log 10 value of 5.11) at three weeks post-vaccination (before boost) and up to 1/1,024,000 (log 10 equal to 6.01) and 1/512,000 (log 10 equal to 5.71) at four and eight weeks respectively (after boost). As noted in example 1, the presence of such antibody responses confirms a genuine immune response generated as a result of the vaccination. Group 1 mice, vaccinated with the vaccine corresponding to the invention, were able to generate endpoint titers reaching up to 1/2,048,000 (log 10 value of 6.31) at three weeks post-vaccination and 1/8,192,000 (a log 10 value of 6.91) at four and eight weeks post-immunization. These results indicate that single dose lyophilized liposome/hydrophobic carrier formulations containing a polyI:C adjuvant are capable of generating a significantly enhanced in vivo immune response compared to a boosted, aqueous alum control vaccination. The immune responses generated in this example are equivalent to the immune responses generated by a vaccine of the invention presented in Examples 1 and 2.

Example 4

Pathogen free, female CD1 mice, 6-8 weeks of age, were obtained from Charles River Laboratories (St Constant, QC, Canada) and were housed according to institutional guidelines with water and food ad libitum, under filter controlled air circulation.

As in the previous examples, H5N1 recombinant hemagglutinin protein (Protein Sciences, Meridien, Conn., USA) corresponding to the hemagglutinin glycoprotein present on the surface of the H5N1 influenza virus, hereafter designated rHA, was used as a model antigen to test the efficacy of vaccine formulations. rHA was used at 1 microgram per 30 microliter dose.

Vaccines described herein were formulated as described in Example 1. Briefly, 33 micrograms of rHA were suspended in 300 microliters of phosphate buffered saline (pH 7.4) then added to 132 milligrams of a homogeneous (10:1, w:w) S100 lecithin/cholesterol mixture (Lipoid GmbH, Germany) to form approximately 450 microliters of a liposome suspension encapsulating the rHA antigen. The liposome preparation was extruded by passing the material through a manual mini-extruder (Avanti, Alabaster, Ala., USA) fitted with a 200 nanometer polycarbonate membrane. For every 450 microliters of liposome suspension containing rHA, two milligrams of Imject Alum adjuvant (Pierce, Rockford, Ill., USA) was added. For every 500 microliters of a liposome/antigen/adjuvant suspension, an equal volume of a mineral oil carrier (Montanide™ ISA 51, supplied by Seppic, France) was added to form a water-in-oil emulsion with the liposome suspension contained within the water phase of the emulsion and the oil forming a continuous hydrophobic phase. Each vaccine dose consisted of 30 microliters of the above described emulsion containing liposomes, rHA antigen, alum adjuvant, and the mineral oil carrier. This vaccine formulation will be referred to as liposome/alum/hydrophobic carrier.

To formulate the vaccine corresponding to the invention, the same procedures as described above were used with the following exception: following the formation of liposomes encapsulating rHA, and after extruding the liposome suspension through a 200 nanometer polycarbonate membrane, 133 micrograms of RNA-based polyI:C adjuvant (Pierce, Rockford, Ill., USA) were added to every 450 microliters of liposomes. For every 500 microliters of a liposome/antigen/adjuvant suspension, an equal volume of a mineral oil carrier (Montanide™ ISA 51, Seppic, France) was added to form a water-in-oil emulsion with the liposome suspension contained in the water phase of the emulsion and the oil forming the continuous phase. Each vaccine dose consisted of 30 microliters of the above described emulsion containing liposomes, rHA antigen, polyI:C adjuvant, and the mineral oil carrier. This particular formulation will be referred to as liposome/polyI:C/hydrophobic carrier.

The efficacy of the two emulsion formulations described above was compared as described in Example 1. Two groups of mice (9 or 10 mice per group) were injected once (no boosting) with liposome vaccine formulations, intramuscularly, as follows: Group 1 mice were vaccinated with Vaccine B comprising 1 microgram of rHA antigen and 4 micrograms of polyI:C adjuvant formulated in 30 microliters of liposome/polyI:C/hydrophobic carrier (the invention). Group 2 mice were vaccinated with 1 microgram of rHA and 60 micrograms of alum adjuvant formulated in 30 microliters of liposome/alum/hydrophobic carrier. Group 2 vaccine was a control formulation (Vaccine A) containing the generic adjuvant alum. Serum samples were collected from all mice at 18 and 28 days post-immunization and then every four weeks for a total of 16 weeks. Antibody titers in these sera were examined by ELISA as described in Example 1.

The endpoint titers in Group 2 were up to 1/256,000 at 8 and 12 weeks and 1/512,000 at 16 weeks post-immunization (log 10 values of 5.41 and 5.71 respectively). Group 1 mice that were injected with the formulation corresponding to the invention were able to generate an enhanced immune response with endpoint titers reaching up to 1/4,096,000 (log 10 value of 6.61) at 8, 12 and 16 weeks post-vaccination. These results confirm that liposome/hydrophobic carrier formulations containing a polyI:C adjuvant are capable of generating a significantly enhanced in vivo immune response that is on average 10 times greater than what is achieved using a control vaccine lacking polyI:C (P values<than 0.01 at all time points between weeks 4 and 16 post-vaccination). The dramatic improvement in the immune response generated was a result of using the polyI:C adjuvant specifically instead of alum in the antigen/liposome/adjuvant/mineral oil carrier composition. The stronger immune response generated with the vaccine of this invention was robust, as it persisted at significantly superior levels compared to the alum containing vaccine for a minimum of 16 weeks.

Example 5

Pathogen free, female CD1 mice, 6-8 weeks of age, were obtained from Charles River Laboratories (St Constant, QC, Canada) and were housed according to institutional guidelines with water and food ad libitum, under filter controlled air circulation.

As in the previous examples, H5N1 recombinant hemagglutinin protein, corresponding to the hemagglutinin glycoprotein on the surface of the H5N1 influenza virus, was purchased from Protein Sciences (Meridien, Conn., USA). This recombinant protein, hereafter designated rHA, was used as a model antigen to test the efficacy of vaccine formulations. rHA was used at 1 microgram per 30 microliter dose.

To formulate the vaccine corresponding to the invention, the same procedures as described in Example 2 were used. In summary, 33 micrograms of rHA were suspended in 300 microliters of phosphate buffered saline (pH 7.4) then added to 132 milligrams of a S100 lecithin/cholesterol mixture (Lipoid GmbH, Germany) to form approximately 450 microliters of a liposome suspension encapsulating the rHA antigen. The liposome preparation was extruded by passing the material through a 200 nanometer polycarbonate membrane. For every 450 microliters of liposome suspension containing rHA, 133 micrograms of RNA-based polyI:C adjuvant (Pierce, Rockford, Ill., USA) was added. For every 500 microliters of a liposome/antigen/adjuvant suspension, an equal volume of a mineral oil carrier (Montanide™ ISA 51, Seppic, France) was added to form a water-in-oil emulsion with the liposome suspension contained within the water phase of the emulsion and the oil forming the continuous phase. Each vaccine dose consisted of 30 microliters of the above described emulsion containing liposomes, rHA antigen, polyI:C adjuvant, and the mineral oil carrier. This particular formulation will be referred to as liposome/polyI:C/hydrophobic carrier.

The efficacy of the liposome/polyI:C/hydrophobic carrier vaccine described above was compared to the efficacy of an aqueous control vaccine containing rHA antigen and RNA-based polyI:C adjuvant. Two groups of mice (9 or 10 mice per group) were injected once, intramuscularly, with 30 microliters per dose. Group 1 mice were vaccinated with Vaccine B comprising 1 microgram of rHA and 4 micrograms of polyI:C formulated as liposome/polyI:C/hydrophobic carrier as described above. Group 2 mice were injected with the control polyI:C vaccine comprising 1 microgram rHA and 4 micrograms polyI:C formulated in phosphate buffered saline (pH 7.4). Serum samples were collected from all mice at 18 and 28 days post-immunization and then every four weeks for a total of 16 weeks. rHA antibody titers of the sera samples were examined by ELISA as described in Example 1.

Group 2 mice generated a detectable, antigen-specific antibody response following the administration of a polyI:C-adjuvanted control vaccine. Group 1 mice, vaccinated with the liposome/polyI:C/hydrophobic carrier formulation, yielded significantly enhanced endpoint titers compared to those of Group 2. Group 2 mice generated titers up to 1/512,000 (log 10 value of 5.71) at 8 weeks and up to 1/2,048,000 (log 10 equal to 6.31) at 12 and 16 weeks post-vaccination. As noted previously, the presence of such antibody responses confirms a genuine immune response generated as a result of the vaccination. Group 1 mice, vaccinated with the vaccine corresponding to the invention, were able to generate endpoint titers reaching up to 1/4,096,000 (log 10 value of 6.61) at 8, 12 and 16 weeks post-immunization. These results confirm that liposome/hydrophobic carrier formulations containing a polyI:C adjuvant are capable of generating a durable and substantially higher in vivo immune response compared to an aqueous/polyI:C control vaccination (P value<0.02 at week 4 and week 16 post-vaccination). Antibody titers that were 7 times higher on average at early (week 4 post vaccination) and 9 times higher on average at late (week 16 post-vaccination) time points were achieved in the presence of liposomes and a hydrophobic carrier in the vaccine. This suggests that the liposome and hydrophobic carrier components are important for generating the strong immune responses observed.

Example 6

Pathogen free, female BALB/c mice, 6-8 weeks of age, were obtained from Charles River Laboratories (St Constant, QC, Canada) and were housed according to institutional guidelines with water and food ad libitum, under filter controlled air circulation.

As in Examples 1 through 5, H5N1 recombinant hemagglutinin protein, corresponding to the hemagglutinin glycoprotein on the surface of the H5N1 influenza virus, was purchased from Protein Sciences (Meridien, Conn., USA). This recombinant protein, hereafter designated rHA, was used as a model antigen to test the efficacy of vaccine formulations. rHA was used at 1.5 micrograms per 50 microliter dose.

To formulate vaccine corresponding to the invention, a 10:1 (w:w) homogenous mixture of S100 lecithin and cholesterol (Lipoid GmbH, Germany) was hydrated in the presence of rHA in phosphate buffer to form liposomes with encapsulated rHA and followed by the addition of polyI:C (Pierce, Rockford, Ill., USA). In brief, 30 micrograms of rHA were suspended in 750 microliters of 50 millimolar phosphate buffer (pH 7.0) then added to 132 milligrams of the S100 lecithin/cholesterol mixture to form approximately 900 microliters of a liposome suspension encapsulating the rHA antigen. The liposome preparation was extruded by passing the material through a semi-automatic extruder (Avestin, Ottawa, ON, Canada) fitted with a 200 nanometer polycarbonate membrane at a flow rate of 100 milliliters per minute. 250 micrograms of RNA-based polyI:C adjuvant in 50 millimolar phosphate buffer (pH 7.0) was added to sized liposomes to dilute the preparation to 1 milliliter. Liposomes were then lyophilized using the Virtis Advantage freeze dryer (SP Industries, Warminister, Pa., USA). For every 1 milliliter of original liposome suspension containing rHA and polyI:C, 800 microliters of a mineral oil carrier (Montanide™ ISA 51, Seppic, France) was used to reconstitute the lyophilized liposomes. Each vaccine dose consisted of 50 microliters of the above described formulation containing liposomes, rHA antigen, polyI:C adjuvant, and the mineral oil carrier. This vaccine formulation will be referred to as lyophilized liposome/polyI:C/hydrophobic carrier.

The efficacy of the lyophilized liposome formulation described above was compared to the efficacy of a control vaccine consisting of 1.5 micrograms of rHA and 100 micrograms of Imject Alum adjuvant (Pierce, Rockford, Ill., USA) in 50 microliters of 50 millimolar phosphate buffer (pH 7.0). Group 1 mice (N=10) were injected intramuscularly, once (no boosting), with Vaccine D comprising 1.5 micrograms of rHA antigen and 12.5 micrograms of RNA-based polyI:C adjuvant formulated in 50 microliters of lyophilized liposome/polyI:C/hydrophobic carrier as described above. Group 2 mice (N=10 at weeks 3 and 4 reduced to N=9 at weeks 6 and 9 due to unplanned non-vaccine related termination of one animal) were vaccinated twice (day 0 and day 28) with a control alum vaccine comprising 1.5 micrograms of rHA and 100 micrograms of alum adjuvant suspended in 50 millimolar phosphate buffer. Serum samples were collected from all mice at 3, 4, 6 and 9 weeks post-immunization. rHA antibody titers in these sera were examined by ELISA as described in Example 1.

Group 2 mice generated an antigen-specific antibody response only after the administration of 2 doses (primary immunization and boost) of an alum-adjuvanted control vaccine. Group 1 mice, vaccinated with a single dose of the lyophilized liposome/polyI:C/hydrophobic carrier formulation, yielded significantly enhanced endpoint titers compared to those of Group 2 at all time points tested despite that Group 2 animals were vaccinated twice. Group 2 mice recorded background titers 3 weeks after the primary vaccination and one individual generated a maximum titer of 1/8,000 (log 10 equal to 3.39) at 4 weeks. After the boost, Group 2 mice generated titers up to 1/64,000 (log 10 value of 4.81) at 6 and 9 weeks post-immunization. Group 1 mice, vaccinated with the vaccine corresponding to the invention, were able to generate endpoint titers up to 1/128,000 (log 10 of 5.11) at 3 and 4 weeks post-vaccination and 1/512,000 (a log 10 value of 5.71) at 6 and 9 weeks post-immunization. These results confirm, using a different mouse species than the one used in Example 3, that a single dose of lyophilized liposome/hydrophobic carrier formulations containing a polyI:C adjuvant is capable of generating a significantly enhanced in vivo humoral immune response compared to even a boosted, aqueous/alum control vaccination. Antibody levels were 24 times higher than a single dose of the control vaccine at week 4 post-vaccination (P value<0.001) and 9 times higher than two doses of the control vaccine at the later time point of 9 weeks post-vaccination (P value<0.01). Furthermore, results from Examples 3 and 6 indicate that the polyI:C adjuvant can be incorporated into the lyophilized liposome/hydrophobic carrier formulation either before or after liposome extrusion.

Example 7

Pathogen free, female BALB/c mice, 6-8 weeks of age, were obtained from Charles River Laboratories (St Constant, QC, Canada) and were housed according to institutional guidelines with water and food ad libitum, under filter controlled air circulation.

As in Examples 1 through 6, H5N1 recombinant hemagglutinin protein, corresponding to the hemagglutinin glycoprotein on the surface of the H5N1 influenza virus, was purchased from Protein Sciences (Meridien, Conn., USA). This recombinant protein, hereafter designated rHA, was used as a model antigen to test the efficacy of vaccine formulations. rHA was used at 1.5 micrograms per 50 microliter dose.

In this example, the lyophilized liposome/polyI:C/hydrophobic carrier was administered intramuscularly once (no boosting) or subcutaneously once (no boosting) to evaluate the generation of antigen-specific cytotoxic lymphocyte response.

To formulate the vaccine corresponding to the invention, the same procedures as described in Example 6 were used. In summary, liposomes were formulated by hydrating a 10:1 (w:w) homogeneous mixture of S100 lecithin and cholesterol (Lipoid GmbH, Germany) in the presence of rHA in phosphate buffer followed by the addition of RNA-based polyI:C (Pierce, Rockford, Ill., USA). The liposome suspension was lyophilized and resuspended in a mineral oil carrier (Montanide ISA 51™, SEPPIC, France). Each vaccine dose (Vaccine D) consisted of 50 microliters of the above described formulation containing liposomes (6.6 mg of 5100/cholestrol lipids), rHA antigen (1.5 micrograms), polyI:C adjuvant (12.5 micrograms), and the mineral oil carrier. This vaccine formulation will be referred to as lyophilized liposome/polyI:C/hydrophobic carrier. Mice in Group 1 (n=4) received this formulation intramuscularly as in Example 6. Group 2 mice (n=4) received this vaccine subcutaneously.

Mice in Group 3 (n=4) were vaccinated with the control alum vaccine consisting of 1.5 micrograms of rHA and 100 micrograms of Imject Alum adjuvant (Pierce, Rockford, Ill., USA) in 50 microliters of 50 millimolar phosphate buffer (pH 7.0). Mice were injected intramuscularly once (no boost). Group 4 mice (n=2) were naïve and did not receive any immunization.

Twenty-two days after vaccination, animals were euthanized by carbon dioxide induced asphyxiation. The spleens were collected and individual single cell suspensions prepared using standard procedures. Red blood cells were lysed using ACK lysis buffer (0.15 M NH4CI, 10 mM KHCO3, 0.1 mM Na2EDTA in distilled H20). To augment the antigen specific T cells, splenocytes were cultured at 1×10ˆ6 cells per millilitre in RPMI 1640 (Invitrogen, Burlington, ON, Canada) complete media containing 1% Penicillin/Streptomycin/Glutamine, 0.1% 2-mercaptoethanol (Sigma-Aldrich, St. Louis, Mo., USA), and 10% fetal bovine serum (Hyclone, Logan, Utah, USA) supplemented with 20 units per millilitre of recombinant human IL-2 (Sigma-Aldrich) and 10 micrograms per millilitre rHA for 4 days at 37° C., 5% carbon dioxide. Tri-colour flow cytometric analysis was performed on splenocytes to detect antigen-specific CD8+ T cells. Cells were blocked with a 10 minute treatment at room temperature of FC-block (eBioscience, San Diego, Calif., USA). Cells were then stained with phycoerythrin (PE)-labeled IYSTVASSL (I9L)/H2-Kd pentamer obtained from Proimmune (Bradenton, Fla., USA) for 20 minutes at 4° C. 19L is the H2-Kd immunodominant epitope of rHA (518-528), and the pentamer reagent detects MHC I presentation of this epitope by the mouse. Cells were then stained with anti-CD19-fluorescein isothiocyanate (FITC) (eBioscience) and anti-CD8β-Allophycocyanin (APC) (eBioscience) for 30 minutes at 4° C. protected from light, washed and fixed in 50 millimolar phosphate buffer (pH 7.0) with 0.1% paraformaldehyde. 5×10ˆ5 cells were acquired on a FACSCalibur™ flow cytometer (BD Bioscience, Missisauga, ON, Canada) and analysed using WinList 6.0 software (Verity Inc, Topsham, Me., USA). Results were gated based on forward and side scatter, and antigen-specific CD8 T cells were defined as pentamer positive, CD8β positive and CD19 negative. Statistical analysis was performed using two-tailed Students' T test.

Mice vaccinated with the control alum-based formulation generated a small population of antigen-specific CD8 T cells (0.045%). Mice vaccinated with the lyophilized liposome/polyI:C/hydrophobic carrier formulation of the present invention, delivered by the intramuscular or subcutaneous route, generated a significantly higher population of antigen-specific CD8 T cells (0.23% and 0.17% respectively; p=<0.025 for both compared to alum control). These results demonstrate that rHA formulated in the invention can be delivered intramuscularly or subcutaneously and generate a significantly higher antigen-specific CD8+ T cell population representative of a cellular immune response compared to a conventional vaccine formulation using alum.

Example 8

Pathogen free, female CD-1 mice, 6-8 weeks of age, and female New Zealand White rabbits, 2-3 kilograms in weight, were obtained from Charles River Laboratories (St Constant, QC, Canada) and were housed according to institutional guidelines with water and food ad libitum, under filtered air circulation.

As in Examples 1 through 7, H5N1 recombinant hemagglutinin protein, corresponding to the hemagglutinin glycoprotein on the surface of the H5N1 influenza virus, was purchased from Protein Sciences (Meridien, Conn., USA). This recombinant protein, hereafter designated rHA, was used as a model antigen to test the efficacy of vaccine formulations. rHA was used at 0.5 micrograms per 50 microliter dose in mice and 2 micrograms per 200 microliter dose in rabbits.

Vaccine efficacy was assessed by hemagglutination inhibition assays (HAI) conducted by Benchmark Biolabs (Lincoln, Nebr., USA). Briefly, serum samples were pre-treated with a receptor destroying enzyme and pre-absorbed to chicken red blood cells to avoid any non-specific hemagglutination inhibition reactions. Serial dilutions of sera were then incubated with 0.7% equine red blood cells, 0.5% bovine serum albumin and 8 HA units of A/Vietnam/1203/2004[H5N1] influenza virus. Calculated titers represent the highest dilution at which the serum sample can completely inhibit hemagglutination of the red blood cells.

To formulate the first vaccine corresponding to the invention, a 10:1 (w:w) homogenous mixture of S100 lecithin and cholesterol (Lipoid GmbH, Germany) was hydrated in the presence of rHA in phosphate buffer to form liposomes with encapsulated rHA and followed by the addition of RNA-based polyI:C (Pierce, Rockford, Ill., USA). Briefly, 10 micrograms of rHA were first suspended in 650 microliters of 50 millimolar phosphate buffer (pH 7.0) then added to 132 milligrams of the S100 lecithin/cholesterol mixture to form approximately 800 microliters of a liposome suspension encapsulating the rHA antigen. The liposome preparation was then extruded by passing the material through a manual mini-extruder (Avanti, Alabaster, Ala., USA) fitted with a 200 nanometer polycarbonate membrane. 240 micrograms of polyI:C adjuvant in 50 millimolar phosphate buffer (pH 7.0) were added to sized liposomes. Liposomes were then lyophilized using the Virtis Advantage freeze dryer (SP Industries, Warminister, Pa., USA). The lyophilized material was reconstituted with a mineral oil carrier (Montanide™ ISA 51, supplied by Seppic, France) up to the original 1 milliliter volume of solublized liposomes. Each vaccine dose as delivered to mice, consisted of 50 microliters of the above described formulation combining liposomes, rHA antigen, polyI:C adjuvant, and the mineral oil carrier. These vaccine formulations will be referred to as lyophilized liposome/polyI:C/hydrophobic carrier.

To formulate the second vaccine, also corresponding to the invention, the same procedures described above were used with the following exceptions: following the formation of liposomes encapsulating rHA antigen, the liposome preparation was extruded by passing the material through a manual mini-extruder fitted with two 400 nanometer polycarbonate membranes. 250 micrograms of the RNA-based polyI:C adjuvant in 50 millimolar phosphate buffer (pH 7.0) was added to sized liposomes to dilute the preparation to 1 milliliter. Liposomes were then lyophilized using the Virtis Advantage freeze dryer and the lyophilized material reconstituted to the original 1 milliliter using a mineral oil carrier (Montanide™ ISA 51, Seppic, France). Each vaccine dose delivered to rabbits consisted of 200 microliters of the above described formulation containing liposomes, rHA antigen, polyI:C adjuvant, and the mineral oil carrier. This vaccine formulation will also be referred to as lyophilized liposome/polyI:C/hydrophobic carrier.

The efficacy of the lyophilized liposome formulations described above was tested using two different animal models. Animals were vaccinated with comparable formulations; the injection volume was adjusted as appropriate for the size of the animals. One group of mice (N=5) were injected intramuscularly with Vaccine F comprising 0.5 micrograms of rHA antigen and 12 micrograms of polyI:C adjuvant formulated in 50 microliters of lyophilized liposome/polyI:C/hydrophobic carrier as described above. One group of rabbits (N=5) were injected subcutaneously with Vaccine E comprising 2 micrograms of rHA antigen and 50 micrograms of polyI:C adjuvant formulated in 200 microliters of lyophilized liposome/polyI:C/hydrophobic carrier as described above. All animals were bled before injection and then again at either 4 or 5 weeks post-immunization. HAI titers in these sera were examined by the H5N1 hemagglutination inhibition assay described above.

By 4 or 5 weeks post-vaccination with lyophilized liposome/polyI:C/hydrophobic carrier formulations both the mice and rabbits generated HAI titers that indicate protection against influenza H5N1. A HAI serum titer of 40 (log 10 equal to 1.60) is typically accepted to mean an individual has a protective level of antibodies targeting a specific strain of influenza. At 5 weeks post-vaccination mice generated titers ranging from 128 (log 10 of 2.11) to 512 (log 10 of 2.71). At 4 weeks post-immunization rabbits generated HAI titers ranging from 64 (log 10 equal to 1.81) up to 1024 (log 10 of 3.01). It is generally accepted that a single vaccination of rHA used at the dosages described above is incapable of inducing the high HAI titers achieved in all vaccinated subject. Titers of this magnitude, generated in two different animal models, show that the lyophilized liposome/polyI:C/hydrophobic carrier formulations is particularly effective in generating strong antibody levels in the protective range (HAI>20 or log value>1.3) in all vaccinated subject in as little as 4 weeks following vaccination.

Example 9

Pathogen free, female CD1 mice, 6-8 weeks of age, were obtained from Charles River Laboratories (St Constant, QC, Canada) and were housed according to institutional guidelines with water and food ad libitum, under filter controlled air circulation.

The amyloid β protein fragment (1-43) was purchased from Anaspec (San Jose, Calif., USA) and used as a model antigen to test the efficacy of vaccine formulations. This peptide, hereafter referred to as β-amyloid, has a molecular weight of approximately 4,600 daltons and is associated the formation of plaques in the brains of Alzheimer's patients. β-amyloid was used at 10 micrograms per 100 microliter dose.

The 21 amino acid peptide FNNFTVSFWLRVPKVSASHLE, hereafter referred to as F21E, was purchased from NeoMPS (San Diego, Calif., USA). This tetanus toxoid peptide (amino acids 947-967) is identified as being a T-helper epitope. F21E was used as a model T-helper epitope to test the efficacy of vaccine formulations; it was used at 20 micrograms per 100 microliter dose.

As in Examples 1 through 6, vaccine efficacy was assessed by enzyme-linked immunosorbent assay (ELISA). The same procedures as described in Example 1 were used with changes to allow for the detection of β-amyloid specific antibodies. Briefly, a 96-well microtiter plate is coated with antigen (β-amyloid, 1 microgram/milliliter) overnight at 4 degrees Celsius, blocked with 3% gelatin for 30 minutes, then incubated overnight at 4 degrees Celsius with serial dilutions of sera, typically starting at a dilution of 1/1000. A secondary reagent (protein G conjugated to alkaline phosphatase, EMD chemicals, Gibbstown, N.J., USA) is then added to each well at a 1/500 dilution for one hour at 37 degrees Celsius. Following a 60 minute incubation with a solution containing 1 milligram/milliliter 4-nitrophenyl phosphate disodium salt hexahydrate (Sigma-Aldrich Chemie GmbH, Switzerland), the 405 nanometer absorbance of each well is measured using a microtiter plate reader (ASYS Hitech GmbH, Austria). Endpoint titers are calculated as described in Frey A. et al (Journal of Immunological Methods, 1998, 221:35-41). Calculated titers represent the highest dilution at which a statistically significant increase in absorbance is observed in serum samples from immunized mice versus serum samples from naïve, non-immunized control mice. Titers are presented as log 10 values of the endpoint dilution.

To formulate vaccine described herein, a 10:1 w:w homogenous mixture of S100 lecithin and cholesterol (Lipoid GmbH, Germany) was hydrated in the presence of a β-amyloid and F21E solution in phosphate buffered saline (pH 7.4) to form liposomes with encapsulated antigen and T-helper. In brief, 100 micrograms of β-amyloid and 200 micrograms of F21E were first suspended in 300 microliters of phosphate buffered saline (pH 7.4) then added to 132 milligrams of the S100 lecithin/cholesterol mixture to form approximately 450 microliters of a liposome suspension encapsulating the β-amyloid antigen and F21E T-helper. The liposome preparation was extruded by passing the material through a manual mini-extruder (Avanti, Alabaster, Ala., USA) fitted with a 400 nanometer polycarbonate membrane. For every 450 microliters of liposome suspension containing β-amyloid and F21E, 2 milligrams of Imject Alum adjuvant (Pierce, Rockford, Ill., USA) was added. For every 500 microliters of a liposome/antigen/T-helper/adjuvant suspension, an equal volume of a mineral oil carrier (known as Montanide™ ISA 51, supplied by Seppic, France) was added to form a water-in-oil emulsion with the liposome suspension contained within the water phase of the emulsion and the oil forming a continuous hydrophobic phase. Each vaccine dose consisted of 100 microliters of the above-described emulsion containing liposomes, β-amyloid antigen, F21E T-helper, alum adjuvant, and the mineral oil carrier. This vaccine formulation will be referred to as liposome/alum/hydrophobic carrier.

To formulate the vaccine corresponding to the invention, the same procedures described above were used with the following exception: following the formation of liposomes encapsulating β-amyloid and F21E, and after extruding the liposome suspension through a 400 nanometer polycarbonate membrane, 100 micrograms of RNA-based polyI:C adjuvant (Pierce, Rockford, Ill., USA) were added to every 450 microliters of liposomes. For every 500 microliters of a liposome/antigen/T-helper/adjuvant suspension, an equal volume of a mineral oil carrier (Montanide™ ISA 51, Seppic, France) was added to form a water-in-oil emulsion with the liposome suspension contained in the water phase of the emulsion and the oil forming the continuous phase. Each vaccine dose consisted of 100 microliters of the above described emulsion containing liposomes, β-amyloid antigen, F21E T-helper, polyI:C adjuvant, and the mineral oil carrier. This particular formulation will be referred to as liposome/polyI:C/hydrophobic carrier.

The efficacy of the two emulsion formulations described above was compared. Two groups of mice (9 mice per group) were injected intraperitoneally with liposome vaccine formulations as follows: Group 2 mice were vaccinated with Vaccine G comprising 10 micrograms of β-amyloid and 20 micrograms of F21E formulated in 100 microliters of liposome/alum/hydrophobic carrier as described above. Each vaccine dose effectively contained 200 micrograms of alum. Group 1 mice were vaccinated with Vaccine H comprising 10 micrograms of β-amyloid antigen and 20 micrograms F21E formulated in 100 microliters of liposome/polyI:C/hydrophobic carrier as described above. Each vaccine dose effectively contained 10 micrograms of polyI:C. Serum samples were collected from all mice at 4, 8 and 12 weeks post-immunization. Antibody titers in these sera were examined by ELISA as described above.

Group 2 mice, vaccinated with a single dose of a liposome/alum/hydrophobic carrier formulation, generated a detectable antigen-specific antibody response as was expected. The endpoint titers at 4 and 8 weeks post-vaccination were up to 1/32,000 (log 10 value of 4.51) and at 12 weeks they were up to 1/64,000 (log 10 of 4.81). The presence of such antibody responses confirms that a genuine immune response was generated as a result of vaccination. Group 1 mice that were injected once with the formulation corresponding to the invention were able to generate an enhanced immune response with endpoint titers reaching up to 1/256,000 (log 10 value of 5.41) at 4, 8 and 12 weeks post-vaccination. The titers generated with the invention were 7 times higher on average at every time point relative to titers generated by the control formulation containing the generic adjuvant alum. The increase in titers achieved with the invention was statistically significant (P value<0.01 at weeks 8 and 12 post-vaccination). These results confirm through the use of a different antigen model that liposome/hydrophobic carrier formulations containing a polyI:C adjuvant are capable of generating a significantly enhanced in vivo immune response compared to a liposome/alum/hydrophobic vaccination.

Example 10

Pathogen free, female CD1 mice, 6-8 weeks of age, were obtained from Charles River Laboratories (St Constant, QC, Canada) and were housed according to institutional guidelines with water and food ad libitum, under filter controlled air circulation.

The H5N1 recombinant hemagglutinin protein was purchased from Protein Sciences (Meridien, Conn., USA). This recombinant protein has an approximate molecular weight of 72,000 daltons and corresponds to the hemagglutinin glycoprotein, an antigenic protein present on the surface of the H5N1 influenza virus. This recombinant protein, hereafter designated rHA, was used as a model antigen to test the efficacy of vaccine formulations. rHA was used at 0.5 micrograms per 50 microliter dose.

Both the humoral (TH1) and cellular (TH2) immune responses were assessed by enzyme-linked immunosorbent assay (ELISA), a method that allows the detection of antigen-specific antibody levels in the serum of immunized animals. Briefly, a 96-well microtiter plate is coated with antigen (rHA, 1 microgram/milliliter) overnight at 4 degrees Celsius, blocked with 3% gelatin for 30 minutes, then incubated overnight at 4 degrees Celsius with serial dilutions of sera, typically starting at a dilution of 1/2000. A secondary antibody, anti-IgG, is then added to each well at a 1/2000 dilution for one hour at 37 degrees Celsius. For the detection of IgG2A antibodies, indicative of a TH1 cellular response, goat anti-mouse IgG2A (SouthernBiotech, Birmingham, Ala., USA) was used. For the detection of a TH2 humoral response a goat anti-mouse IgG1 (SouthernBiotech, Birmingham, Ala., USA) secondary reagent was used. Following a 60 minute incubation with a solution containing 1 milligram/milliliter 4-nitrophenyl phosphate disodium salt hexahydrate (Sigma-Aldrich Chemie GmbH, Switzerland), the 405 nanometer absorbance of each well is measured using a microtiter plate reader (ASYS Hitech GmbH, Austria). Endpoint titers are calculated as described in Frey A. et al (Journal of Immunological Methods, 1998, 221:35-41). Calculated titers represent the highest dilution at which a statistically significant increase in absorbance is observed in serum samples from immunized mice versus serum samples from naïve, non-immunized control mice. Titers are presented as log 10 values of the endpoint dilution.

To formulate vaccines corresponding to the invention, a 10:1 w:w homogenous mixture of S100 lecithin and cholesterol (Lipoid GmbH, Germany) was hydrated in the presence of a rHA solution in phosphate buffer to form liposomes with encapsulated rHA and followed by the addition of RNA-based polyI:C (Pierce, Rockford, Ill., USA) as described in Example 8. In brief, 10 micrograms of rHA were first suspended in 650 microliters of 50 millimolar phosphate buffer (pH 7.0) then added to 132 milligrams of the S100 lecithin/cholesterol mixture to form approximately 800 microliters of a liposome suspension encapsulating the rHA antigen. The liposome preparation was then extruded by passing the material through a manual mini-extruder (Avanti, Alabaster, Ala., USA) fitted with a 200 nanometer polycarbonate membrane. PolyI:C adjuvant in 50 millimolar phosphate buffer (pH7.0) was added to sized liposomes to dilute the preparation to 1 milliliter. For the "high dose" polyI:C formulation, 240 micrograms of polyI:C in phosphate buffer was added and for the "low dose" polyI:C formulation 50 micrograms of polyI:C were added. Liposomes were then lyophilized using the Virtis Advantage freeze dryer (SP Industries, Warminister, Pa., USA). The lyophilized material was reconstituted with a mineral oil carrier (Montanide™ ISA 51, supplied by Seppic, France) up to the original 1 milliliter volume of solublized liposomes. Each vaccine dose consisted of 50 microliters of the above described formulation combining liposomes, rHA antigen, polyI:C adjuvant, and the mineral oil carrier. These vaccine formulations will be referred to as lyophilized liposome/polyI:C (high)/hydrophobic carrier and lyophilized liposome/polyI:C (low)/hydrophobic carrier.

The TH1 and TH2 responses generated, as a result of vaccination with the lyophilized liposome formulations containing polyI:C adjuvant, were compared. Two groups of mice (N=5 per groups) were injected intramuscularly with 50 microliters of either Vaccine E comprising 0.5 micrograms rHA and 12 micrograms polyI:C formulated as lyophilized liposomes/polyI:C (high)/hydrophobic carrier (Group 1) or Vaccine I comprising 0.5 micrograms rHA and 2.5 micrograms polyI:C formulated as lyophilized liposomes/polyI:C (low)/hydrophobic carrier (Group 2). Serum samples were collected at 5 weeks post-immunization and IgG1 and IgG2A antibody titers examined as described above.

Group 1 mice generated IgG1 titres up to 2,048,000 (log 10 value of 6.31) at 5 weeks post-immunization which is comparable to the humoral response results of the similar lyophilized liposomes/polyI:C/hydrophobic carrier formulation used in Example 3. The IgG2A titers, indicative of a cellular response, were up to 4,096,000 (log 10 equal to 6.61) at 5 weeks post-vaccination. Group 2 mice, vaccinated with a lower dose of polyI:C, generated at 5 weeks post-vaccination IgG1 titers up to 4,096,000 (log 10 of 6.61) and IgG2A titers also up to 4,096,000. Results show that polyI:C adjuvant formulated at various concentrations in a lyophilized liposome/hydrophobic carrier formulation is able to generate both humoral (TH2) and cellular (TH1) immune responses. These results suggest that the formulations described above are capable of generating cellular and humoral immune responses in vaccinated subjects.

Example 11

Pathogen free, female C57BL6 mice, 4-6 weeks of age, were obtained from Charles River Laboratories (St Constant, QC, Canada) and were housed according to institutional guidelines with water and food ad libitum, under filter controlled air circulation.

The antigen used in vaccine formulations was a fusion protein consisting of the H2-Db immunodominant epitope of HPV16 E7 (49-57; RAHYNIVTF) fused to the universal T helper epitope PADRE. This antigen, hereafter referred to as FP, was synthesized by Anaspec Inc. (San Jose, Calif.). The adjuvant was a RNA-based poly inosine-cytosine RNA molecule provided by Sigma-Genosys (St. Louis, Mo.).

The efficacy of the invention comprising liposomes, an RNA-based poly I:C molecule, and a hydrophobic carrier was tested in vivo using a C3 tumor challenge model. C3 cells contain the human papilloma virus 16 (HPV16) genome and as a result, present on their surface the HPV16 E7 epitope (amino acids 49-57; RAHYNIVTF) which can be targeted by vaccination. C3 cells grow into measurable solid tumors when injected subcutaneously. Three groups of mice (n=8 per group) were implanted subcutaneously in the flank with the HPV16 E7 expressing tumor cell line C3 ($5\times10^5$ cells/mouse) on day 0. On day 8, mice in Groups 1 and 2 were vaccinated subcutaneously in the opposing flank with 100 microliters of vaccine. Group 3 mice received PBS only and served as the tumor growth control. Tumor volume was measured once a week using callipers to record the shortest diameter and longest diameter for 5 weeks post implantation. Tumor volume was calculated using the following formula: longest measurement×(shortest measurement)^2 divided by 2.

The control vaccine (conventional emulsion) used to immunize Group 1 was formulated by mixing 300 micrograms of FP antigen and 3 milligrams of PolyI:C adjuvant in 1 millilitre of PBS. For every 500 microliters of antigen/adjuvant suspension, an equal volume of a mineral oil carrier (Montanide™ ISA 51, supplied by Seppic, France) was added to form a water-in-oil emulsion. Each vaccine dose consisted of 100 microliters of the described emulsion containing FP antigen (15 micrograms) and polyI:C adjuvant (150 micrograms) and the mineral oil carrier. This vaccine formulation will be referred to as polyI:C/hydrophobic carrier.

To formulate vaccine (Vaccine K) corresponding to the invention for Group 2, the same procedures as described in Example 1 were used. Briefly, 150 micrograms of FP antigen was mixed with a DOPC lecithin/cholesterol mixture (10:1, w:w; Lipoid GmbH, Germany) dissolved in tert-butanol and lyophilized. Liposomes were formulated by adding 1 millilitre of 50 millimolar phosphate buffer (pH 7.0) containing 1.5 milligrams of polyI:C. The liposome preparation was extruded by passing the material through a manual mini-extruder (Avanti, Alabaster, Ala., USA) fitted with a 200 nanometer polycarbonate membrane. Liposome size was confirmed at 200 nanometers using a Malvern Particle Size Analyzer (Worchestershire, United Kingdom). For every 500 microliters of a liposome/antigen/adjuvant suspension, an equal volume of a mineral oil carrier (Montanide™ ISA 51, supplied by Seppic, France) was added to form a water-in-oil emulsion with the liposome suspension contained within the water phase of the emulsion and the oil forming a continuous hydrophobic phase. Each vaccine dose consisted of 100 microliters of the described emulsion containing liposomes (13.2 milligrams of DOPC/cholesterol), FP antigen (15 micrograms), polyI:C adjuvant (150 micrograms), and the mineral oil carrier. This vaccine formulation will be referred to as liposome/polyI:C/hydrophobic carrier.

Figure 11:
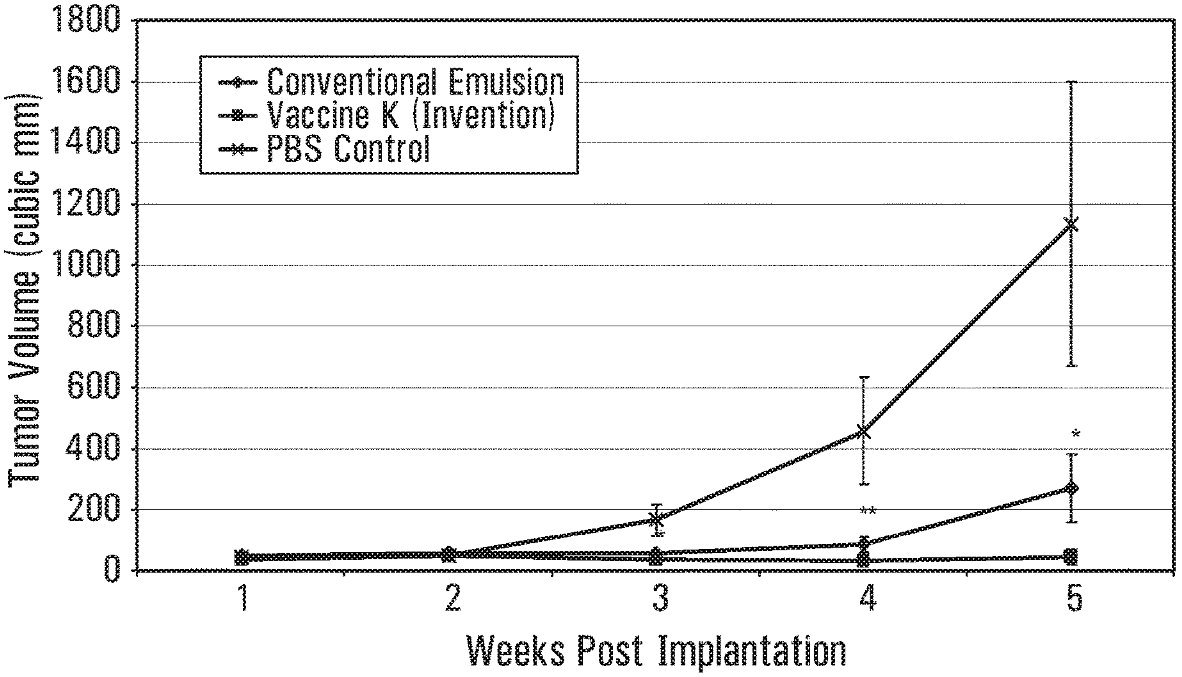
FIG. 11 is a graph showing the average tumor volume of C57BL/6 mice implanted with HPV16 E7 expressing C3 cells and vaccinated eight days later as follows: Group 1 mice were vaccinated with 100 microliters containing 15 micrograms of FP antigen and 150 micrograms of RNA-based polyI:C formulated in an emulsion with hydrophobic carrier (Control Emulsion vaccine). Group 2 mice were vaccinated with 100 microliters containing 15 micrograms of FP antigen and 150 micrograms of polyI:C formulated in liposome/PolyI:C/hydrophobic carrier (Vaccine K, invention). Group 3 mice received 100 microliters of PBS only. All groups contained eight mice. Tumor size was measured once a week for five weeks after implantation.

The results of this experiment are shown in FIG. 11. Group 1 mice had partial protection from tumor growth and started to develop measurable tumors by week 4 post implantation. The mice in Group 2, vaccinated with the invention, developed significantly smaller tumors that were only detectable by week 5 ($p<0.1$). The mice in the control group developed tumors with expected kinetics, starting at week 3 post implantation.

These results indicate that tumor-specific antigens formulated in the liposome/polyI:C/hydrophobic carrier formulation was more effective at therapeutically treating an established tumor in mice than when formulated with polyI:C/hydrophobic carrier. The optimal therapeutic effect could only be achieved when liposomes were present in the formulation, clearly indicating that liposomes are a critical component of the invention.

Example 12

Pathogen free, female C57BL6 mice, 4-6 weeks of age, were obtained from Charles River Laboratories (St Constant, QC, Canada) and were housed according to institutional guidelines with water and food ad libitum, under filter controlled air circulation.

As in Example 11, the antigen used in vaccine formulations was a fusion protein consisting of the H2-Db immunodominant epitope of HPV16 E7 (49-57; RAHYNIVTF) fused to the universal T helper epitope PADRE. This antigen, hereafter referred to as FP, was synthesized by Anaspec Inc. (San Jose, Calif.). The adjuvant was a DNA-based poly inosine-cytosine DNA molecule consisting of 13 (IC) repeats and synthesized by Operon MWG (Huntsville, Ala., USA).

The efficacy of the invention comprising liposomes, a DNA-based polyI:C and a hydrophobic carrier was tested in vivo using the C3 tumor challenge model described earlier. Four groups of mice (n=8 per group) were implanted subcutaneously in the flank with the HPV16 E7 expressing tumor cell line C3 (5×10^5 cells/mouse) on day 0. On day 5, mice in Groups 1 to 3 were vaccinated subcutaneously in the opposing flank with vaccine. Group 4 mice received PBS only and served as the tumor growth control. Tumor volume was measured once a week using callipers to record the shortest diameter and longest diameter for 5 weeks post implantation. Tumor volume was calculated using the following formula: longest measurement×(shortest measurement^2 divided by 2.

Mice in Group 1 were vaccinated with Vaccine L comprising a liposome/antigen/poly IC/hydrophobic carrier. The vaccine was formulated as in Example 11. Each dose volume was 100 microliters and contained liposomes, FP (10 micrograms), poly IC (20 micrograms) and was emulsified with the mineral oil carrier. Mice in Group 2 were vaccinated with Vaccine M comprising a lyophilized liposome/antigen/poly IC/hydrophobic carrier. Briefly, a 10:1 (w:w) homogenous mixture of DOPC lecithin and cholesterol (Lipoid GmbH, Germany) was hydrated in the presence of 200 micrograms of FP and 400 micrograms of poly IC in 0.5% PEG/water to form 1 milliliter of liposomes with encapsulated antigen and adjuvant. The liposome preparation was extruded by passing the material 20 times through a manual extruder (Avanti, Alabaster, Ala., USA) fitted with two 400 nanometer polycarbonate membranes. Liposome size was confirmed at 200 nanometers using a Malvern Particle Size Analyzer (Worchestershire, United Kingdom). Liposomes containing antigen and adjuvant were lyophilized using the Virtis Advantage freeze dryer (SP Industries, Warminister, Pa., USA). The lyophilized material was reconstituted in oil up to the original volume of solublized liposomes with a mineral oil carrier (Montanide™ ISA 51, Seppic, France). Each dose volume was 50 microliters and contained liposomes (6.6 mg of DOPC/cholesterol), FP (10 micrograms), polyI:C (20 micrograms) and the mineral oil carrier. Mice in Group 3 were vaccinated with a lyophilized liposome/antigen/hydrophobic carrier formulated as for Group 2, except without the poly IC adjuvant (adjuvant control).

Figure 12:
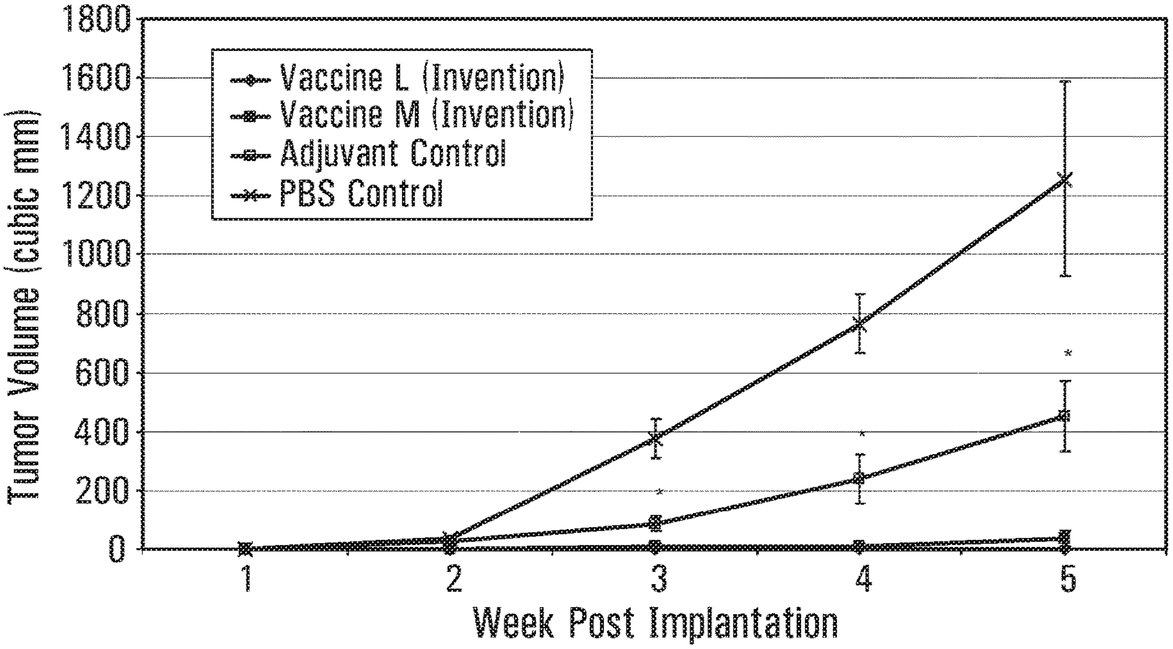
FIG. 12 is a graph showing the average tumor volume of C57BL/6 mice implanted with HPV16 E7 expressing C3 cells and vaccinated five days later as follows: Group 1 mice received 100 microliters containing 10 micrograms of FP antigen and 20 micrograms of DNA based polyI:C formulated in liposome/PolyI:C/hydrophobic carrier (Vaccine L, invention). Group 2 mice received 50 microliters containing 10 micrograms of FP antigen and 20 micrograms of DNA based polyI:C formulated in lyophilized liposome/PolyI:C/hydrophobic carrier (Vaccine M, invention). Group 3 mice received 50 microliters containing 10 micrograms of FP antigen formulated in lyophilized liposome/hydrophobic carrier (Adjuvant control). Group 4 mice received 100 microliters of PBS only. All groups contained ten (10) mice. Tumor size was measured once a week for five weeks after implantation.
Figure 13:
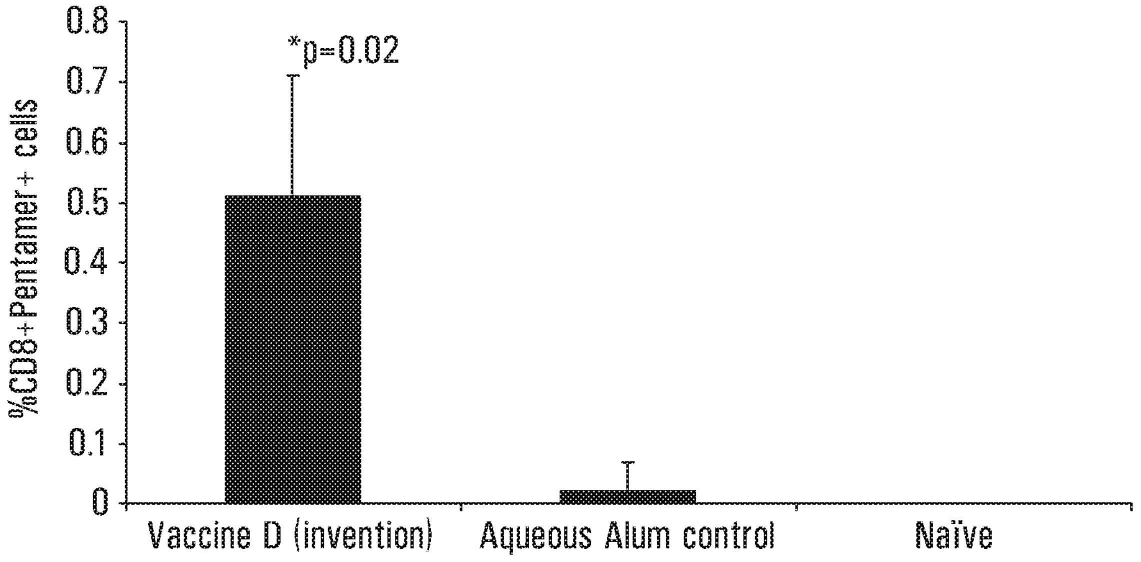
FIG. 13. Enhanced anti-rHA cellular response following vaccination with rHA antigen formulated in a lyophilized liposome/polyI:C/oil carrier vaccine. Two groups of mice (n=9 or 10) were immunized as follows: Group 1 mice were vaccinated with a single dose of 1.5 micrograms rHA and 12.5 micrograms polyI:C in a 50 microliter dose formulated as a lyophilized liposome/polyI:C/hydrophobic carrier vaccine (Vaccine D, the invention). Group 2 mice were treated with 1.5 micrograms rHA and 100 micrograms alum per 50 microliter dose of control alum vaccine; mice were boosted 28 days (week 4) post-vaccination. Antigen specific cellular responses were measured by pentamer staining of CD8+ T cells specific for the H2-Kd epitope IYSTVASSL and flow cytometry. Mice vaccinated with the invention as described generated an antigen-specific long-lasting cellular response. P values were calculated using the Student T test.

Results of this experiment are shown in FIG. 12. Group 1 and group 2 mice did not develop measurable tumors throughout the length of the study. Mice in Group 3, which were vaccinated with the lyophilized liposome formulation with FP but no adjuvant, started to develop tumors at week 3 post implantation. Mice in the PBS control group developed tumors with expected kinetics, starting at week 3 post implantation.

These results indicate that vaccine formulations of the present invention require a poly IC adjuvant to be efficacious in a tumor challenge model. In this example, a DNA-based polyI:C adjuvant formulated in a liposome/hydrophobic carrier or in a lyophilized liposome/hydrophobic carrier formulation generated an effective immune response with therapeutic effect with as little as one immunization.

Example 13

Pathogen free, female BALB/c mice, 6-8 weeks of age, were obtained from Charles River Laboratories (St Constant, QC, Canada) and were housed according to institutional guidelines with water and food ad libitum, under filter controlled air circulation.

As in previous examples, H5N1 recombinant hemagglutinin protein, corresponding to the hemagglutinin glycoprotein on the surface of the H5N1 influenza virus, was purchased from Protein Sciences (Meridien, Conn., USA). This recombinant protein, hereafter designated rHA, was used as a model antigen to test the efficacy of vaccine formulations. rHA was used at 1.5 micrograms per 50 microliter dose.

Vaccine efficacy was assessed by immunofluorescence staining of memory CD8 cells, similar to the method described in Example 7. Syngenic splenocytes from BALB/c mice were activated for 48 hours at 37 degrees Celsius with 10 micrograms/milliliter of lipopolysaccharide and the resulting blasts were treated with 50 micrograms/milliliter mitomycin C for 20 minutes at room temperature. Following repeated washes, the activated blast cells were used as antigen presenting stimulator cells for expanding flu-specific CD8 memory cells from vaccinated mice. Spleen cells from naïve or immunized mice were cultured with blast cells at a ratio of 5:1 and cultures were stimulated with rHA at 0.1 micrograms/milliliter for 6 days at 37 degrees Celsius, 5 percent carbon dioxide. Harvested cells were used for immunofluorescence staining with anti-CD8-fluorescein isothiocyanate (FITC) (eBioscience, San Diego, Calif., USA) antibodies and phycoerythrin (PE)-conjugated Pro5 Flu-pentamer reagent (H2-Kd, IYSTVASSL, Proimmune, Oxford, UK). Anti-CD19-allophycocyanin (APC) (eBioscience) was also used to exclude any non-specific binding of pentamer to B cells. Stained cells were collected on a FACSCalibur flow-cytometer (BD Bioscience, Mississauga, ON, Canada) and data analysis was done using WnList 6.0 software (Verity Software House, Topsham, Me., USA). Results were gated based on forward and side scatter, and antigen-specific CD8 T cells were defined as pentamer positive, CD8β positive and CD19 negative. Statistical analysis was performed using Students' T-test.

To formulate the vaccine corresponding to the invention, the same procedures as described in Examples 6 and 7 were used. In summary, a 10:1 (w:w) homogeneous mixture of S100 lecithin and cholesterol (Lipoid GmbH, Germany) was hydrated in the presence of rHA in phosphate buffer (pH 7.0), to form liposomes encapsulating rHA, and followed by the addition of RNA-based polyI:C (Pierce, Rockford, Ill., USA). The liposome suspension was extruded through a semi-automatic extruder (Avestin, Ottawa, ON, Canada) and the sized liposomes lyophilized (Virtis Advantage freeze dryer, SP Industries, Warminister, Pa., USA) and reconstituted in a mineral oil carrier (Montanide ISA 51™, SEPPIC, France). Each vaccine dose consisted of 50 microliters of the above described formulation containing liposomes, rHA antigen, polyI:C adjuvant, and the mineral oil carrier. This vaccine formulation will be referred to as lyophilized liposome/polyI:C/hydrophobic carrier.

The efficacy of the lyophilized liposome formulation described above was compared to the efficacy of a control vaccine consisting of 1.5 micrograms of rHA and 100 micrograms of Imject Alum adjuvant (Pierce, Rockford, Ill., USA) in 50 microliters of 50 millimolar phosphate buffer (pH 7.0). Group 1 mice (N=5) were injected intramuscularly, once (no boosting), with 1.5 micrograms of rHA antigen and 12.5 micrograms of polyI:C adjuvant formulated in 50 microliters of lyophilized liposome/polyI:C/hydrophobic carrier as described above. This vaccine corresponds to the same vaccine used in Examples 6 and 7 (vaccine D, the invention). Group 2 mice (N=5) were vaccinated twice (day 0 and day 28) with a control vaccine consisting of 1.5 micrograms of rHA and 100 micrograms of alum adjuvant suspended in 50 millimolar phosphate buffer. Twenty-one weeks post-vaccination, animals were euthanized by carbon dioxide induced asphyxiation, the spleens were collected and individual single cell suspensions prepared using standard procedures. The presence of flu-specific CD8 memory T cells was then assessed using the flu pentamer immunofluorescence staining described above.

Mice vaccinated with the control alum-based formulation generated a small population of antigen-specific CD8 memory T cells, mean population size of 0.02 percent and considered background (standard deviation 0.02 percent). Mice vaccinated with the lyophilized liposome/polyI:C/hydrophobic carrier formulation corresponding to the invention on the other generated a significantly higher population ($P<0.02$) of antigen-specific CD8 memory T cells, mean population size of 0.51 percent (standard deviation 0.10 percent). These results are significant as they demonstrate that single dose lyophilized liposome/hydrophobic carrier formulations containing polyI:C adjuvant generate a large, long-lasting, antigen-specific CD8 memory T cell population whereas an aqueous/alum control vaccine could not generate any significant and lasting cellular response even after two immunizations.

REFERENCES

Yoneyama M, Kikuchi M, Natsukawa T, Shinobu N, Imaizumi T, Miyagishi M, Taira K, Akira S, Fujita T. 2004. The RNA helicase RIG-I has an essential function in double-stranded RNA-induced innate antiviral responses. Nat Immunol 5(7):730-7.

Dong L W, Kong X N, Yan H X, Yu L X, Chen L, Yang W, Liu Q, Huang D D, Wu M C, Wang H Y. 2008. Signal regulatory protein alpha negatively regulates both TLR3 and cytoplasmic pathways in type I interferon induction. Mol Immunol 45(11):3025-35. Epub 2008 May 8.

Trumpfheller C, Caskey M, Nchinda G, Longhi M P, Mizenina O, Huang Y, Schlesinger S J, Colonna M, Steinman R M. 2008. The microbial mimic poly IC induces durable and protective CD4+ T cell immunity together with a dendritic cell targeted vaccine. Proc Natl Acad Sci USA 2008 Feb. 19; 105(7):2574-9.

Alexopoulou L, Holt A C, Medzhitov R, Flavell R A. 2001. Recognition of double-stranded RNA and activation of N F-kappaB by Toll-like receptor 3. Nature 413(6857):732-8.

Chirigos M A, Schlick E, Ruffmann R, Budzynski W, Sinibaldi P, Gruys E. 1985. J Biol Response Mod 4(6): 621-7. Pharmacokinetic and therapeutic activity of polyinosinic-polycytidylic acid stabilized with poly-L-lysine in carboxymethylcellulose [poly(I,C)-LC].

Gowen B B, Wong M H, Jung K H, Sanders A B, Mitchell W M, Alexopoulou L, Flavell R A, Sidwell R W. 2007. TLR3 is essential for the induction of protective immunity against Punta Toro Virus infection by the double-stranded RNA (dsRNA), poly(I:C12U), but not Poly(I:C): differential recognition of synthetic dsRNA molecules. J Immunol 178(8):5200-8.

Padalko E, Nuyens D, De Palma A, Verbeken E, Aerts J L, De Clercq E, Carmeliet P, Neyts J. 2004. The interferon inducer ampligen [poly(I)-poly(C12U)] markedly protects mice against coxsackie B3 virus-induced myocarditis. Antimicrob Agents Chemother 48(1):267-74.

Nordlund J J, Wolff S M, Levy H B. 1970. Inhibition of biologic activity of poly I: poly C by human plasma. Proc Soc Exp Biol Med 133(2):439-44.

Agger E M, Rosenkrands I, Olsen A W, Hatch G, Williams A, Kritsch C, Lingnau K, von Gabain A, Andersen C S, Korsholm K S, Andersen P. 2006. Protective immunity to tuberculosis with Ag85B-ESAT-6 in a synthetic cationic adjuvant system IC31. Vaccine 24(26):5452-60.

Schellack C, Prinz K, Egyed A, Fritz J H, Wttmann B, Ginzler M, Swatosch G, Zauner W, Kast C, Akira S, von Gabain A, Buschle M, Lingnau K. 2006. IC31, a novel adjuvant signaling via TLR9, induces potent cellular and humoral immune responses. Vaccine 24(26):5461-72.

Llopiz D, Dotor J, Zabaleta A, Lasarte J J, Prieto J, Borrás-Cuesta F, Sarobe P. 2008. Combined immunization with adjuvant molecules poly(I:C) and anti-CD40 plus a tumor antigen has potent prophylactic and therapeutic antitumor effects. Cancer Immunol Immunother 57(1):19-29.

Riedl K, Riedl R, von Gabain A, Nagy E, Lingnau K. 2008. The novel adjuvant IC31((R)) strongly improves influenza vaccine-specific cellular and humoral immune responses in young adult and aged mice. Vaccine 2008 May 5 epub.

Levy H B. 1985. J Biol Response Mod 4(5):475-80. Historical overview of the use of polynucleotides in cancer.

Ichinohe T, Tamura S, Kawaguchi A, Ninomiya A, Imai M, Itamura S, Odagiri T, Tashiro M, Takahashi H, Sawa H, Mitchell W M, Strayer D R, Carter W A, Chiba J, Kurata T, Sata T, Hasegawa H. 2007. Cross-protection against H5N1 influenza virus infection is afforded by intranasal inoculation with seasonal trivalent inactivated influenza vaccine. J Infect Dis 196(9):1313-20.

Sloat B R, Shaker D S, Le U M, Cui Z. 2008. Nasal immunization with the mixture of PA63, L F, and a PGA conjugate induced strong antibody responses against all three antigens. FEMS Immunol Med Microbiol 52(2): 169-79.

Salem M L, El-Naggar S A, Kadima A, Gillanders W E, Cole D J. 2006. The adjuvant effects of the toll-like receptor 3 ligand polyinosinic-cytidylic acid poly (I:C) on antigen-specific CD8+ T cell responses are partially dependent on N K cells with the induction of a beneficial cytokine milieu. Vaccine 24(24):5119-32.

Kamath A T, Valenti M P, Rochat A F, Agger E M, Lingnau K, von Gabain A, Andersen P, Lambert P H, Siegrist C A. 2008. Protective anti-mycobacterial T cell responses through exquisite in vivo activation of vaccine-targeted dendritic cells. Eur J Immunol. 38(5):1247-56.

Cui Z, Qiu F. 2006. Synthetic double-stranded RNA poly(I:C) as a potent peptide vaccine adjuvant: therapeutic activity against human cervical cancer in a rodent model. Cancer Immunol Immunother 55(10):1267-79.

Salem M L, Kadima A N, Cole D J, Gillanders W E. 2005. Defining the antigen-specific T-cell response to vaccination and poly(I:C)/TLR3 signaling: evidence of enhanced primary and memory CD8 T-cell responses and antitumor immunity. J Immunother. 28(3):220-8.

Fujimura T, Nakagawa S, Ohtani T, Ito Y, Aiba S. 2006. Inhibitory effect of the polyinosinic-polycytidylic acid/cationic liposome on the progression of murine B16F10 melanoma. Eur J Immunol 36(12):3371-80.

Krown S E, Kerr D, Stewart W E 2nd, Field A K, Oettgen H F. 1985. Phase I trials of poly(I,C) complexes in advanced cancer. J Biol Response Mod 1985 December; 4(6):640-9.

Zhu X, Nishimura F, Sasaki K, Fujita M, Dusak J E, Eguchi J, Fellows-Mayle W, Storkus W J, Walker P R, Salazar A M, Okada H. 2007. Toll like receptor-3 ligand poly-ICLC promotes the efficacy of peripheral vaccinations with tumor antigen-derived peptide epitopes in murine CNS tumor models. J Transl Med. 12:10.

de Clercq E, Torrence P F, Stollar B D, Hobbs J, Fukui T, Kakiuchi N, Ikehara M. 1978. Interferon induction by a 2'-modified double-helical RNA, poly(2'-azido-2'-deoxyinosinic acid). polycytidylic acid. Eur J Biochem. 88(2):341-9.

Bobst A M, Langemeier P W, Torrence P F, De Clercq E. 1981. Interferon induction by poly(inosinic acid).poly (cytidylic acid) segmented by spin-labels. Biochemistry 20(16):4798-803.

De Clercq E, Hattori M, Ikehara M. 1975. Antiviral activity of polynucleotides: copolymers of inosinic acid and N2-dimethylguanylic of 2-methylthioinosinic acid. Nucleic Acids Res 1975 2(1):121-9.

Guschlbauer W, Blandin M, Drocourt J L, Thang M N. 1977. Poly-2'-deoxy-2'-fluoro-cytidylic acid: enzymatic synthesis, spectroscopic characterization and interaction with poly-inosinic acid. Nucleic Acids Res 4(6):1933-43.

Fukui T, Kakiuchi N, Ikehara M. Polynucleotides. 1977. XLV Synthesis and properties of poly(2'-azido-2'-deoxyinosinic acid). Nucleic Acids Res. 4(8):2629-39.

Johnston M I, Stollar B D, Torrence P F, Witkop B. 1975. Structural features of double-stranded polyribonucleotides required for immunological specificity and interferon induction. Proc Natl Acad Sci USA. 72(11):4564-8.

Kende M, Lupton H W, Rill W L, Gibbs P, Levy H B, Canonico P G. 1987. Ranking of prophylactic efficacy of poly(ICLC) against Rift Valley fever virus infection in mice by incremental relative risk of death. Antimicrob Agents Chemother. 31(8):1194-8.

Poast J, Seidel H M, Hendricks M D, Haslam J A, Levy H B, Baron S. 2002. Poly I:CLC induction of the interferon system in mice: an initial study of four detection methods. J Interferon Cytokine Res 22(10):1035-40.

Sarma P S, Shiu G, Neubauer R H, Baron S, Huebner R J. 1969. Proc Natl Acad Sci USA 62(4):1046-51. Virus-induced sarcoma of mice: inhibition by a synthetic polyribonucleotide complex.

Stephen E L, Sammons M L, Pannier W L, Baron S, Spertzel R O, Levy H B. 1977. Effect of a nuclease-resistant derivative of polyriboinosinic-polyribocytidylic acid complex on yellow fever in rhesus monkeys (*Macaca mulatta*). J Infect Dis 136(1):122-6.

Levy H B, Lvovsky E. 1978. Topical treatment of vaccinia virus infection with an interferon inducer in rabbits. J Infect Dis. 137(1):78-81.

Durie B G, Levy H B, Voakes J, Jett J R, Levine A S. 1985. Poly(I,C)-L C as an interferon inducer in refractory multiple myeloma. J Biol Response Mod. 4(5):518-24.

Salazar A M, Levy H B, Ondra S, Kende M, Scherokman B, Brown D, Mena H, Martin N, Schwab K, Donovan D, Dougherty D, Pulliam M, Ippolito M, Graves M, Brown H, Ommaya A. 1996. Long-term treatment of malignant gliomas with intramuscularly administered polyinosinic-polycytidylic acid stabilized with polylysine and carboxymethylcellulose: an open pilot study. Neurosurgery 38(6):1096-103; discussion 1103-4.

Theriault R L, Hortobagyi G N, Buzdar A U, Levy H B, Hersh E M. 1986. Evaluation of polyinosinic-polycytidylic and poly-L-lysine in metastatic breast cancer. Cancer Treat Rep. 70(11):1341-2.

Nakamura O, shitara N, Matsutani M, Takakura K, Machida H. 1982. Phase I-II trials of poly(ICLC) in malignant brain tumor patients. J Interferon Res 2(1):1-4.

Bever C T Jr, Salazar A M, Neely E, Ferraraccio B E, Rose J W, McFarland H F, Levy H B, McFarlin D E. 1986. Preliminary trial of poly ICLC in chronic progressive multiple sclerosis. Neurology 36(4):494-8.

Talmadge J E, Adams J, Phillips H, Collins M, Lenz B, Schneider M, Chirigos M. 1985. Immunotherapeutic potential in murine tumor models of polyinosinic-polycytidylic acid and poly-L-lysine solubilized by carboxymethylcellulose. Cancer Res 45(3):1066-72.

Droller M J. 1987. Immunotherapy of metastatic renal cell carcinoma with polyinosinic-polycytidylic acid. J Urol. 137(2):202-6.

Awasthi A, Mehrotra S, Bhakuni V, Dutta G P, Levy H B, Maheshwari R K. 1997. Poly ICLC enhances the antimalarial activity of chloroquine against multidrug-resistant *Plasmodium yoelii nigeriensis* in mice. J Interferon Cytokine Res. 17(7):419-23.

Puri S K, Dutta G P, Levy H B, Maheshwari R K. 1996. Poly ICLC inhibits Plasmodium cynomolgi B malaria infection in rhesus monkeys. J Interferon Cytokine Res. 16(1):49-52.

Houston W E, Crabbs C L, Stephen E L, Levy H B. 1976. Modified polyriboinosinic-polyribocytidylic acid, an immunological adjuvant. Infect Immun 14(1):318-9.

Stephen E L, Hilmas D E, Mangiafico J A, Levy H B. 1977. Swine influenza virus vaccine: potentiation of antibody responses in rhesus monkeys. Science 197(4310):1289-90.

Zaks K, Jordan M, Guth A, Sellins K, Kedl R, Izzo A, Bosio C, Dow S. 2006. Efficient immunization and cross-priming by vaccine adjuvants containing TLR3 or TLR9 agonists complexed to cationic liposomes. J Immunol 176(12):7335-45.

Hendrix C W, Margolick J B, Petty B G, Markham R B, Nerhood L, Farzadegan H, Ts'o P O, Lietman P S. 1993. Biologic effects after a single dose of poly(I):poly(C12U) in healthy volunteers. Antimicrob Agents Chemother. 37(3):429-35.

Greene J J, Alderfer J L, Tazawa I, Tazawa S, Ts'o P O, O'Malley J A, Carter W A. 1978. Interferon induction and its dependence on the primary and secondary structure of poly(inosinic acid).poly(cytidylic acid). Biochemistry 17(20):4214-20.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A composition, comprising:

(a) an antigen that is expressed by a tumor cell;

(b) liposomes;

(c) a DNA-based polyI:C polynucleotide; and (d) a carrier comprising a continuous phase of a hydrophobic substance.

2. The composition according to claim 1, wherein the DNA-based polyI:C polynucleotide is a homopolymer or a heteropolymer.

3. The composition according to claim 1, wherein the DNA-based polyI:C polynucleotide comprises a homopolymeric polyI:C polynucleotide and a heteropolymeric polyI:C polynucleotide.

4. A method for making a composition, said method comprising combining, in any order:

(a) an antigen that is expressed by a tumor cell;

(b) liposomes;

(c) a DNA-based polyI:C polynucleotide; and (d) a carrier comprising a continuous phase of a hydrophobic substance.

5. The method according to claim 4, wherein said antigen is encapsulated in said liposomes.

6. The method according to claim 4, wherein said DNA-based polyI:C polynucleotide is encapsulated in said liposomes.

7. The method according to claim 4, wherein said DNA-based polyI:C polynucleotide is added outside said liposomes.

8. A composition prepared according to the method of claim 4.

9. A method for inhibiting the growth of a tumor in a subject, comprising administering to the subject a composition comprising:

(a) an antigen that is expressed by a tumor cell of the tumor;

(b) liposomes;

(c) a DNA-based polyI:C polynucleotide; and (d) a carrier comprising a continuous phase of a hydrophobic substance.

10. The method according to claim 9, wherein the composition is administered via a route that is nasal, oropharyngeal, ocular, oral, rectal, sublingual, genitourinary mucosa, intranasal, oropharyngeal, intratracheal, intrapulmonary, transdermal, transpulmonary, intraarterial, intradermal, intramuscular, intraperitoneal, intravenous, subcutaneous or submucosal.

11. The composition according to claim 1, wherein the liposomes are non-cationic.

12. The method according to claim 9, wherein the liposomes are non-cationic.

13. The method according to claim 9, wherein the composition is administered by subcutaneous or intramuscular injection.

14. The composition according to claim 1, wherein the DNA-based polyI:C polynucleotide is a poly inosine-cytosine DNA molecule consisting of 13 (IC) repeats.

15. The method according to claim 9, wherein the DNA-based polyI:C polynucleotide is a poly inosine-cytosine DNA molecule consisting of 13 (IC) repeats.

16. The composition according to claim 1, wherein the liposomes consist of cholesterol and a lipid selected from the group consisting of dioleoyl phosphatidylcholine (DOPC) and S100 lecithin.

17. The method according to claim 9, wherein the liposomes consist of cholesterol and a lipid selected from the group consisting of dioleoyl phosphatidylcholine (DOPC) and S100 lecithin.

18. The composition according to claim 1, wherein the carrier comprises mannide oleate and a continuous phase of mineral oil.

19. The method according to claim 9, wherein the carrier comprises mannide oleate and a continuous phase of mineral oil.

20. The composition according to claim 1, wherein the DNA-based polyI:C polynucleotide is a poly inosine-cytosine DNA molecule consisting of 13 (IC) repeats, wherein the liposomes consist of cholesterol and a lipid selected from the group consisting of dioleoyl phosphatidylcholine (DOPC) and S100 lecithin, and wherein the carrier comprises mannide oleate and a continuous phase of mineral oil.

21. The method according to claim 9, wherein the DNA-based polyI:C polynucleotide is a poly inosine-cytosine DNA molecule consisting of 13 (IC) repeats, wherein the liposomes consist of cholesterol and a lipid selected from the group consisting of dioleoyl phosphatidylcholine (DOPC) and S100 lecithin, and wherein the carrier comprises mannide oleate and a continuous phase of mineral oil.

22. The composition according to claim 1, wherein the composition induces both an antibody immune response and a cell-mediated immune response in a subject.

23. The method according to claim 9, wherein the composition induces both an antibody immune response and a cell-mediated immune response in the subject.

24. The composition according to claim 1, wherein the liposomes are dehydrated before being suspended in the carrier.

25. The method according to claim 4, wherein the liposomes are dehydrated before being suspended in the carrier.

26. The method according to claim 9, wherein the liposomes are dehydrated before being suspended in the carrier.

* * * * *